US010478131B2

United States Patent
Jain et al.

(10) Patent No.: US 10,478,131 B2
(45) Date of Patent: Nov. 19, 2019

(54) DETERMINING BASELINE CONTEXTS AND STRESS COPING CAPACITY

(71) Applicant: Samsung Electronics Company, Ltd., Suwon, Gyeong gi-Do (KR)

(72) Inventors: Jawahar Jain, Los Altos, CA (US); James Young, Menlo Park, CA (US); Cody Wortham, Mountain View, CA (US); Sajid Sadi, San Jose, CA (US); Pranav Mistry, Cupertino, CA (US)

(73) Assignee: Samsung Electronics Company, Ltd., Suwon (KR)

( * ) Notice: Subject to any disclaimer, the term of this patent is extended or adjusted under 35 U.S.C. 154(b) by 0 days.

(21) Appl. No.: 15/183,472

(22) Filed: Jun. 15, 2016

(65) Prior Publication Data

US 2017/0071537 A1    Mar. 16, 2017

Related U.S. Application Data

(60) Provisional application No. 62/202,153, filed on Aug. 6, 2015, provisional application No. 62/202,135, filed
(Continued)

(51) Int. Cl.
    *A61B 5/0456*      (2006.01)
    *A61B 5/00*      (2006.01)
    (Continued)

(52) U.S. Cl.
    CPC .......... *A61B 5/7278* (2013.01); *A61B 5/0006* (2013.01); *A61B 5/0013* (2013.01);
    (Continued)

(58) Field of Classification Search
None
See application file for complete search history.

(56) References Cited

U.S. PATENT DOCUMENTS 4,926,863 A * 5/1990 Alt ..................... A61N 1/36542
    607/18
5,593,431 A * 1/1997 Sheldon ............. A61N 1/36542
    607/19
(Continued)

FOREIGN PATENT DOCUMENTS

JP     11-313806 A    11/1999
JP     2014-132934 A    7/2014
(Continued)

OTHER PUBLICATIONS

ISR and WO for International Application No. PCT/KR2016/010836, dated Jan. 10, 2017.
(Continued)

*Primary Examiner* — Kennedy Schaetzle
(74) *Attorney, Agent, or Firm* — Baker Botts, L.L.P.

(57) ABSTRACT

A method for monitoring a health characteristic of a user based on one or more biological measurements may include selecting a context from a plurality of contexts, each context corresponding to a baseline health value, and each context being defined by a plurality of recorded events each comprising one or more of repeated biological states, repeated user activity, or space-time coordinates of the user, and then monitoring the health characteristic of the user based on one or more bio-sensing measurements in comparison to the baseline health value corresponding to the selected context.

20 Claims, 30 Drawing Sheets

Related U.S. Application Data on Aug. 6, 2015, provisional application No. 62/202,685, filed on Aug. 7, 2015, provisional application No. 62/193,509, filed on Jul. 16, 2015.

(51) Int. Cl.

| | |
|---|---|
| *A61B 5/16* | (2006.01) |
| *A61B 5/024* | (2006.01) |
| *A61B 5/053* | (2006.01) |
| *G16H 40/67* | (2018.01) |
| *G06F 19/00* | (2018.01) |
| *G16H 40/63* | (2018.01) |

(52) U.S. Cl.
CPC ........ *A61B 5/0022* (2013.01); *A61B 5/02405* (2013.01); *A61B 5/02416* (2013.01); *A61B 5/02438* (2013.01); *A61B 5/0456* (2013.01); *A61B 5/0533* (2013.01); *A61B 5/165* (2013.01); *A61B 5/486* (2013.01); *A61B 5/4884* (2013.01); *A61B 5/7203* (2013.01); *A61B 5/7225* (2013.01); *A61B 5/7275* (2013.01); *A61B 5/7282* (2013.01); *A61B 5/746* (2013.01); *G06F 19/3418* (2013.01); *G16H 40/63* (2018.01); *G16H 40/67* (2018.01); *A61B 5/681* (2013.01); *A61B 5/6833* (2013.01); *A61B 5/7257* (2013.01); *A61B 5/742* (2013.01); *A61B 5/7405* (2013.01); *A61B 5/7455* (2013.01); *A61B 5/7475* (2013.01); *A61B 2503/10* (2013.01); *A61B 2560/0209* (2013.01)

(56) References Cited

U.S. PATENT DOCUMENTS

| | | | |
|---|---|---|---|
| 5,891,044 A | 4/1999 | Golosarsky | |
| 7,532,924 B2* | 5/2009 | Ternes | A61B 5/0006 |
| | | | 600/523 |
| 8,529,447 B2 | 9/2013 | Jain | |
| 8,540,629 B2 | 9/2013 | Jain | |
| 8,617,067 B2 | 12/2013 | Jain | |
| 8,622,899 B2 | 1/2014 | Jain | |
| 8,622,900 B2 | 1/2014 | Jain | |
| 8,622,901 B2 | 1/2014 | Jain | |
| 8,852,093 B2 | 10/2014 | Clapp | |
| 8,941,500 B1* | 1/2015 | Faaborg | G08B 21/18 |
| | | | 340/539.11 |
| 9,173,567 B2 | 11/2015 | Jain | |
| 9,189,599 B2 | 11/2015 | Adler | |
| 9,421,420 B2* | 8/2016 | Zhang | A63B 24/0003 |
| 9,848,784 B2 | 12/2017 | Klepp | |
| 2004/0111033 A1 | 6/2004 | Oung | |
| 2005/0065443 A1* | 3/2005 | Ternes | A61B 5/0006 |
| | | | 600/509 |
| 2007/0021678 A1* | 1/2007 | Beck | A61B 5/0245 |
| | | | 600/510 |
| 2009/0287103 A1* | 11/2009 | Pillai | A61B 5/0245 |
| | | | 600/509 |
| 2010/0049095 A1 | 2/2010 | Bunn | |
| 2010/0056872 A1* | 3/2010 | Kahn | A61B 5/1038 |
| | | | 600/300 |
| 2010/0113889 A1* | 5/2010 | Ghanem | A61N 1/36564 |
| | | | 600/301 |
| 2010/0198608 A1 | 8/2010 | Kaboff | |
| 2010/0292545 A1 | 11/2010 | Berka | |
| 2011/0105860 A1* | 5/2011 | Houben | A61B 5/0205 |
| | | | 600/301 |
| 2011/0169603 A1* | 7/2011 | Fithian | G06Q 10/00 |
| | | | 340/5.52 |
| 2012/0029300 A1* | 2/2012 | Paquet | A61B 5/6833 |
| | | | 600/300 |
| 2012/0065480 A1 | 3/2012 | Badilini | |
| 2012/0071731 A1 | 3/2012 | Gottesman | |
| 2012/0095622 A1 | 4/2012 | Lynch | |
| 2012/0108915 A1* | 5/2012 | Corbucci | A61B 5/02028 |
| | | | 600/301 |
| 2012/0289789 A1 | 11/2012 | Jain | |
| 2013/0194066 A1* | 8/2013 | Rahman | G05B 1/01 |
| | | | 340/5.51 |
| 2014/0073486 A1 | 3/2014 | Ahmed | |
| 2014/0085050 A1* | 3/2014 | Luna | G07C 9/00087 |
| | | | 340/5.82 |
| 2014/0200468 A1 | 7/2014 | Cho | |
| 2014/0206944 A1 | 7/2014 | Jain | |
| 2014/0247143 A1 | 9/2014 | Proud | |
| 2014/0358472 A1 | 12/2014 | Goel | |
| 2014/0371608 A1 | 12/2014 | Nageshwar | |
| 2015/0099987 A1 | 4/2015 | Bhatkar | |
| 2015/0119728 A1 | 4/2015 | Blackadar | |
| 2015/0182129 A1 | 7/2015 | Colley | |
| 2015/0206053 A1* | 7/2015 | Hayden | G06N 5/02 |
| | | | 706/46 |
| 2015/0223746 A1 | 8/2015 | Bonnet | |
| 2015/0238140 A1 | 8/2015 | LaBelle | |
| 2015/0374310 A1* | 12/2015 | Lee | A61B 5/7285 |
| | | | 600/483 |
| 2016/0150978 A1 | 6/2016 | Yuen | |
| 2016/0324487 A1* | 11/2016 | Guo | G08B 21/0269 |
| 2017/0202177 A1 | 7/2017 | Loosveld | |

FOREIGN PATENT DOCUMENTS

| | | |
|---|---|---|
| KR | 10-2006-0031837 | 4/2006 |
| KR | 10-2006-0066708 | 6/2006 |
| KR | 100 954 817 | 4/2010 |
| KR | 100954817 B1 | 4/2010 |
| WO | WO 2006/0113660 | 10/2006 |
| WO | WO 2008/028004 | 3/2008 |
| WO | WO 2013/028581 | 2/2013 |
| WO | WO 2013/068650 | 5/2013 |
| WO | WO 2014/125159 | 8/2014 |
| WO | WO 2015/139980 | 9/2015 |

OTHER PUBLICATIONS

ISR and WO for International Application No. PCT/KR2016/010841, dated Jan. 10, 2017.
ISR and WO for International Application No. PCT/KR2016/010849, dated Jan. 10, 2017.
ISR and WO for International Application No. PCT/ KR2016/010845, dated Mar. 30, 2017.
U.S. Appl. No. 15/183,479, filed Jun. 15, 2016, Jain.
U.S. Appl. No. 15/183,481, filed Jun. 15, 2016, Jain.
U.S. Appl. No. 15/183,484, filed Jun. 15, 2016, Jain.
Non-Final Office Action for U.S. Appl. No. 15/183,481, dated Feb. 20, 2018.
Non-Final Office Action for U.S. Appl. No. 15/183,484, dated Mar. 14, 2018.
Response to Non-Final Office Action for U.S. Appl. No. 15/183,481, dated May 21, 2018.
European Patent Application No. 16905581.1 European Search Report, dated Apr. 10, 2019.
European Patent Application No. 16905583.7 European Search Report, dated Mar. 14, 2019.
European Patent Application No. 16905582.9 European Search Report, dated Feb. 5, 2019.
European Patent Application No. 16905584.5 European Search Report, dated Apr. 1, 2019.

\* cited by examiner

DETERMINING BASELINE CONTEXTS AND STRESS COPING CAPACITY

RELATED APPLICATION

This application claims the benefit, under 35 U.S.C. § 119(e), of U.S. Provisional Patent Application No. 62/202,153 filed 6 Aug. 2015, titled "Methods and Systems for Stress Detection," U.S. Provisional Patent Application No. 62/202,135 filed 6 Aug. 2015, titled "Improving Performance of Biological Measurements in Presence of Noise," U.S. Provisional Patent Application No. 62/202,685 filed 7 Aug. 2015, titled "Continuous Stress Measurement with Built-in Alarm Fatigue Proof Features," and U.S. Provisional Patent Application No. 62/193,509 filed 16 Jul. 2015, titled "Approaches to Understand Stress-Determined Baseline Contexts and Stress Coping Capacity," each of which is incorporated herein by reference.

TECHNICAL FIELD

This disclosure generally relates to improving usage and content for wearable electronic devices.

BACKGROUND

Mobile electronic devices provide a user with access to computing capabilities even as the user moves about various locations. Examples of mobile electronic devices include mobile phones, media players, laptops, tablets, personal digital assistants (PDAs), or hybrid devices that include functionality of multiple devices of this type.

Mobile electronic devices may be part of a communication network such as a local area network, wide area network, cellular network, the Internet, or any other suitable network. A mobile electronic device may use a communication network to communicate with other electronic devices, for example, to access remotely-stored data, access remote processing power, access remote displays, provide locally-stored data, provide local processing power, or provide access to local displays. For example, networks may provide communication paths and links to servers, which may host applications, content, and services that may be accessed or utilized by users via mobile electronic devices. The content may include text, video data, audio data, user settings or other types of data. Networks may use any suitable communication protocol or technology to facilitate communication between mobile electronic devices, such as, for example, BLUETOOTH, IEEE WI-FI (802.11a/b/g/n/ac), or Transmission Control Protocol/Internet Protocol (TCP/IP).

SUMMARY OF PARTICULAR EMBODIMENTS

In particular embodiments, a method for determining a stress level of a user based on a sympathovagal balance (SVB) value calculated based on a set of measurement data may include determining a heart-rate variability (HRV) characteristic as a ratio involving a number of autonomic nervous system (ANS) activity markers within a first portion of the set of measurement data and the number of ANS activity markers within a second portion of the set of measurement data, and then determining the stress level of the user based on the HRV characteristic. The first and second portions of the set of measurement data may be selected based on a user-specific baseline SVB value that divides a histogram representation of the set of measurement data into the first and second portions.

In particular embodiments, a method for determining a HRV measurement of a user may include receiving, from a sensor of an electronic device of the user, heart sensor data, determining a noise level of the heart sensor data, and then adjusting the HRV measurement by an amount calculated based on the determined noise level. The sensor data may include data on a photoplethysmograph (PPG) signal over a noise-calculation time period.

In particular embodiments, a method for monitoring a stress level of a user may include determining, based on biological measurements on one or more physiological markers received in a first sampling mode, the stress level of the user, and then dynamically switching to a second sampling mode when it is determined that one or more of the physiological markers are above a threshold level, the second sampling mode being different from the first sampling mode.

In particular embodiments, a method for monitoring a health characteristic of a user based on one or more biological measurements may include selecting a context from a plurality of contexts, each context corresponding to a baseline health value, and each context being defined by a plurality of recorded events each comprising one or more of repeated biological states, repeated user activity, or space-time coordinates of the user, and then monitoring the health characteristic of the user based on one or more bio-sensing measurements in comparison to the baseline health value corresponding to the selected context.

The embodiments disclosed above are only examples, and the scope of this disclosure is not limited to them. Particular embodiments may include all, some, or none of the components, elements, features, functions, operations, or steps of the embodiments disclosed above. Embodiments according to the invention are in particular disclosed in the attached claims directed to a method, a storage medium, a system and a computer program product, wherein any feature mentioned in one claim category, e.g. method, can be claimed in another claim category, e.g. system, as well. The dependencies or references back in the attached claims are chosen for formal reasons only. However any subject matter resulting from a deliberate reference back to any previous claims (in particular multiple dependencies) can be claimed as well, so that any combination of claims and the features thereof are disclosed and can be claimed regardless of the dependencies chosen in the attached claims. The subject-matter which can be claimed comprises not only the combinations of features as set out in the attached claims but also any other combination of features in the claims, wherein each feature mentioned in the claims can be combined with any other feature or combination of other features in the claims. Furthermore, any of the embodiments and features described or depicted herein can be claimed in a separate claim and/or in any combination with any embodiment or feature described or depicted herein or with any of the features of the attached claims.

DESCRIPTION OF EXAMPLE EMBODIMENTS

System Overview

Figure 1:
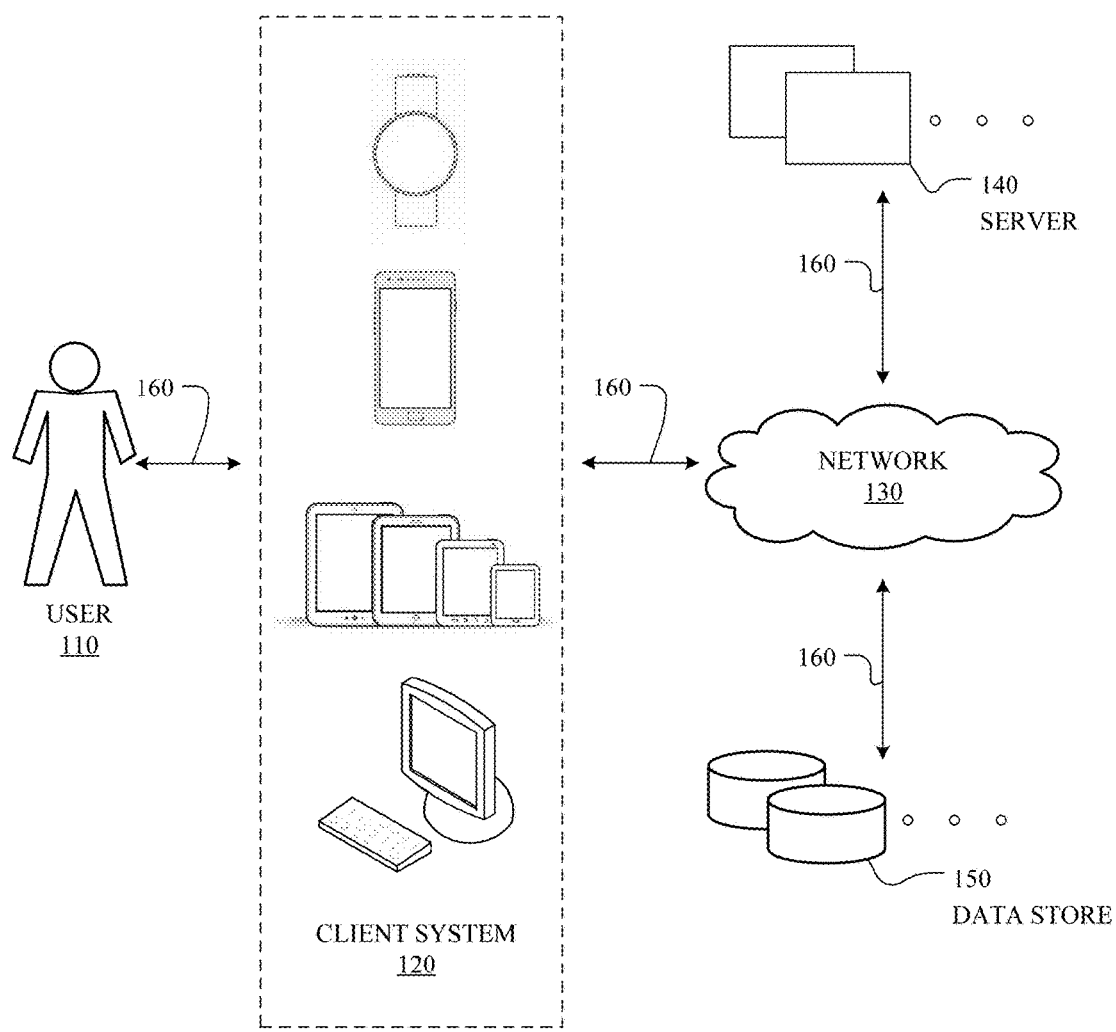
FIG. 1 illustrates an example network environment for particular embodiments of an optical detection system for internal body tissues and bone.

FIG. 1 illustrates an example network environment 100 for particular embodiments of a health monitoring system. Network environment 100 includes a user 110, a client system 120, a network 130, one or more servers 140, and one or more data stores 150. User 110, client system 120, servers 140, and data stores 150 may be connected to each other by network 130 via links 160. Although FIG. 1 illustrates a particular arrangement of user 110, client system 120, network 130, servers 140, and data stores 150, this disclosure contemplates any suitable arrangement of user 110, client system 120, network 130, servers 140, and data stores 150. As an example and not by way of limitation, two or more of client system 120, servers 140, and data stores 150 may be connected to each other directly, bypassing network 130. As another example, two or more of client system 120, servers 140, and data stores 150 may be physically or logically co-located with each other in whole or in part. Moreover, although FIG. 1 illustrates a particular number of user 110, client system 120, network 130, servers 140, and data stores 150, this disclosure contemplates any suitable number of user 110, client system 120, network 130, servers 140, and data stores 150. As an example and not by way of limitation, network environment 100 may include multiple users 110, client systems 120, networks 130, servers 140, and data stores 150.

In particular embodiments, user 110 may be an individual (e.g., human user), an entity (e.g., an enterprise, business, or third-party application), or a group (e.g., of individuals or entities) that interacts or communicates with client system 120. In particular embodiments, client system 120 may be any suitable computing device, such as, for example, a wearable computing device, a mobile computing device, a smartphone, a cellular telephone, a tablet computer, a laptop computer, a personal computer, an augmented/virtual reality device, or any combination thereof. User 110 may interact with one or more of these devices. In addition, these devices may communicate with each other via network 130, directly (e.g., by non-network connections), by any other suitable methods, or any combination thereof. As an example and not by way of limitation, the devices of client system 120 may communicate with network 130 via a wireless communications protocol, such as Wi-Fi or BLUETOOTH. In particular embodiments, client system 120 may include a web browser, such as MICROSOFT INTERNET EXPLORER, GOOGLE CHROME or MOZILLA FIREFOX, and may have one or more add-ons, plug-ins, or other extensions, such as TOOLBAR or YAHOO TOOLBAR. A user at client system 120 may enter a Uniform Resource Locator (URL) or other address directing the web browser to a particular server (such as server 140), and the web browser may generate a Hyper Text Transfer Protocol (HTTP) request and communicate the HTTP request to server. The server may accept the HTTP request and communicate to client system 120 one or more Hyper Text Markup Language (HTML) files responsive to the HTTP request. Client system 120 may render a webpage based on the HTML files from the server for presentation to the user. This disclosure contemplates any suitable webpage files. As an example and not by way of limitation, webpages may render from HTML files, Extensible Hyper Text Markup Language (XHTML) files, or Extensible Markup Language (XML) files, according to particular needs. Such pages may also execute scripts such as, for example and without limitation, those written in JAVASCRIPT, JAVA, MICROSOFT SILVERLIGHT, combinations of markup language and scripts such as AJAX (Asynchronous JAVASCRIPT and XML), and the like. Herein, reference to a webpage encompasses one or more corresponding webpage files (which a browser may use to render the webpage) and vice versa, where appropriate.

In particular embodiments, network 130 may be any suitable network. As an example and not by way of limitation, one or more portions of network 130 may include an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, or a combination of two or more of these. Network 130 may include one or more networks.

In particular embodiments, links 160 may connect client system 120, servers 140, and data stores 150 to network 130 or to each other. This disclosure contemplates any suitable links 160. In particular embodiments, one or more links 160 include one or more wireline (such as for example Digital Subscriber Line (DSL) or Data Over Cable Service Interface Specification (DOCSIS)), wireless (such as for example Wi-Fi or Worldwide Interoperability for Microwave Access (WiMAX)), or optical (such as for example Synchronous Optical Network (SONET) or Synchronous Digital Hierarchy (SDH)) links. In particular embodiments, one or more links 160 each include an ad hoc network, an intranet, an extranet, a VPN, a LAN, a WLAN, a WAN, a WWAN, a MAN, a portion of the Internet, a portion of the PSTN, a cellular technology-based network, a satellite communications technology-based network, another link 160, or a combination of two or more such links 160. Links 160 need not necessarily be the same throughout network environment 100. One or more first links 160 may differ in one or more respects from one or more second links 160.

In particular embodiments, servers 140 may be any suitable servers. Each server 140 may be a unitary server or a distributed server spanning multiple computers or multiple datacenters. Servers 140 may be of various types, such as, for example and without limitation, web server, file server, application server, exchange server, database server, proxy server, another server suitable for performing functions or processes described herein, or any combination thereof. In particular embodiments, each server 140 may include hardware, software, or embedded logic components or a combination of two or more such components for carrying out the appropriate functionalities implemented or supported by server 140.

In particular embodiments, data stores 150 may be any suitable data stores. Data stores 150 may be used to store various types of information. In particular embodiments, the information stored in data stores 150 may be organized according to specific data structures. In particular embodiments, each data store 150 may be a relational, columnar, correlation, or other suitable database. Data store 150 may include networked storage such as cloud storage or other network accessible storage. Additionally or alternatively, data store 150 may include local storage within or directly attached to any of the devices of client system 120, such as solid state drives ("SSDs") or hard disk drives ("HDDs"). Although this disclosure describes or illustrates particular types of components and uses of these component of network environment 100, this disclosure contemplates any suitable types of components, any suitable network topology (e.g., including a standalone-device topology), and any suitable uses for these components of network environment 100.

Health Monitoring and Applications Overview

Stress is considered to be one of the largest contributors to various health problems, and is estimated to be a contributory factor in more than 80% of all diseases. Particular embodiment discussed below focus on the measurement of stress in the context of mobile monitoring and management of health and/or wellness. In mobile monitoring and management, use of wearable sensors can be a key new technology for use in the analysis and management of stress and other physiological characteristics because this management can be a bridge to the management of a wide variety of health problems including diabetes, hypertension, cardiovascular diseases, pulmonary diseases, mood disorder, substance-abuse, overall quality of life, etc. The global wearable device market is a rapidly-growing market as wearable technology becomes an integral part of the Internet of Things in which a network of physical objects/things embedded with electronics, software, sensors, and network connectivity enables these objects/things to communicate with one another and collect and exchange data with one another.

Stress management techniques may work by measuring the activities/arousal of the autonomic nervous system (ANS), where high arousal is considered a sign of stress. For example, the arousal of ANS leads to changes in the physiology that may be easily measured via changes in heart rate, skin conductance, blood pressure, respiration, brain wave patterns via electroencephalography (EEG), other relevant metrics, or any combination thereof. Stress measurement techniques may rely on measurement of heart-rate variability (HRV). Measurements of HRV may be based on time-domain analysis or frequency-domain analysis, which both have numerous shortcomings.

As an example, frequency-domain analysis methods such as those based on fast Fourier transform (FFT), are not very suitable for implementation on mobile platforms since they are extremely sensitive to noise artifacts, and may require long measurement time periods. Time domain methods, such as root mean square of successive heartbeat interval differences (RMSSD), standard deviation of NN (beat-to-beat) intervals (SDNN), and the proportion of the number of pairs of successive NNs that are different by more than 50 millisecond divided by the total number of NNs (pNN50), are frequently used to analyze the instantaneous heart-rate signal. However, these methods may be inaccurate and instable, and this instability may become pronounced in the presence of noise, which is a phenomenon in a number of use models, such as in the context of wearable sensors. In addition, measurement of stress is, in a number of cases, meaningful only in the context of chronic and prolonged stress as short term spikes in stress, unless extremely sharp and unusual, are not very meaningful to alert the user about. Moreover, such methods may quantify stress without considering the context of the measurement or the baseline of the given user. As such, the methods may provide information that does not capture the true picture of the user's emotional health, and therefore the information provided by these methods is significantly less actionable.

In addition, applications of technologies for quantifying HRV may be hampered by a host of limitations that together make them impractical and difficult for mass adoption/implementation. For example, these technologies are based on weak and practically ineffective stress detection methods. In addition, these technologies are not focused on the relevant psychophysiological problems (acute and prolonged stress). Moreover, these technologies are not noise resilient and do not allow for any compensation of noise. The measurement of stress helps provide a measurement of emotional health which may then lead to stress management and modulation through a variety of approaches. However, these technologies may be fairly weak in creating a good marker of the emotional health (e.g., stress resilience). Lastly, the existing applications are very power hungry and difficult to implement in context of prolong, around-the-clock stress monitoring.

Particular embodiments described below address the inadequacies of the existing methods by providing a holistic suite of interactive features for measuring and monitoring various user-health indicators and providing useful and actionable feedback to the user. For example, particular embodiments described below are directed to systems and methods for stress monitoring and measurement that include a linear, ratio-based, and psychophysiological-measurement-based calculation determined from an analysis of sympathovagal balance (SVB) that treats the sympathetic nervous system (SNS) and parasympathetic nervous system (PSNS) with equal weightage. This SVB measurement has been determined to be both highly sensitive as well as specific in detecting mental states and stress levels of users, in addition to having a wide range of applicability to various other health measurements.

In addition, particular embodiments described below are directed to systems and methods for sampling and power efficiency in maintaining data-gathering sensors as on for only limited time periods necessary for determining various health measurements (e.g., to detect the onset of stress via heart rate measurements). Furthermore, particular embodiments described below are directed to systems and methods for providing the user with accurate data while not inundating the user with health-event and/or stress onset messages, in addition to lower false alarms. As an example, the user is only notified of highly harmful health events and/or stress events, which helps avoid alarm fatigue.

In addition, particular embodiments described below are directed to systems and methods for obtaining data and providing user feedback in an individualized, contextualized, and normalized manner. For example, health measurement baselines may be determined in an individualized basis for each user, and the health measurement data may be analyzed based on a user-specific context and normalized for all users to provide a meaningful measurement as feedback to the user. Furthermore, in the example of measuring stress, particular embodiments described below are directed to systems and methods for analyzing and monitoring not just stress, but also stress resilience as a marker of the user's stress coping skill. Also, particular embodiments described below are directed to systems and methods that allow for customizable refinement of the collected data to provide more use and insights for the user and/or other third parties (e.g., medical professionals).

In addition, particular embodiments described below are directed to systems and methods for improving the collection of health data by improving the performance of certain health measurements in the present of noise by signal correction techniques, including improving noise resiliency and providing noise-signal substitution in the presence of a high level of noise. Furthermore, particular embodiments described below are directed to systems and methods for compensating for the effects of noise by determining the range of likely errors due to noise, in addition to computing the displaying the extent of the noise to the user so that the user can understand the reliability of the measurements.

In particular embodiments, a method for determining a stress level of a user may be based on a SVB value calculated based on a set of measurement data, as discussed in detail below. The method may include determining a HRV characteristic as a ratio involving a number of ANS activity markers within a first portion of the set of measurement data and the number of ANS activity markers within a second portion of the set of measurement data, and then determining the stress level of the user based on the HRV characteristic. The first and second portions of the set of measurement data may be selected based on a user-specific baseline SVB value that divides a histogram representation of the set of measurement data into the first and second portions.

In particular embodiments, a method may determine a HRV measurement of a user in the presence of noise, and then detect and correct for the noise, as discussed in detail below. The method may include receiving, from a sensor of an electronic device of the user, sensor data, determining a noise level of the sensor data, and then adjusting the HRV measurement by an amount calculated based on the determined noise level. The sensor data may include data on a PPG signal over a noise-calculation time period.

In particular embodiments, a method may monitor a stress level of a user in a continuous manner while reducing alarm fatigue, as discussed in detail below. The method may include determining, based on biological measurements on one or more physiological markers received in a first sampling mode, the stress level of the user, and then dynamically switching to a second sampling mode when it is determined that one or more of the physiological markers are above a threshold level, the second sampling mode being different from the first sampling mode.

In particular embodiments, a method may monitor a health characteristic of a user based on one or more biological measurements to determine one or more contexts (e.g., a baseline context, other relevant contexts, etc.) associated with the measurements, as discussed in detail below. The method may include selecting a context from a plurality of contexts, each context corresponding to a baseline health value, and each context being defined by a plurality of recorded events each comprising one or more of repeated biological states, repeated user activity, or space-time coordinates of the user, and then monitoring the health characteristic of the user based on one or more bio-sensing measurements in comparison to the baseline health value corresponding to the selected context.

Example Embodiments of Health Monitoring Systems and User Interfaces

Figure 2A:
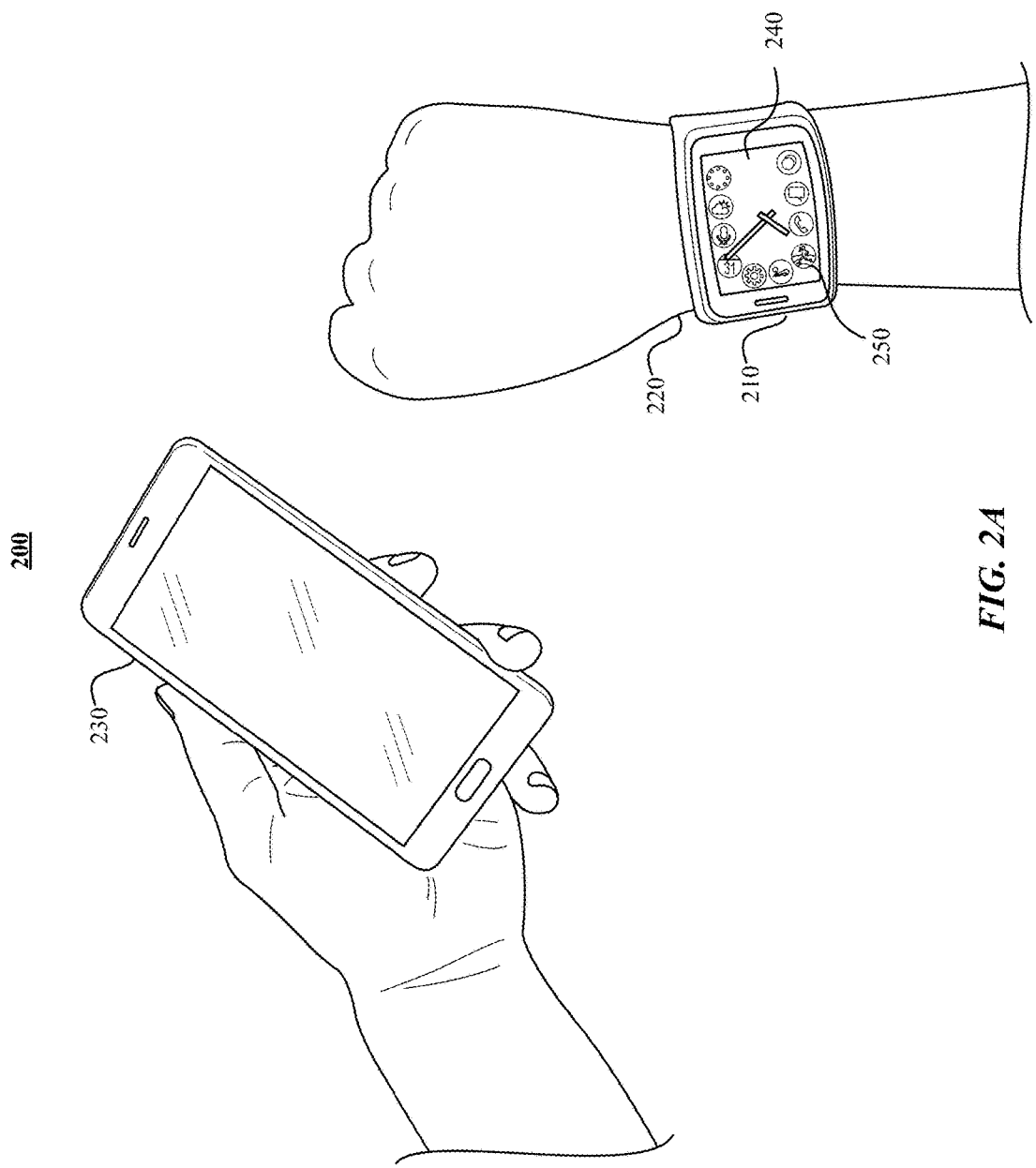
FIG. 2A illustrates an example health monitoring system including systems and devices according to particular embodiments.
Figure 2B:
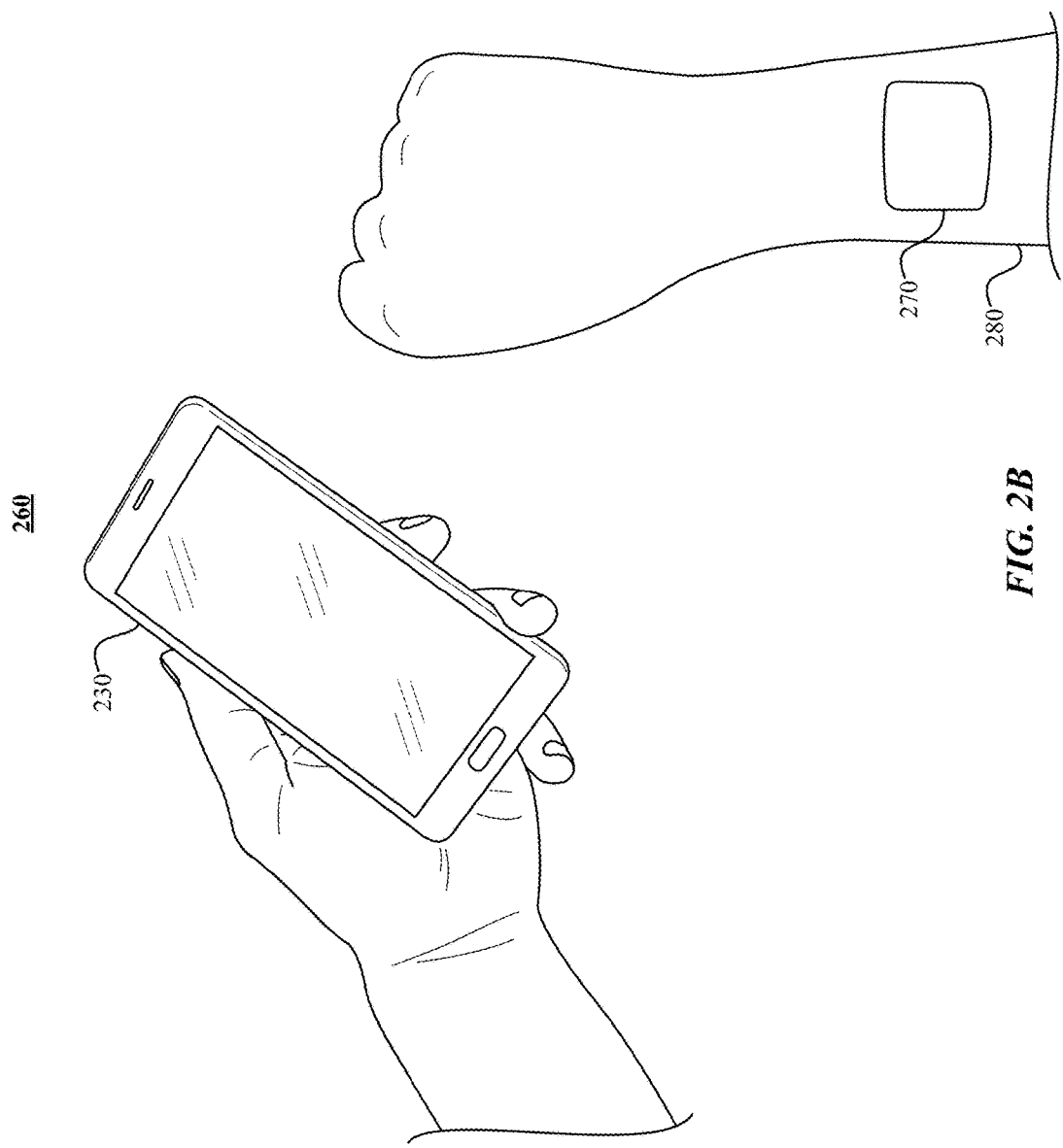
FIG. 2B illustrates another example health monitoring system including systems and devices according to particular embodiments.

FIG. 2A illustrates an example health monitoring system 200 including systems and devices according to particular embodiments, and FIG. 2B illustrates another example health monitoring system 270 including systems and devices according to particular embodiments. In particular embodiments, as shown in FIG. 2A, health monitoring system 200 may include a health monitoring device 210 (e.g., positioned on user wrist 220) and a mobile electronic device 230. Health monitoring device 210 may be a wearable electronic device (e.g., a device of client system 120) that can be worn on a portion of the user's body, such as an arm, wrist, finger, leg, ankle, toe, torso, neck, head, any other suitable portion of the body, or any combination thereof Health monitoring device 210 may include a user interface 240, which may include a watch-like user interface in addition to one or more applications 250 (e.g., a weather application, an exercise application, a chat application, etc.). In particular embodiments, as shown in FIG. 2B, health monitoring system may include a health monitoring patch 270 (e.g., positioned on user arm 280) and mobile electronic device 230. Similar to health monitoring device 210, health monitoring patch 270 may be adhered to a portion of the user's body, such as an arm, wrist, leg, ankle, torso, neck, head, any other suitable portion of the body, or any combination thereof.

In particular embodiments, health monitoring device 210 and/or health monitoring patch 270 may connect to mobile electronic device 230 directly or via network 130, which may facilitate interaction between and/or transfer of data between health monitoring device 210 and mobile electronic device 230 and/or health monitoring patch 270. In particular embodiments, mobile electronic device 230 may be a smartphone-like device. Health monitoring device 210, health monitoring patch 270, and mobile electronic device 230 may be connected to network 130, servers 140, data stores 150, or any combination thereof. Data (e.g., heart rate, stress level, sleep time, emotional state, etc.) may be stored on health monitoring device 210, health monitoring patch 270, mobile electronic device 230, other client systems 120, data stores 150, other suitable databases, or any combination thereof. In addition, the processing of the data and computations of particular algorithms (as discussed below) may be performed by health monitoring device 210, health monitoring patch 270, mobile electronic device 230, on servers 140, by any other client system 120, other suitable devices/systems, or any combination thereof. In particular embodiments, the processing of the data and computations of particular algorithms may be performed by accessing user data, frame of reference/baseline data, medical data, other relevant data, or any combination thereof, from data stores 150 via network 130. Although this disclosure describes a health monitoring system in a particular manner, this disclosure contemplates a health monitoring system in any suitable manner and with any suitable components.

Figure 3:
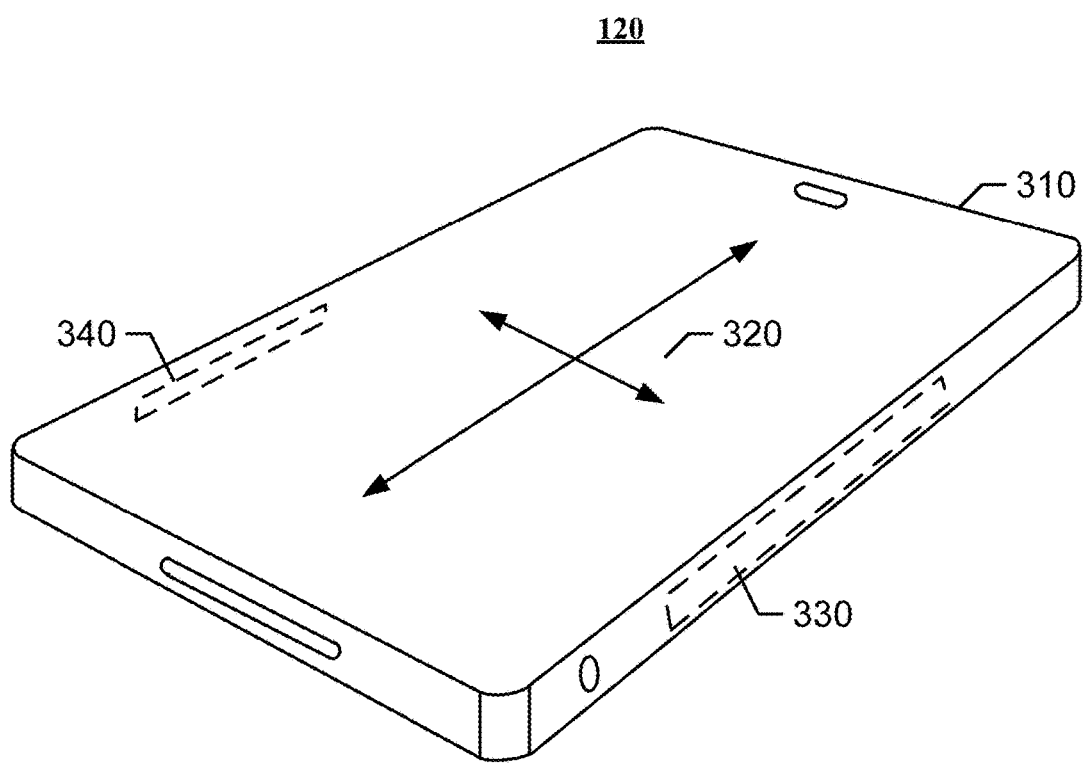
FIG. 3 illustrates an example mobile client.

FIG. 3 illustrates an example mobile client system 120 (e.g., mobile electronic device 230). This disclosure contemplates mobile client system 120 taking any suitable physical form. In particular embodiments, mobile client system 120 may be a computing system as described below. As an example and not by way of limitation, mobile client system 120 may be a single-board computer system (SBC) (such as, for example, a computer-on-module (COM) or system-on-module (SOM)), a laptop or notebook computer system, a mobile telephone, a smartphone, a personal digital assistant (PDA), a tablet computer system, or a combination of two or more of these. In particular embodiments, mobile client system 120 may have a display screen 310 and a touch sensor 320 as an input component. In the example of FIG. 3, touch sensor 320 is incorporated on a front surface (e.g., display screen 310) of mobile client system 130. Touch sensor 320 may detect the presence and location of a touch (e.g., from a finger of a user) or the proximity of an object (e.g., a stylus). In the case of capacitive touch sensors, there may be two types of electrodes: transmitting and receiving. These electrodes may be connected to a controller designed to drive the transmitting electrodes with electrical pulses and measure the changes in capacitance from the receiving electrodes caused by a touch or proximity input. In particular embodiments, a user may be presented with a user interface ("UI") of one or more applications (e.g., mobile applications) on screen display 310 of mobile client system 120, and the user may interact with the UI of each of the applications via touch sensor 320.

In the example of FIG. 3, one or more antennae 330, 340 may be incorporated into one or more sides of mobile client system 120. Antennae 330, 340 are components that convert electric current into radio waves, and vice versa. During transmission of signals, a transmitter applies an oscillating radio frequency (RF) electric current to terminals of antenna 330, 340, and antenna 330, 340 radiates the energy of the applied the current as electromagnetic (EM) waves. During reception of signals, antennae 330, 340 convert the power of an incoming EM wave into a voltage at the terminals of antennae 330, 340. The voltage may be transmitted to a receiver for amplification.

In particular embodiments, mobile client system 120 many include a communication component coupled to antennae 330, 340 for communicating with an Ethernet or other wire-based network or a wireless NIC (WNIC), wireless adapter for communicating with a wireless network, such as for example a WI-FI network or modem for communicating with a cellular network, such third generation mobile telecommunications (3G), or Long Term Evolution (LTE) network. This disclosure contemplates any suitable network and any suitable communication component for it. As an example and not by way of limitation, mobile client system 120 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As another example, mobile client system 300 may communicate with a wireless PAN (WPAN) (such as, for example, a BLUETOOTH WPAN), a WI-FI network, a WI-MAX network, a cellular telephone network (such as, for example, a Global System for Mobile Communications (GSM), 3G, or LTE network), or other suitable wireless network or a combination of two or more of these. Mobile client system 120 may include any suitable communication component for any of these networks, where appropriate.

In particular embodiments, the communication component coupled to antennae 330, 340 of mobile client system 120 may be configured to determine location data based on global positioning system (GPS) signals, cellular triangulation, wireless hotspots, or any suitable methods for determining location data. In particular embodiments, the location service of mobile client system 120 may use one or more methods of location determination, such as for example, using the location of one or more cellular towers, crowd-sourced location information associated with a WI-FI hotspot, or a GPS function of mobile client system 120. As an example and not by way of limitation, the application may use GPS data as the primary source of location information depending at least in part on whether mobile client system 120 is able to acquire GPS data within a pre-determined period of time. As another example, if mobile client system 120 is unable to acquire the GPS data within the pre-determined sampling duration, the application may use the location determined using one or more cellular towers or WI-FI hotspots. Although this disclosure describes a location service using particular methods of location determination, this disclosure contemplates a location service using any suitable method or combination of methods of location detection.

Figure 4A:
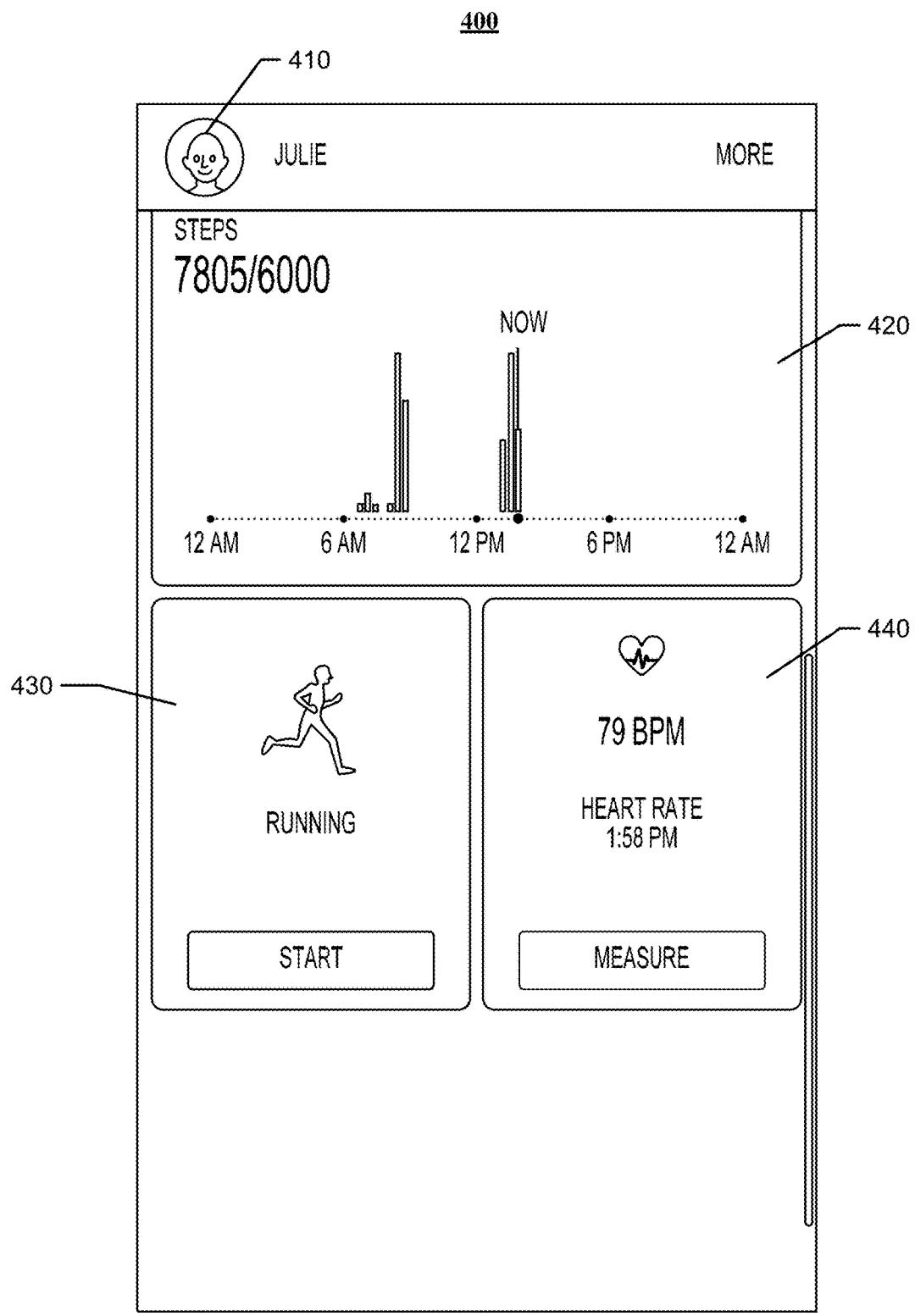
FIGS. 4A and 4B illustrate example user interfaces according to particular embodiments of the invention.
Figure 4B:
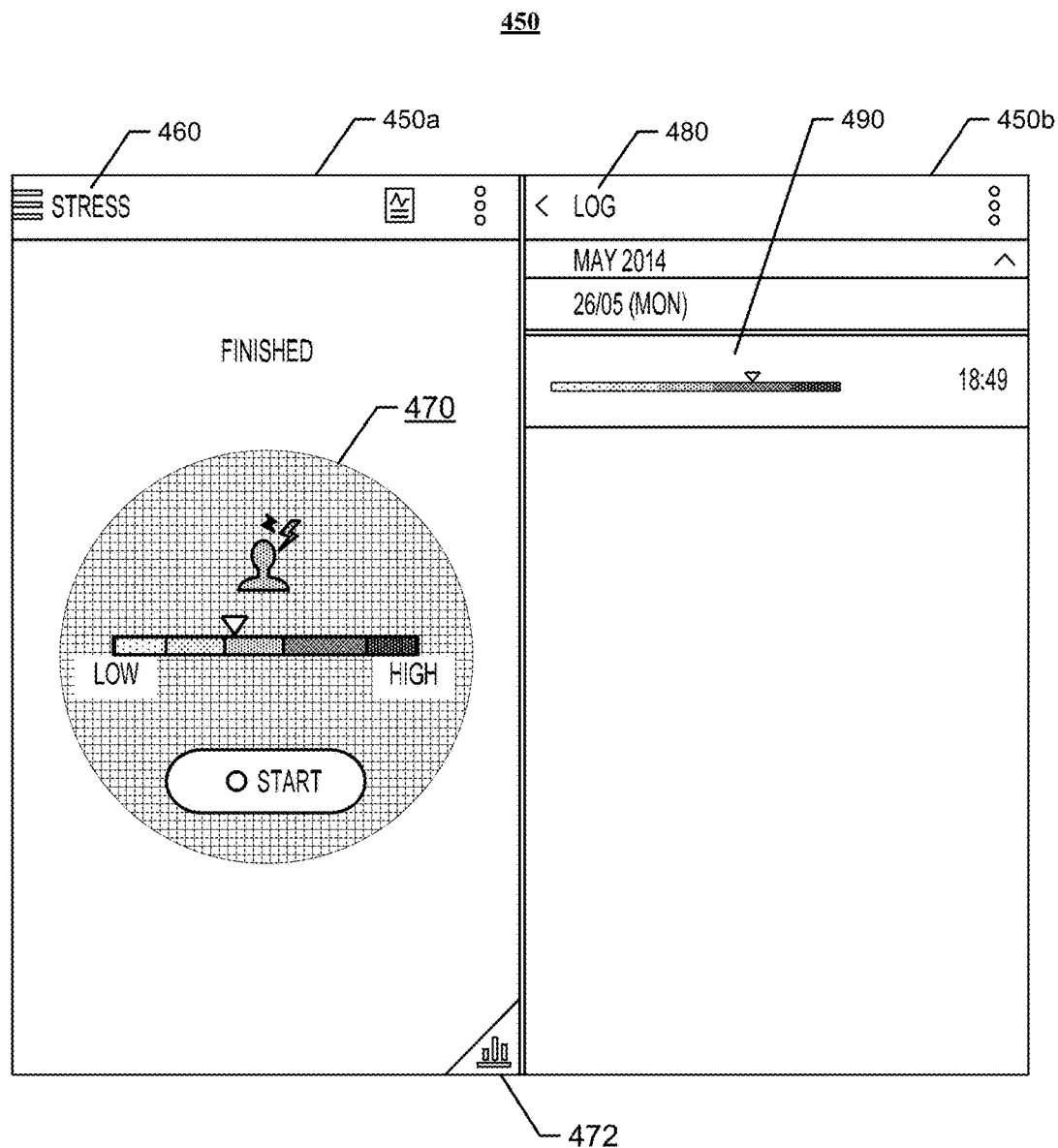

FIGS. 4A and 4B illustrate example user interfaces according to particular embodiments of the invention. FIG. 4A illustrates an example user interface 400 showing types of information for a user 410 ("Julie"). In a first portion 420, user interface 400 shows information on the number of steps user 410 has taken during particular hours of a particular day. In a second portion 430, user interface 400 shows information on an activity (e.g., running) that may be used by the user to collect user information. In a third portion 440, user interface 400 shows information on current user measurements (e.g., a heart rate). FIG. 4B illustrates an example user interface 450 for a stress determination that includes a first user interface 450*a* and a second user interface 450*b*. First user interface 450*a* includes a category (e.g., "stress" 460) describing the information illustrated, and a graphical representation 470 of a stress level associated with the user. First user interface 450*a* also includes a chart option 472, which changes the user interface 450 to second user interface 450*a*. Second user interface 450*a* shows a log 480 of past stress level information 490 save for the user. In particular embodiments, other stress-related information may be provided to the user (or an option may be provided to the user for collecting particular types of stress-related information) via user interface 450. Although this disclosure describes example user interface for a health monitoring system in a particular manner, this disclosure contemplates providing user interfaces for a health monitoring system in any suitable manner to provide information to the user.

Stress Detection

As discussed above, stress is considered to be one of the largest contributors to various health problems. Stress management techniques tend to be inaccurate and instable, especially in the presence of noise. Accordingly, particular embodiments discussed below address these issues by providing an HRV algorithm applicable to detecting stress as well as measuring relaxation that is based on an analysis of SVB. SVB is one concept behind psychophysiological description of stress, and the analysis of SVB is based on a ratio approach that provides HRV (e.g., stress) values in terms of a percentage deviation from normal. This approach is linear in nature, which makes it very stable to noise (e.g., which tends to be nonlinear in nature). In addition, this approach is highly customizable to address the unique needs of the user, other users, or medical professionals.

Stress management techniques that work by measuring the activities/arousal of ANS, where high arousal is considered a sign of stress, tend to focus on the parasympathetic nervous system (PSNS) rather than the sympathetic nervous system (SNS). However, this may be problematic because an increase in the PSNS may not necessarily imply a decrease in the SNS, and thus, analysis of the SNS may be as useful as the analysis of the PSNS. In contrast, as discussed in more detail below, the methods based on analyzing SVB looks at the homeostatic equilibrium where the sympathetic outflow and PSNS (e.g., vagal nerve) outflow are in stable balance. Accordingly, SVB, and hence stress, may be determined by analyzing relative dominance and balance between the SNS and PSNS (e.g., between parasympathetic outflow and sympathetic outflow).

A problem also arises in that both the SNS and PSNS are not easily quantified and compared because they have no accepted unit of quantification, which leads to numbers that are hard to interpret and evaluate. The analysis of SVB described treats the SNS and PSNS with equal weightage (e.g., because they are both useful in analyzing the ANS arousal) and uses the most elementary unit of HRV, which is not heart rate (HR) but RR-deltas (e.g., RR interval differences between successive heart beats). In addition, the profusion of inexpensive, user-friendly, wearable sensors makes it easier to collect data and analyze SVB using a large volume of data in real-life settings and in real-time. In particular embodiments, to determine SVB, stress is defined as increased dominance of the SNS in the RR-delta histogram $H_t$ of test data t, and the data points on the histogram correspond to the difference between a length of adjacent RR intervals in a set of test data. In particular embodiments, the methods described below computes only a ratio of a number of events relatively mapped to SNS with a number of events relatively mapped to PSNS. Divisions between SNS and PSNS, their individual range for the given user, can be labeled using methods such as RMSSD, SDNN, pNN50, etc. In addition, irrespective of which measurement method is chosen, the data points that are computed are dimensionless. As an example and not by way of limitation, given a baseline SVB of the user, and an RR-delta histogram $H_t$, the SVB may be computed as a median of all RR-deltas, a mean value of all RR-deltas, 50% of RMSSD, computed over $H_t$, 50% of SDNn, computed over $H_t$, other relevant values, or any combination thereof.

In particular embodiments, given a baseline data histogram $H_b$, test data histogram $H_t$, and an algorithm $ALG_X$ to determine a marker of the ANS activity in test data histogram $H_t$ (e.g., an algorithm that can compute HRV over the histogram, or count number of instances of RR-deltas in different segments of the histogram computation algorithm), the method comprises (1) computing SVB from baseline data histogram $H_b$, (2) determining segment $H_{Lt}$ and segment $H_{Rt}$ the segments in test data histogram $H_t$ respectively to the left and right of SVB point, (3) using algorithm $ALG_X$, computing the desired measure of RR-variability (a direct effect of ANS arousal) in both the left segment $H_{Lt}$ and the right segment $H_{Rt}$, and (4) computing the HRV as a ratio of the algorithm $ALG_X$ measure of RR-variability in the left segment ($ALG_X (H_{LT})$) with the measure of RR-variability in the right segment ($ALG_X (H_{RT})$), or from the total histogram $ALG_X (H_T)$. Then, for easy standardization or comparison between different users, the HRV zones may be pre-defined as: 0-20 being representative of "very stressed," 20-40 being representative of "stressed," 40-60 being representative of "normal," 60-80 being representative of "relaxed," and 80-100 being representative of "very relaxed."

Figure 5A:
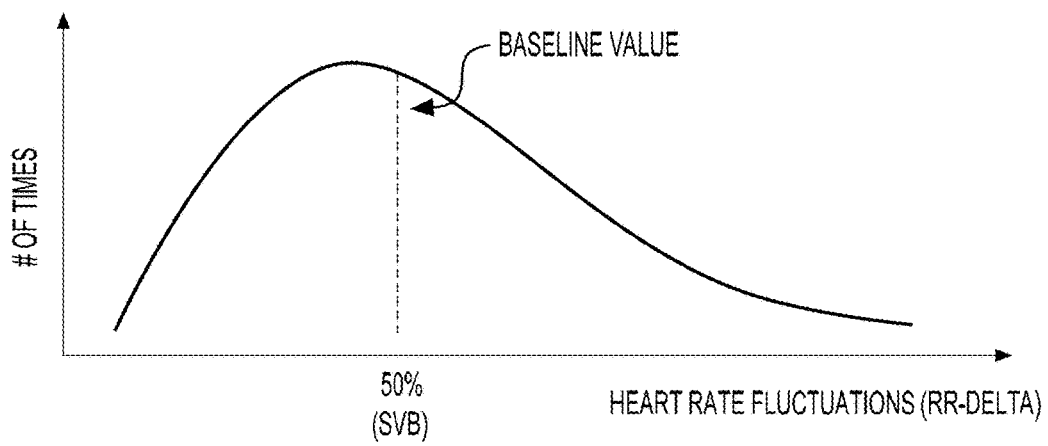
FIG. 5A illustrates an example of a baseline data histogram.

FIG. 5A illustrates an example of baseline data histogram 500. As shown in FIG. 5A, an x-axis of baseline data histogram 500 corresponds to heart rate fluctuations (e.g., RR-deltas), and a y-axis of baseline data histogram 500 corresponds to a number of times of the heart rate fluctuations for a set of baseline data. The SVB point is the point of 50:50 distribution of baseline data histogram 500 such that 50% of the data points of the set of baseline data are to the left of the SVB and 50% of the data points of the set of baseline data are to the right of the SVB. Using baseline data histogram 500, the SVB may be computed and may correspond to an HRV zone representative of a "normal" (e.g., non-stressed) state.

Figure 5B:
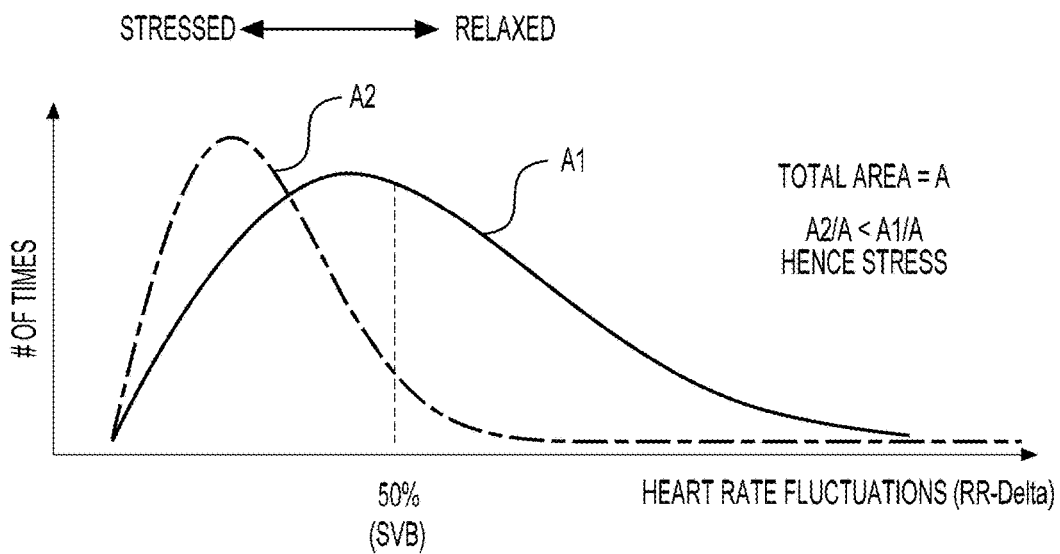
FIG. 5B illustrates an example of a test data histogram in which a sympathovagal balance is shifted to the left.
Figure 5C:
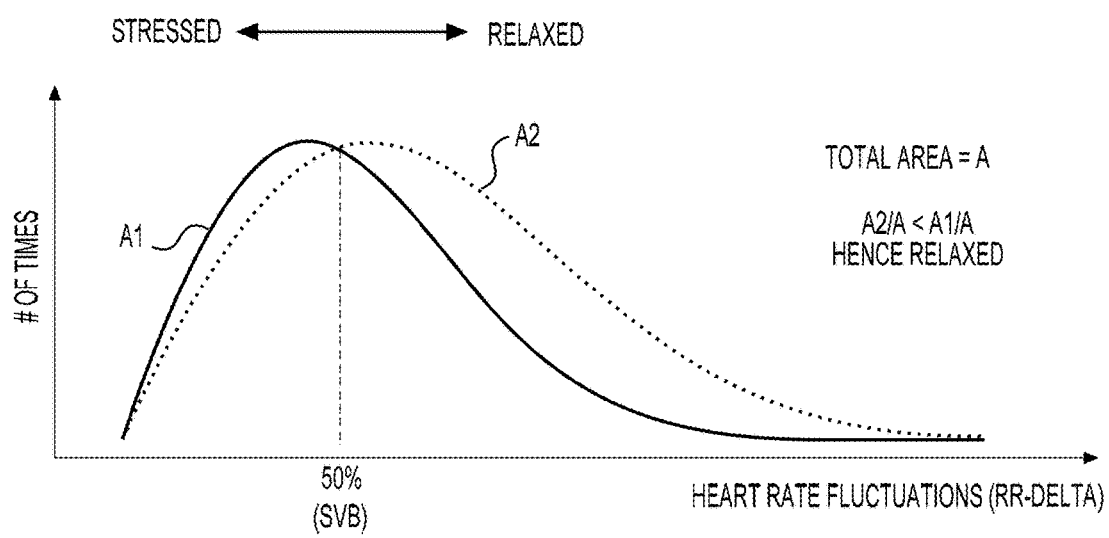
FIG. 5C illustrates an example of a test data histogram in which a sympathovagal balance is shifted to the right.

FIG. 5B illustrates an example of a test data histogram 510 in which the SVB is shifted to the left, and FIG. 5C illustrates an example of a test data histogram 520 in which the SVB is shifted to the right. As shown in FIG. 5B, similar to FIG. 5A, an x-axis of test data histogram 510 corresponds to heart rate fluctuations (e.g., RR-deltas), and a y-axis of test data histogram 510 corresponds to a number of times of the heart rate fluctuations for a set of test data. When the heart rate fluctuations for the set of test data on average results in the shifting of balance from histogram A1 (e.g., corresponding to the baseline data) toward a left direction to histogram A2, or in other words, the number of measurements of heart rate fluctuations of histogram A2 that are to the left of the SVB (e.g., as determined based on the baseline data) are greater than the number of measurements of heart rate fluctuations of histogram A2 that are to the right of the SVB, then it is determined that the user's state corresponds to a HRV zone representative of a "stressed" state. Explained another way, as shown in FIG. 5B, given a total area A, the area of A2 over A (e.g., the area under the curve of A2) is determined to be less than the area of A1 over A (e.g., the area under the curve of A1) when the histogram shifts to the left and it is determined that the user's state corresponds to a HRV zone representative of a "stressed" state.

On the other hand, as shown in FIG. 5C, similar to FIG. 5A, an x-axis of test data histogram 520 corresponds to heart rate fluctuations (e.g., RR-deltas), and a y-axis of test data histogram 520 corresponds to a number of times of the heart rate fluctuations for a set of test data. When the heart rate fluctuations for the set of test data on average results in the shifting of balance from histogram A1 (e.g., corresponding to the baseline data) toward a right direction to histogram A2, or in other words, the number of measurements of heart rate fluctuations of histogram A2 that are to the right of the SVB (e.g., as determined based on the baseline data) are greater than the number of measurements of heart rate fluctuations of histogram A2 that are to the left of the SVB, then it is determined that the user's state corresponds to a HRV zone representative of a "relaxed" state. Explained another way, as shown in FIG. 5C, given a total area A, the area of A2 over A (e.g., the area under the curve of A2) is determined to be greater than the area of A1 over A (e.g., the area under the curve of A1) when the histogram shifts to the right and it is determined that the user's state corresponds to a HRV zone representative of a "relaxed" state.

Particular embodiments of this embodiment depend on creatively dividing the RR-delta histogram, $H_T$, based on the notion of contextually appropriate SVB. As an example and not by way of limitation, if the context is all the cyclic components responsible for variability in the period of recording, then the ratio for SVB may be evaluated via the SDNN(H) model.

In particular embodiments, a length of a buffer of the RR-delta data that is used to populate the histogram need not be limited to some fixed size during the computation of stress. Since the algorithm provides a measure of SVB, even if a longer length of data is used, above a certain minimum length, the SVB would nonetheless be meaningfully depicted even though the nature of the stress plot may be somewhat different. As such, the buffer length may be varied based on the requirements of accuracy, stability, or any other attribute where a variable length may be beneficial.

In particular embodiments, using multiple other types of sensors or biomarkers not solely focused on HR analysis may enrich the algorithms even further. As an example and not by way of limitation, data regarding the nature of the blood flow from PPG, or ECG features, galvanic skin response (GSR) measurements, EEG characteristics, blood pressure such as in pulse wave transit time (PWTT) may be used to give additional information about ANS. This information may be used to further inform or adjust the proposed HRV algorithm. As an example and not by way of limitation, the above-mentioned variable length buffer may be adjusted using such information. In addition, the final stress computed may be considered as a composite of ANS quantification provided by the proposed HRV algorithm and other markers from sensors such as PPG, ECG, EEG, GSR, etc. Such data fusion may be initiated per the user's choice, for example, during the times when the stress computed exceeds a certain threshold so that before sounding an alarm, the HRV computations may be further reviewed or adjusted. Utilizing multiple types of measurements may be considered all at once, or may be considered as needed (e.g., one by one). As an example and not by way of limitation, HRV data and blood flow data may be collected, and then based on these sets of data, a stress level may be estimated. As another example and not by way of limitation, HRV data may collected and the stress level may be determined. If the stress level is above or below a threshold, blood flow data may be used to confirm or adjust the stress level estimate. As yet another example and not by way of limitation, different sensor measurements may be dynamically chosen to be used for stress estimation based on the noise level of the sensor measurement (e.g., if blood flow data is determined to be unreliable, health monitoring device 210 may select to omit using blood flow data).

In addition, the above-discussed algorithms have the benefit of high flexibility. In particular embodiments, the algorithms may be used to provide a variety of services that may include providing the physician a warning during a panic stress episode (e.g., in which case the algorithms may compute a variety of histograms of different length so that the stress computed may be validated in as many ways as possible); warning a driver during a high speed drive under high stress (e.g., when the histogram computed is of the minimal possible length so that a warning can be given as early as possible); alerting a student during an episode of severe stress while at school (e.g., where the stress computed has features expected to be present during an exam such as a stress continuously rising throughout the exam or at school, or to locate unusually severe episodes such as when the HRV is very high while the HR has dipped very low compared to the baseline), etc. Thus, given the flexibility inherent in the stress computing/warning algorithms and a wide variety of applications in which such information may useful, one can easily adjust the various steps required in computing of psychophysiological stress or even the SVB per the proposed algorithm may be easily adjusted (e.g., automatically by health monitoring device 210, by the user, by a third party, etc.).

Moreover, the above-discussed algorithms may facilitate a number of services. As an example and not by way of limitation, example services may include integration with a car, patches worn by the user (e.g., as shown in FIG. 2B), interfacing with a virtual reality device or game console, etc. In the last situation, the virtual reality device or game console may adjust its content based on the user's stress level (e.g., adjust the dram level of the soundtrack or adjust the game's difficulty).

Figure 6:
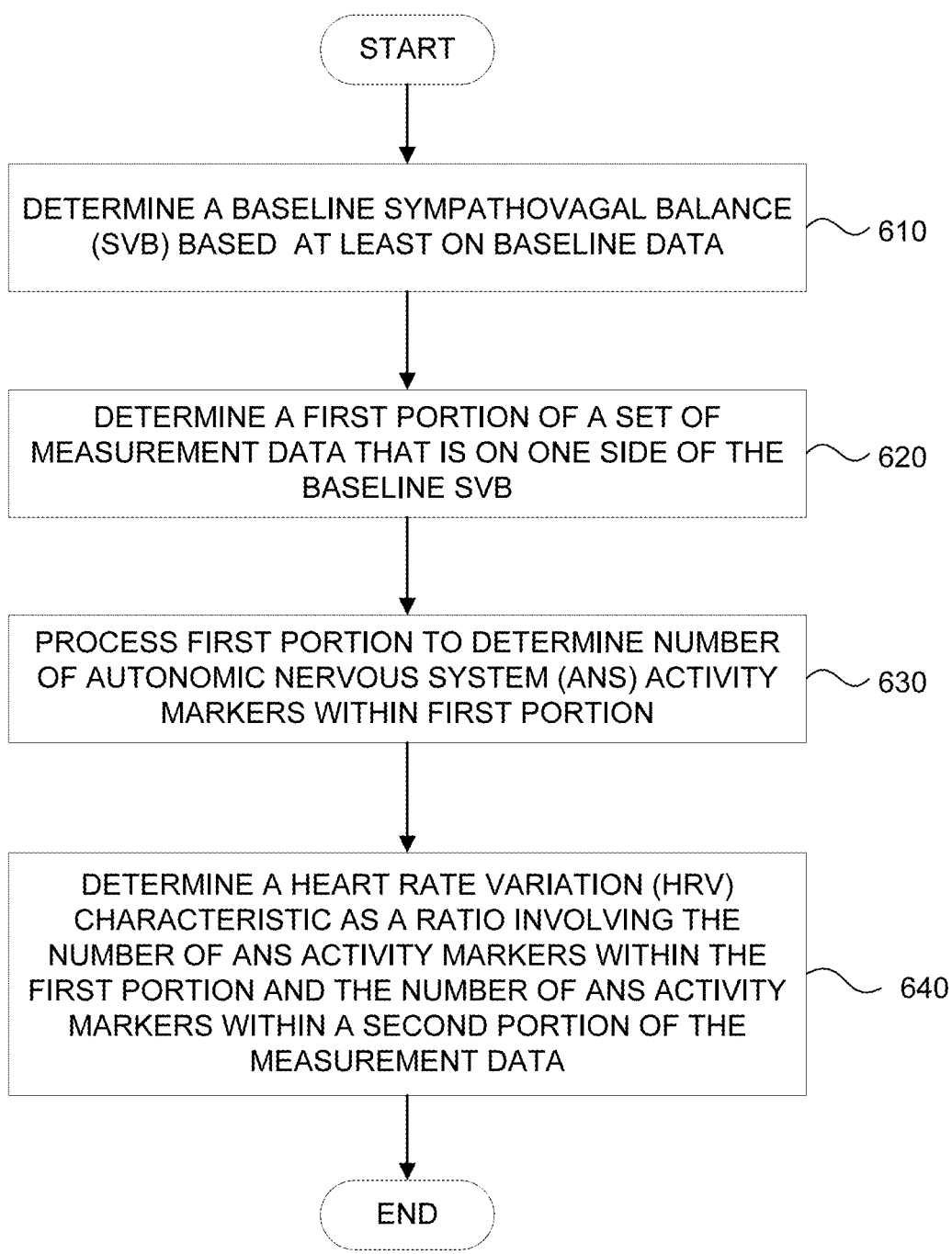
FIG. 6 illustrates an example method for stress detection.

FIG. 6 illustrates an example method 600 for stress detection. The example method 600 may be deployed on one or more electronic devices, such as a mobile phone, tablet computer, smart watch, head-mounted device, body-harness-secured devices, and the like mobile devices, wearable devices, fixed-location computing devices, and/or network or cloud deployed systems, having suitable communication, processing, sensing facilities, other suitable devices, or any combination thereof. In particular embodiments, measurement data may include variations in the beat to beat heart rate (RR-delta), skin conductance, frequency components inherent in electrical activity on scalp, inhalation and exhalation patterns, etc. As an example and not by way of limitation, the measurement data can be measured using heart rate measurement sensors such as electrocardiogram (ECG), electrodermal analysis sensors, EEG headset, respiration sensors, other suitable sensors, or any combination thereof. As another example and not by way of limitation, a processor or circuitry may embody the method (e.g., one or more computer processors may be communicatively coupled to a data storage device that stores instructions executable by the one or more computer processors to perform operations of example method 600 for stress detection).

In particular embodiments, the method 600 may be performed by health monitoring system 200. The method 600 may be for the purpose of determining a stress level of a user based on a SVB value calculated from a set of measurement data. The method 600 begins at step 610, where health monitoring system 200 may determine a baseline SVB based at least on baseline data. At step 620, health monitoring system 200 may determine a first portion of a set of measurement data that is on one side of the baseline SVB. At step 630, health monitoring system 200 may process the first portion of the set of measurement data to determine a number of ANS activity markers within the first portion. Then, at step 640, health monitoring system 200 may determine a HRV characteristic as a ratio involving the number of ANS activity markers within the first portion and the number of ANS activity markers within a second portion of the measurement data. The first and second portions of the set of measurement data are selected based on a baseline SVB value (e.g., a user-specific baseline SVB value) that divides a histogram representation of the set of measurement data into the first and second portions. Then, the method 600 may terminate. Alternatively, the method 600 may determine the stress level of the user based on the HRV characteristic prior to terminating.

In particular embodiments, prior to determining the HRV characteristic, the method 600 may determine a baseline SVB value based at least on user-specific baseline data, determine the first portion of the set of measurement data that is on a first side of the SVB, and then process the first portion of the set of measurement data to determine the number of ANS activity markers within the first portion. The second portion of the set of measurement data may include the set of measurement data less the first portion of the set of measurement data. In particular embodiments, the method 600 may process the second portion of the set of measurement data to determine the number of ANS activity markers within the second portion.

In particular embodiments, the method 600 may receive, from a sensor of an electronic device of the user, the set of measurement data, and generate, based on the set of measurement data, a histogram of the ANS activity markers. The histogram of the ANS activity markers may be divided into the first and second portions such that the number of ANS activity markers in the first portion substantially equal the number of ANS activity markers in the second portion. The user-specific baseline SVB value may correspond to a position on the histogram where the number of ANS activity markers in the first portion substantially equal the number of ANS activity markers in the second portion. In addition, the electronic device may include at least a wearable electronic device, and the histogram of the ANS activity markers may be determined by the wearable electronic device. The user-specific baseline SVB value may be determined by the electronic device. In addition, the stress level of the user may be determined by comparing the number of number of ANS activity markers in the first portion with the number of ANS activity markers in the second portion.

In particular embodiments, the ANS activity markers may include one or more SNS activity markers and one or more PSNS activity markers. The ANS activity markers within the first portion of the set of measurement data may include the one or more SNS activity markers, and the ANS activity markers within the second portion of the set of measurement data may include the one or more PSNS activity markers. The HRV characteristic may be determined based on a ratio involving a number of the SNS activity markers to a number of the PSNS activity markers. In addition, the HRV characteristic may be determined based on the ratio of the number of the SNS activity markers to the number of the PSNS activity markers being approximately 50:50.

In particular embodiments, the ANS activity markers may contribute to the first and second portions based on a first probabilistic weight corresponding to the first portion and a second probabilistic weight corresponding to the second portion. Each of the ANS activity markers may contribute to sympathetic nervous system (SNS) activity based on the first probabilistic weight and to parasympathetic nervous system (PSNS) activity based on the second probabilistic weight. In addition, the user-specific baseline SVB value may correspond to a range of SVB values, and the stress level of the user may correspond to a range of stress-level values.

Particular embodiments may repeat one or more steps of the method of FIG. 6, where appropriate. Although this disclosure describes and illustrates particular steps of the method of FIG. 6 as occurring in a particular order, this disclosure contemplates any suitable steps of the method of FIG. 6 occurring in any suitable order. Moreover, although this disclosure describes and illustrates an example method for stress detection including the particular steps of the method of FIG. 6, this disclosure contemplates any suitable method for stress detection including any suitable steps, which may include all, some, or none of the steps of the method of FIG. 6, where appropriate. Furthermore, although this disclosure describes and illustrates particular components, devices, or systems carrying out particular steps of the method of FIG. 6, this disclosure contemplates any suitable combination of any suitable components, devices, or systems carrying out any suitable steps of the method of FIG. 6.

Figure 7A:
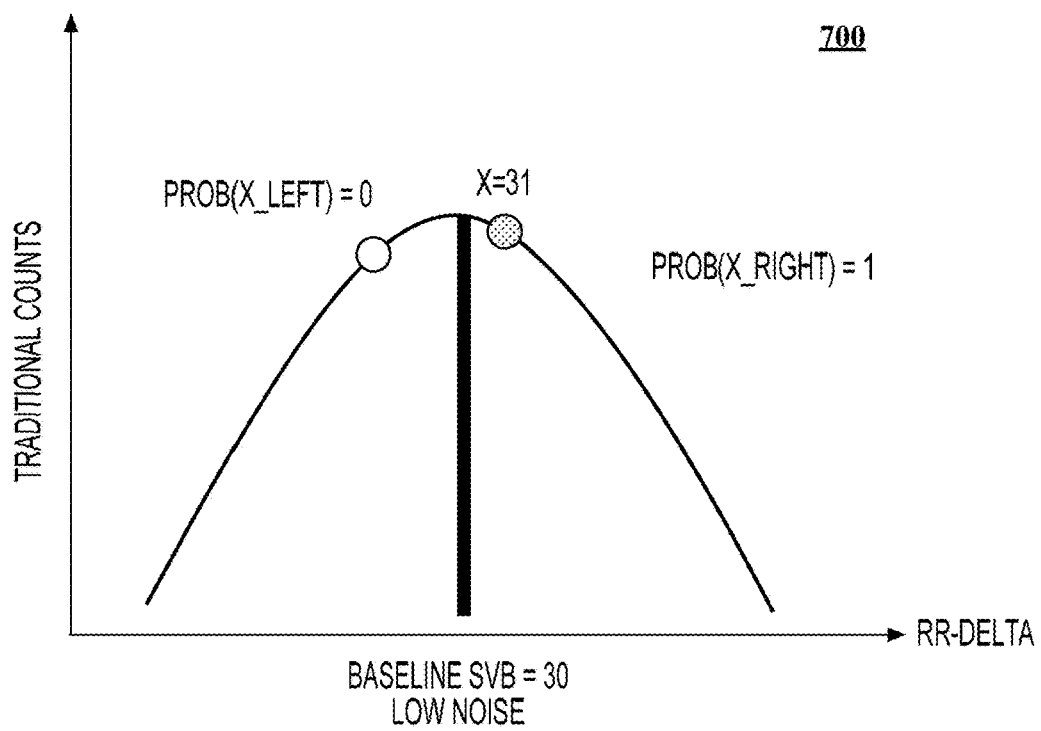
FIG. 7A illustrates a probabilistic approach for low noise in the data measurements.
Figure 7B:
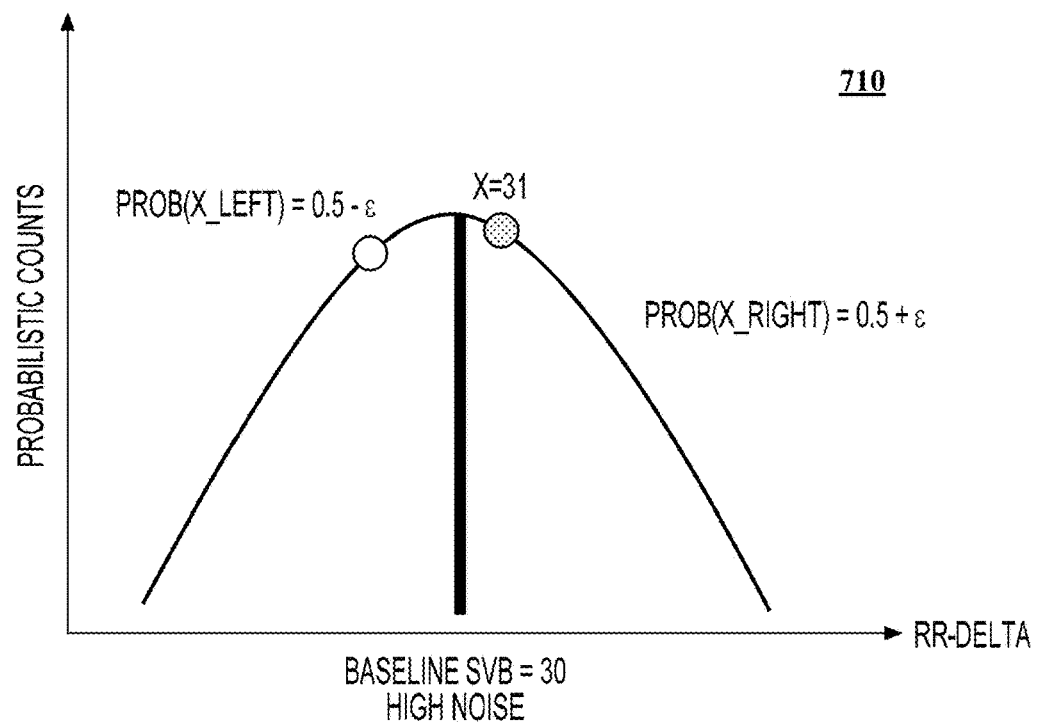
FIG. 7B illustrates a probabilistic approach for high noise in the data measurements.

In particular embodiments, a probabilistic approach may be desirable based on the limitations of sensors. As an example and not by way of limitation, a 1 KHz sampling rate may be required for ANS quantification, but this may give rise to a number of problems because many sensors only have a 100 Hz sampling rate, and thus 10 millisecond "bins." In particular embodiments, data points close to the median may be assigned fractional presence in the other side of the histogram. As an example and not by way of limitation, assume that a data point "x" has been assigned a position in bin number "i," where the first bin is labeled to be bin number 1. Based on the bin size, a position adjacent to the baseline in the histogram may have a significant likelihood of being present in the other side of the histogram. FIG. 7A illustrates a probabilistic approach for low noise in the data measurements, and FIG. 7B illustrates a probabilistic approach for high noise in the data measurements. As shown in FIG. 7A and FIG. 7B, an x-axis of histogram 700 (or histogram 710) corresponds to heart rate fluctuations (e.g., RR-deltas), and a y-axis of histogram 700 (or histogram 710) corresponds to a number of times of the heart rate fluctuations for a set of data. As an example, as shown in FIG. 7A, the baseline SVB is equal to 30, and for a data point x at 31, example assignments for the left side and right side of histogram 700 may include Prob(x_left)=0, and Prob(x_right)=1.

In particular embodiments, this assignment is a function of the bin size as well as noise inherent in the signal. Thus, given a particular bin size $\alpha$, for Noise_x($\beta_{t,j}$) at the $j^{th}$ position in a time series $\beta_t$, and RR-interval computation approach $\varphi_k$, it may be determined that:

$$\text{Prob}(x\_\text{left}) \neq 0, \text{ where Prob}(x\_\text{left}) = f(\text{Noise}\_x(\beta_{t,j}), \alpha, \varphi_k)$$

In general, the probability of a point x may be quantified not just in the left or right portions around the baseline, but also at each bin in the histogram. This may allow for the baseline SVB to be updated, which is not possible if the quantification is only dependent on the probabilistic position of the point on either side of the baseline. As an example and not by way of limitation, suppose there are five points on each side of the baseline SRV of 30, where the bin size is 1 millisecond. As shown in FIG. 7B, in the situation where the next point x has an RR-delta of 31 and the noise in the time series is fairly high, then the method will assign a fractional weight (presence) of 0.5 on either side of the baseline. This is due to the high uncertainty introduced in the actual RR-delta computations. Accordingly, example assignments for the left side and right side of histogram 710 may include: Prob(x_left)=0.5−ε, and Prob(x_right)=0.5+ε, where ε is a function of noise and distance of x from the baseline SVB, which may be approximated by one-sided Gaussian or the polynomial that best fits the histogram envelope. In addition, the quantification of noise for robust measurements of Noise_x($\beta_{t,j}$) are discussed in more detail below.

Figure 7C:
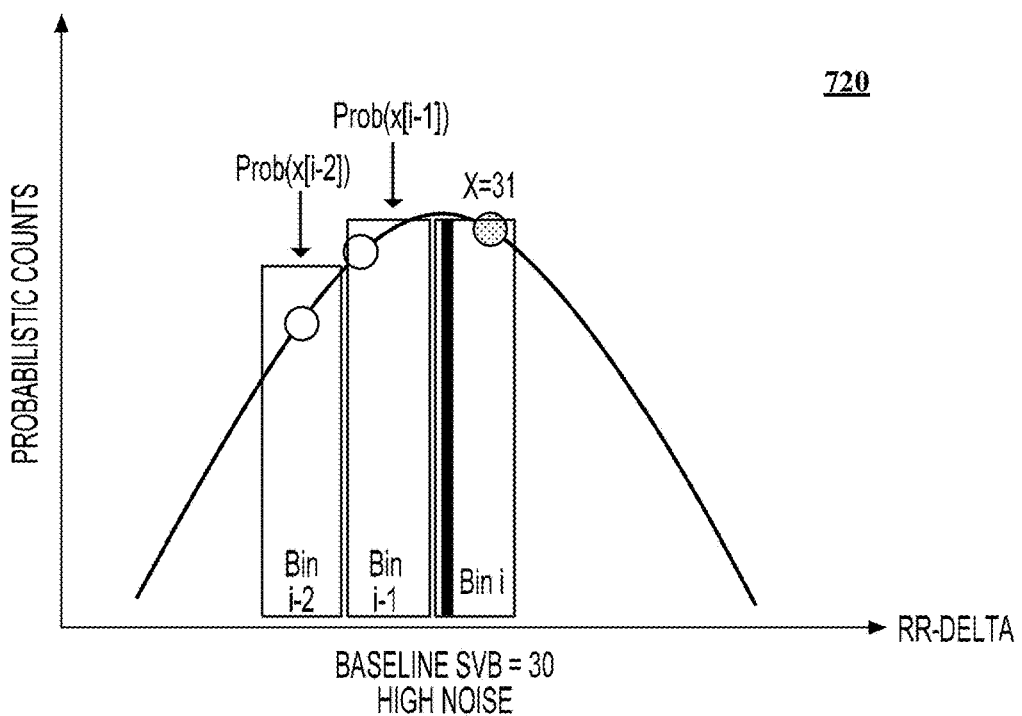
FIG. 7C illustrates a probabilistic approach for updating a baseline SVB based on a probabilistic determination.
Figure 7D:
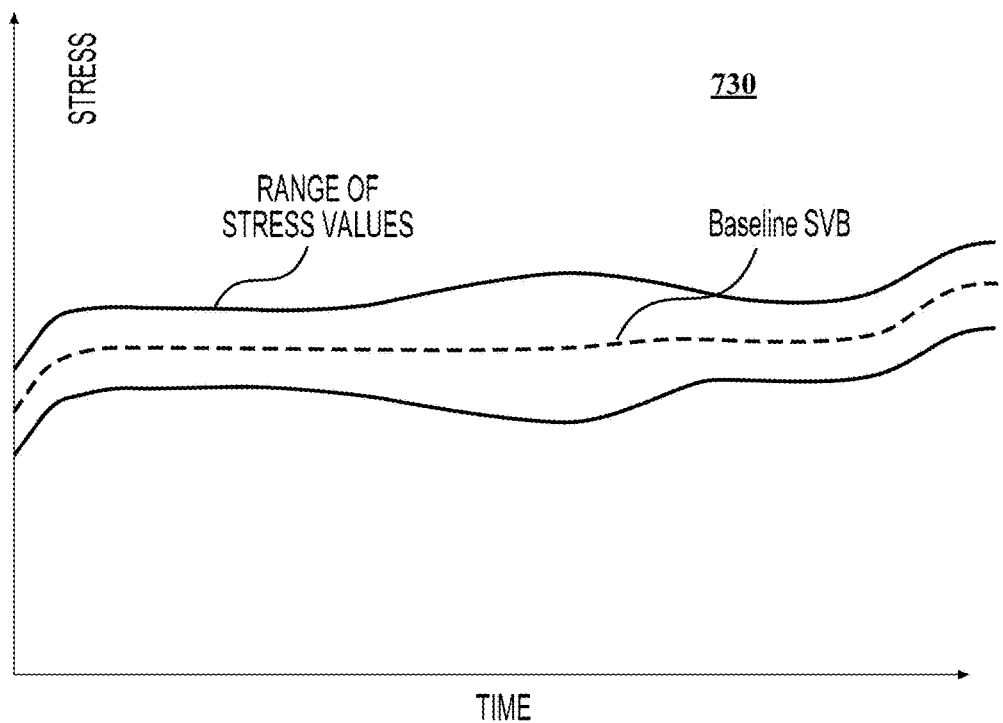
FIG. 7D illustrates a graph that shows a range of stress values over time for a user.

FIG. 7C illustrates a probabilistic approach for updating a baseline SVB based on a probabilistic determination. As shown in FIG. 7C, an x-axis of histogram 720 corresponds to heart rate fluctuations (e.g., RR-deltas), and a y-axis of histogram 720 corresponds to a number of times of the heart rate fluctuations for a set of data. In particular embodiments, the probability Prob(x[i±h]) of point x being in another bin, at a distance of h from the original bin i, increases in presence of greater noise. As an example and not by way of limitation, as shown in FIG. 7C, the probability associated with bin i−1 is Prob(x[i−1]), and the probability associated with bin i−2 is Prob(x[i−2]). In addition, this probability may be different in two different users even in the presence of the same extent of noise due to the inherent stochasticity in their HRV signal. In particular embodiments, health monitoring system 200 may collect signal data under normal conditions, as indicated by the user, as well as for a short period, such as few minutes, under some expected or reasonable noisy conditions. This may be helpful in providing a measure of the probability of the signal data under different bins. Once the noise is quantified, health monitoring system 200 may obtain a measure of the probability Prob(x[i±h]) of point x being in another bin at a distance of h from the original bin number i. In particular embodiments, a variety of simulations may be carried out to determine the behavior of signal data under noisy conditions where the noise need not be introduced by actual physical movements, but may be introduced synthetically in the baseline SVB signal to provide a database for computing the probabilistic models and hence a more accurate SVB measure. FIG. 7D illustrates a graph 730 that shows a range of stress values over time for a user. As shown in FIG. 7D, stress values associated with the baseline SVB may be corrupted by noisy signals, and thus health monitoring system 200 may obtain a measurement of SVB that corresponds to a range of stress values. The graph can be displayed within the user interface 450 of FIG. 4B in accordance with an example embodiment.

Finally, note that in an example method the ΔRR values are computed with reference to multiple key PPG features. For example, a separate ΔRR can be computed each from trough, peak, and zero-crossing features. Or, a separate ΔRR can also be computed from other signal processing techniques such as mutual information (as detailed later). The final ΔRR value can then be selected based on the quality of the given signal feature as well as physiological factors. The quality of the signal feature can be judged by examining the noise around that feature. For example, if the signal around supposed peak of the PPG is found to be very noisy as compared to the signal around the trough, then ΔRR selected from PPG peak is given lower priority as compared to the ΔRR computed from PPG trough. In an example aspect, among others, the physiological reasoning behind selecting or weighting the ΔRR is primarily driven by the consideration that the body tries to maintain the stress homeostasis.

Thus, given a large discrepancy in ΔRR from multiple features, the ΔRR that minimizes the change in stress may be relatively accurate. This may have a large effect when different ΔRR fall on different sides of the baseline. In presence of a tie, in accordance with an example embodiment, the method selects the zero crossing based RR, whose accuracy may be justified by the rapidly rising signal at the zero crossing point. Hence, even a moderately large error in estimating the zero in the signal may not translate to a large error in the time stamp. This nature of zero crossings is a result of the blood flow pattern in which the blood volume rises very rapidly during the systolic phase (the zero crossing lies in the systolic phase).

Weighted Left-Shift and Histogram Profile Refinement

Figure 8:
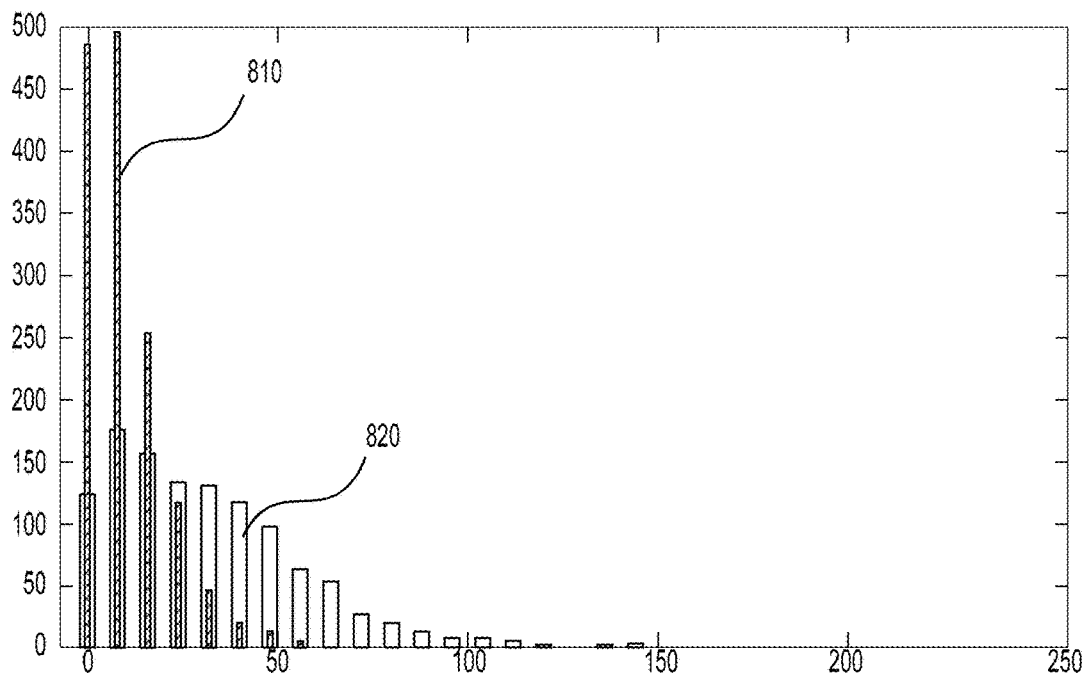
FIG. 8 illustrates an example of a histogram exhibiting left shift from a baseline state.

In particular embodiments, most HRV-based algorithms to detect stress may simply be measuring the extent to which the histogram of successive beat-to-beat RR-deltas has shifted to the left (e.g., to a more stressed state). In particular embodiments, smart left-shift algorithms are similar to the SVB computation approach, but with the understanding that different parts of the histogram may have varying importance. In addition, since stress may correspond to a left shift of the histogram from its baseline state, this may be computed as a reduction of the scaled area of the histogram by adjusting the area of the histogram based on the "expected weight" of different histogram regions. Since the histogram may be considered to be broken into "n" number of bins each created due to the sensors having limited sampling rates, a left shift algorithm may be created by computing a scaled area of the histogram that is reduced compared to its baseline area in presence of stress. FIG. 8 illustrates an example of a histogram 800 exhibiting left shift from a baseline state. As shown in FIG. 8, histogram 800 is shown to have shifted to a position 810 heavily favoring the left portion of the histogram from a baseline position 820.

In particular embodiments, while a traditional area of a histogram for SVB computation=$\Sigma y_i$*(width of band i), a scaled area determined based on the left shift algorithm=SA=$\Sigma y_i y_i k_i$, where $x_i$=x axis value of band i, $y_i$=total samples in band i, and $k_i$=A scaling factor for bin 'i' based on its value assessment. In particular embodiments, an expected weight of the scaled area may be, for example, calculated based on a function set by the therapist or by the user himself based on the noise profile of the signal. The pre-set bias may be corrected by giving lower probability of RR-delta instances in certain areas, if required. In addition, weights may be determined based on probability distribution which assigns instances to belong to more than one bin based on the uncertainty introduced by the extent of noise.

In particular embodiments, in computing the scaling factors, to give larger weight to the left part of the histogram, the left-most region may be assigned a lower weight if RR-delta=0 is the default assignment in the presence of noisy heartbeat-to-heartbeat variability. Higher weight to the right most region may be assigned if instances of data points are large and rare. In addition, the scaling factor may be modulated based on the accelerometer (e.g., via activity detection). In particular embodiments, the outliers in the histogram may create strong variability in the result, and thus the SVB computation may be further refined by calculating the left shift by characterizing the profile of the histogram's envelope. As shown in FIG. 8, the "envelope" may be conceptually considered to be characterized by a small number of "goal posts" (e.g., interquartile range or mode-based goal-posts). The left shift algorithm may be further refined by the rejection of certain classes of outliers. In particular embodiments, for calculating stress, these techniques try to create an appropriate desensitization of the histogram "tail" (e.g., the right-most portion of the histogram). In addition, the left shift algorithm may be further refined by using the expected performance or past historical trends, leading to an approach where the weights are assigned based on a probability distribution.

Noise Detection/Correction and Error Compensation

As discussed above, stress can contribute to various health problems, and thus accurate, robust, and meaningful measurement of psychological stress can be advantageous in the monitoring and management of health and/or wellness. Real-life bio-sensing measurements may be noisy and bio-signals derived from these measurements may be noise sensitive. For example, the source of noise may be motion artifacts, erratic and/or lose body-sensor contacts, a wide variety of ambient disturbances, other relevant noise, or any combination thereof. Such noise is highly prominent in photoplethysmogram (PPG) signals, which is a sensitive bio-signal with low tolerance for anything less than ideal collection and analysis methods. Particular embodiments discussed below pertain to methods for performing accurate biosensing of PPG signals with noisy measurements. In addition, the particular embodiments discussed below may also pertain to monitoring and analyzing other suitable bio-signals relevant to health and/or wellness with noisy measurements. In particular embodiments, these methods may help to deal with issues such as imprecise and difficult to interpret measurement algorithms, waste of power while computing and/or collecting unnecessary data that need not to be collected (e.g., due to the knowledge of a high likelihood of noise in the data), the lack of usability, actionability, contextualization, and personalization of the collected data (e.g., due to noise artifacts), and erratic performance in the presence of noise.

Figure 9:
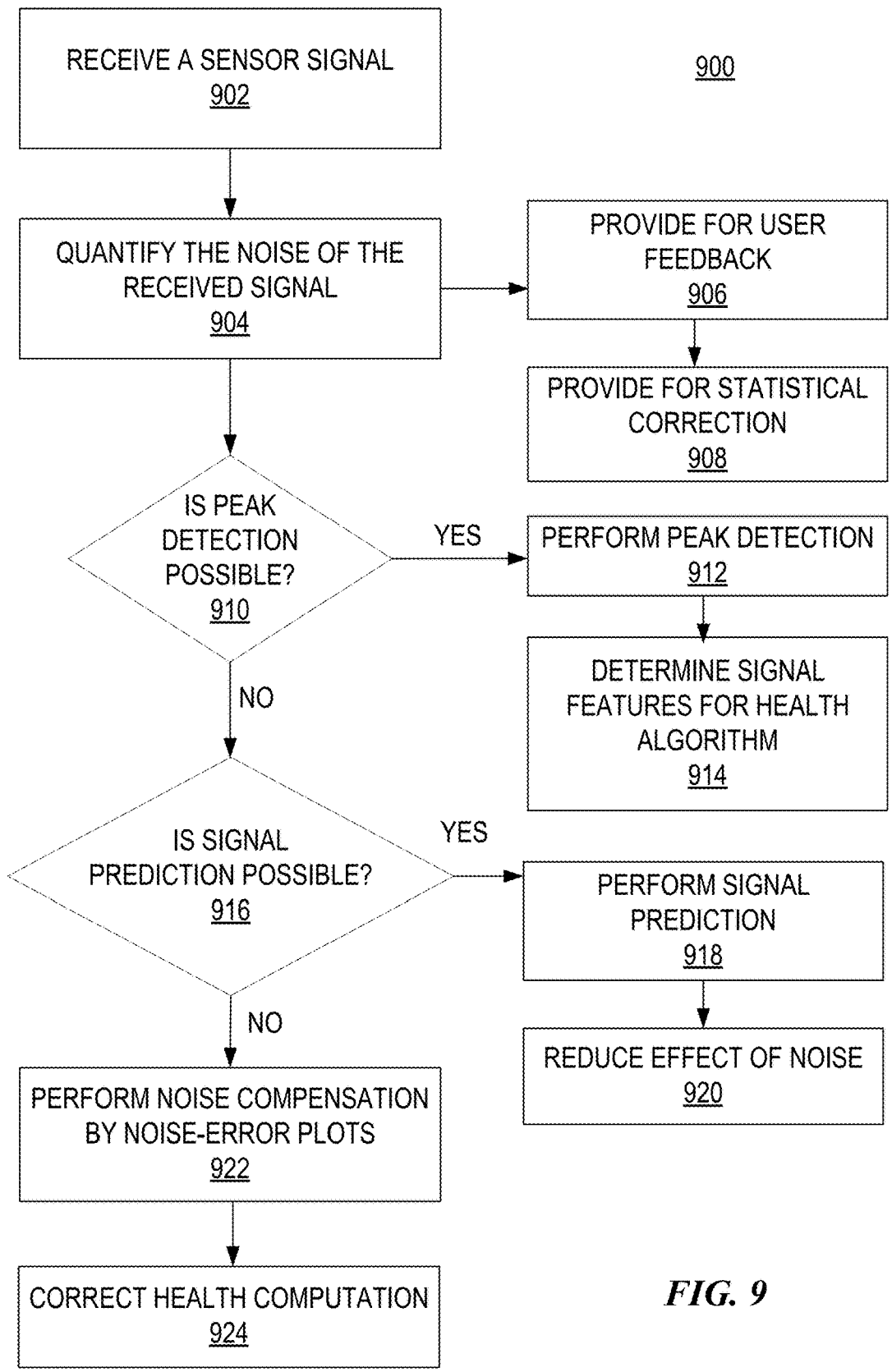
FIG. 9 illustrates an example method for computing health measurements using noisy sensors.

FIG. 9 illustrates an example method 900 for computing health measurements using noisy sensors. The method 900 may be performed by a biosensing device (e.g., one or more devices of health monitoring system 200), such as, a wearable device (e.g., a smart watch similar to health monitoring device 210, a patch such as health monitoring patch 270, etc.), a mobile device (e.g., a smart phone such as mobile electronic device 230, etc.), a specialized monitoring device (e.g., a medical device, etc.), other suitable devices, and any combination thereof (as described above with regard to FIGS. 1 and 2A-2B). As an example and not by way of limitation, health measurements may include stress, heart rate, sleep, emotional state, other relevant measurements, or any combination thereof.

The method may begin at step 902, where health monitoring system 200 may receive a sensor signal. As an example and not by way of limitation, the sensor signal may correspond to a PPG signal, an ECG signal, a bio-impedance signal, arterial blood pressure (BP signal), other suitable signals, or any combination thereof. For example, the PPG signal may be used to calculate HRV, which in turn, may be used to calculate a stress level of a user. However, noise in the PPG signal may cause an increase in variability in the HRV calculation, which may result in an erroneously low stress measurement. Thus, a primary goal of particular embodiments described below is to correct this error resulting from the noise in the PPG signal and provide the user with feedback about the quality and efficacy of the health measurements.

At step 904, health monitoring system 200 may quantify the noise of the received signal. In particular embodiments, the noise may be measured or quantified in terms of variation in the expected amplitude of the signal. As an example and not by way of limitation, an unexpected change in the signal amplitude from the average baseline amplitude may be a very reliable indication of the existence of noise in the signal. Example noise quantification will be described in greater detail below in connection with FIGS. 11, 12A, and 12B.

In accordance with example embodiments, noise can be computed in a variety of different ways. One approach of an example embodiment is to compute the noise as the ratio of the total area of the signal with the average signal in the clean PPG signal. If this ratio is significantly outside the expected range then the signal can be deemed noisy, and this ratio can serve to quantify the level of the noise. Another approach of an example embodiment is to estimate the number of peaks (or troughs) in the given pulse and if the given number is above a threshold then this is a quantifier of the noise in the signal. Yet another approach of an example embodiment is to measure the RMS deviation of the signal from the expected profile and this measure can be taken as the noise level of the signal. Yet another of an example embodiment is that for each peak and trough and zero crossing that is calculated, the expected signal profile in the vicinity of such features is calculated by curve fitting. Then the RMS deviation of the actual signal from the expected signal is used as the quantification of the overall noise in the signal for the given feature. As a further refinement of this approach, if a particular feature of the signal is used for the RR calculation then the noise in the vicinity of that feature is used as the marker of the noise in the signal.

One particular error-noise model may be more suited for error correction in a given setting, and that particular noise model can be taken as the preferred model. In an example embodiment, the health monitoring system 200 determines which error-noise model is to be selected automatically. For instance, the health monitoring system 200 can introduce synthetic noise in a clean PPG and measure the accuracy of correction of each error-noise model. The error-noise model with the highest accuracy (e.g., lowest error) can be selected.

Further, in a number of situations, the signal may be so corrupted that it is not possible to estimate any feature at all. In such a case, the number of such pulses (obtained by the extrapolation from the average heart rate) in the overall signal is used as a marker of overall noise in the signal. However, each noisy RR may corrupt, e.g., three RR-delta measurements. Hence, the noise that is discretely distributed in the signal may have a larger effect than noise that is present in a continuous stretch. For example, if the noise only affects one pulse, and such single noisy pulse instances are distributed throughout the signal then it can lead to, e.g., 30 noisy RR-delta computations and hence this case corrupts the signal more than the case where, e.g., 10 noisy pulses are consecutive. This information about the total expected number of RR-delta that are either erroneous or are simply not calculable can be a meaningful quantification of the total noise in the signal.

Health monitoring system 200 may continue method 900 by performing steps 906 and 910 sequentially or in parallel. At steps 906 and 908, health monitoring system 200 may provide the noise quantification to the user for feedback and further may provide the noise quantification for statistical correction. Example statistical correction will be described in greater detail below in connection with FIGS. 14A-C.

At step 910, health monitoring system 200 may determine whether peak detection of the received signal is possible. As an example and not by way of limitation, health monitoring system 200 may attempt to determine peaks of the sensor signal having certain properties such as a well-formed morphology that has repeated and detectable features in each cycle (e.g., a sinusoidal-type signal in the proximity of the peak in the well-formed PPG signal). If it is determined at step 910 that peak detection is possible (e.g., a determination of "YES"), health monitoring system 200 may proceed to step 912, where health monitoring system 200 may perform peak detection. Then, based on the detected peak information, at step 914, health monitoring system 200 may determine signal features for a health algorithm (e.g., a stress algorithm). As an example and not by way of limitation, the signal features may include a peak-to-peak time for HRV calculation, as described in more detail below in connection with FIGS. 15 and 16.

On the other hand, if it is determined at step 910 that peak detection is not possible (e.g., a determination of "NO"), health monitoring system 200 may proceed to step 916, where health monitoring system 200 may determine whether statistical prediction is possible. In particular embodiments, health monitoring system 200 determines whether statistical prediction is possible by looking at the statistical properties of prior PPG signals, and then based on this information, determine whether it is possible to reconstruct one or more missing pieces of a signal with reasonable accuracy. However, if the prior PPG signals are determined to be pure noise, then health monitoring system 200 may determine that no information may be extracted to help build the missing signal, and thus the reconstruction or prediction of the signal is also not possible. In other words, if it is determined at step 916 that signal prediction is possible (e.g., a determination of "YES"), then health monitoring system 200 may move to step 918 to perform signal prediction and adjust the received signal based on the predicted signal, and then to step 920 to reduce the effect of the noise.

On the other hand, if it is determined at step 916 that signal prediction is not possible (e.g., a determination of "NO"), then health monitoring system 200 may move to step 922 to perform noise compensation by using noise-error plots, as described in more detail below in connection with FIGS. 14A-C. Then, at step 924, health monitoring system 200 may correct the health (e.g., stress) computation based on the noise compensations from step 922. After correcting the health computation, the method may terminate.

Particular embodiments may repeat one or more steps of the method of FIG. 9, where appropriate. Although this disclosure describes and illustrates particular steps of the method of FIG. 9 as occurring in a particular order, this disclosure contemplates any suitable steps of the method of FIG. 9 occurring in any suitable order. Moreover, although this disclosure describes and illustrates an example method for computing health measurements using noisy sensors including the particular steps of the method of FIG. 9, this disclosure contemplates any suitable method for computing health measurements using noisy sensors including any suitable steps, which may include all, some, or none of the steps of the method of FIG. 9, where appropriate. Furthermore, although this disclosure describes and illustrates particular components, devices, or systems carrying out particular steps of the method of FIG. 9, this disclosure contemplates any suitable combination of any suitable components, devices, or systems carrying out any suitable steps of the method of FIG. 9.

Figure 10:
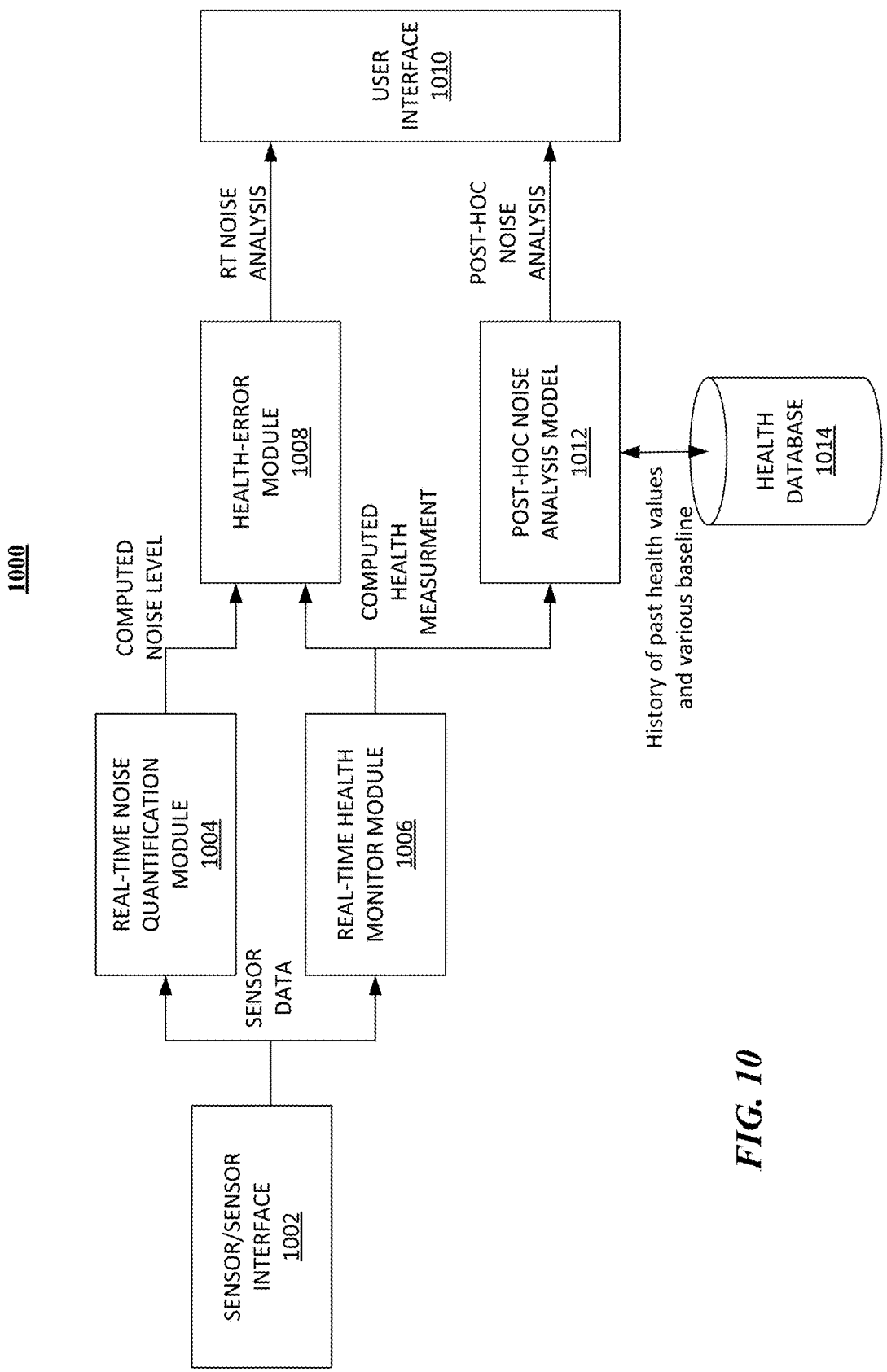
FIG. 10 illustrates a noise compensation system for computing health measurements using noisy sensors.

FIG. 10 illustrates a noise compensation system 1000 (e.g., of health monitoring system 200) for computing health measurements using noisy sensors. Noise compensation system 1000 may include one or more sensors (or a sensor interface) 1002 to receive sensor data from the user and/or from health monitoring system 200. Sensors 202 may provide the sensor data (e.g., HR data, user activity data, etc.) as an input to a real-time noise quantification module 1004 and a real-time health monitor module 1006. Real-time noise quantification module 204 may generate a computed noise level in the sensor data (e.g., step 904 of FIG. 9 of quantifying the noise of the received signal), and real-time health monitor module 1006 may generate a computed health measurement based on the noisy sensor data. Then, the computed noise level of the sensor data (from real-time noise quantification module 1004) and the computed health measurement (from real-time health monitor module 1006) may be provided as inputs to a health-error module 1008 to generate a real-time noise analysis. The outputs of the health-error module 1008 may then be provided to the user via a user interface (UI) 1010 in order to provide feedback to the user on the noise level of the sensor data (e.g., via user interfaces shown in FIGS. 4A and 4B). The real-time noise analysis of health-error module 208 will be described in more detail below in connection with FIGS. 14A-C.

Additionally or alternatively, the computed health measurements (from real-time health monitor module 1006) may be provided to a post-hoc noise analysis module 1012, which may be communicatively coupled to a health database 1014. Health database 1014 may maintain a data record of past computed health values and various baseline values (e.g., user-specific baseline values). Post-hoc noise analysis module 1012 may store the received computed health measurement in health database 1014. Periodically (e.g., every 24 hours), post-hoc noise analysis module 1012 may process the stored health measurements and/or baseline values and may provide post-hoc analysis data to the user for feedback (e.g., via UI 1010, as discussed above). In addition, post-hoc noise analysis module 1012 may use the post-hoc analysis data to update the noise model of noise compensation system 1000. The post-hoc noise analysis module 212 will be described in more detail below in connection with FIG. 13.

Particular embodiments may include one or more additional modules and/or repeat one or more steps described in relation to noise compensation system 1000 of FIG. 10, where appropriate. Although this disclosure describes and illustrates particular modules and particular steps described in relation to FIG. 10 as part of a particular setup and/or occurring in a particular order, this disclosure contemplates any suitable setup with regard to noise compensation system 1000 of FIG. 10. Moreover, although this disclosure describes and illustrates an example noise compensation system 1000 including particular modules used in particular ways, this disclosure contemplates any suitable noise compensation system 1000 including any modules, which may include all, some, or none of the modules of FIG. 10, where appropriate. Furthermore, although this disclosure describes and illustrates particular components, devices, or systems carrying out particular steps described in relation to noise compensation system 1000 of FIG. 10, this disclosure contemplates any suitable combination of any suitable components, devices, or systems carrying out any suitable steps described in relation to noise compensation system 1000 of FIG. 10.

Signal Correction

As discussed above, there are many sources of noise—such as, motion artifacts, noisy contacts, sensor errors, and the like—and accurate peak detection or signal correction may be difficult. In such cases, noise compensation by removing noise and/or compensating for noise may facilitate determining accurate measurements of stress and/or HRV. Specifically, noise can increase the variability of collected signal data, which may erroneously increase the perceived variability in the HRV computation, which may then erroneously affect the stress output.

Figure 11:
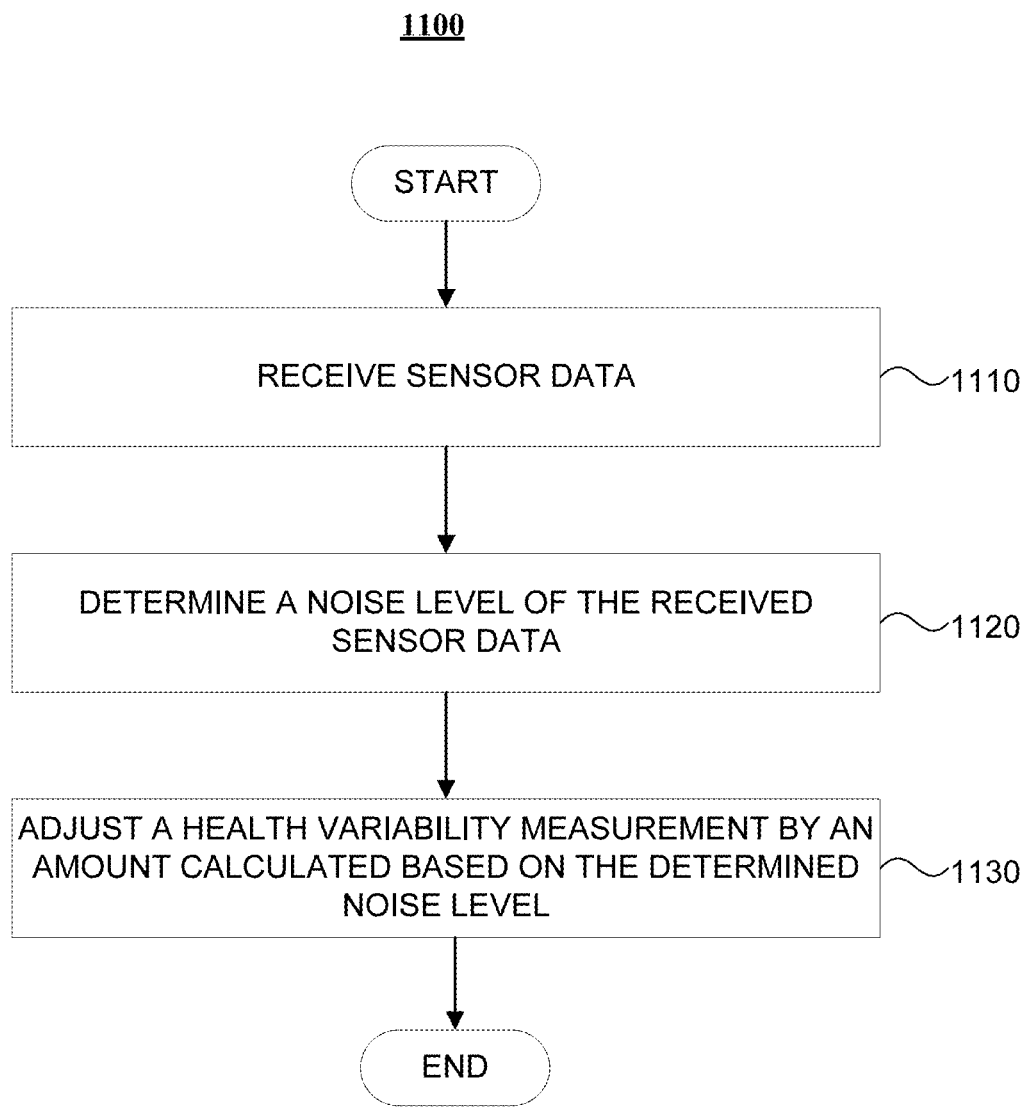
FIG. 11 illustrates an example method for determining a health-variability measurement of a user.

FIG. 11, for example, illustrates an example method 1100 for determining a health-variability measurement (e.g., HRV or stress level) of a user. The method may begin at step 1110, where health monitoring system 200 may receive, from a sensor of an electronic device of the user (e.g., mobile electronic device 230), sensor data. In particular embodiments, the sensor data may include data on a PPG signal over a noise-calculation period, and the health-variability measurement may include a HRV measurement. At step 1120, health monitoring system 200 may determine a noise level of the received sensor data. The determination of the noise level can be based on one or more of the approaches described above in connection with block 904 of FIG. 9.

Figure 12A:
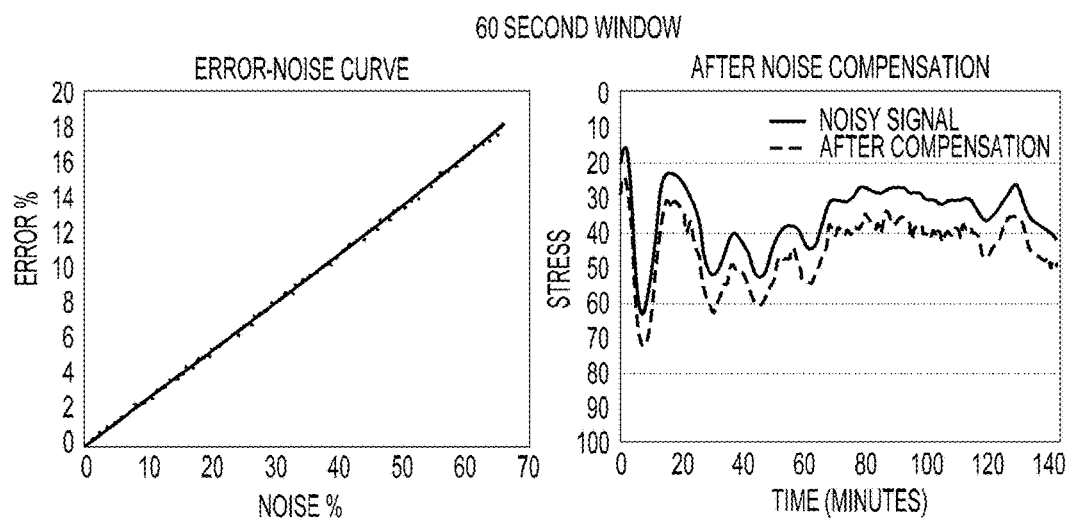
FIGS. 12A and 12B illustrate examples of heart-rate variability (HRV) measurement noise compensation results.
Figure 12B:
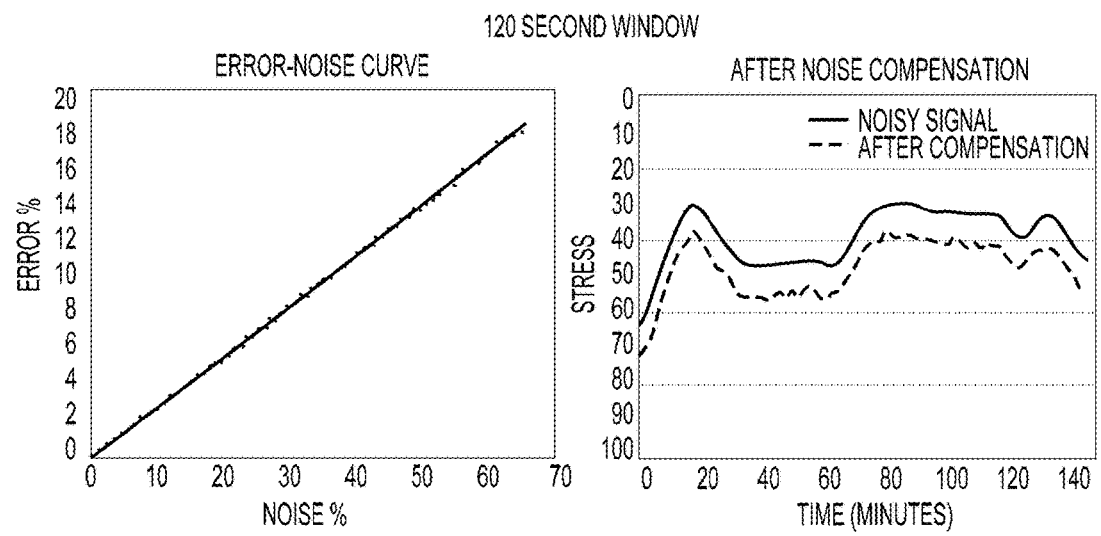

Then, at step 1130, health monitoring system 200 may adjust the health-variability measurement by an amount calculated based on the determined noise level. In particular embodiments, the adjusting of the health-variability measurement by the amount calculated based on the determined noise level may include decreasing the health-variability measurement by the calculated error-adjustment measurement. For example, FIGS. 12A and 12B illustrate examples of HRV measurement noise compensation results. Specifically, FIG. 12A illustrates noise compensation results 1200 including a noisy stress signal and an adjusted stress signal after compensation over a 60 second window of time, and FIG. 12B illustrates noise compensation results 1210 including a noisy stress signal and an adjusted stress signal after compensation over a 120 second window of time. As shown in both FIGS. 12A and 12B in connection with the error-noise curves, as the percentage of noise increases in a signal, the percentage of resultant error also increases. Thus, a noisy signal may result in an artificially elevated (and thus inaccurate) HRV computation and thus an artificially decreased stress computation in comparison with the signal after noise compensation. With noise compensation, the stress level is adjusted upward by the error determined based on the noise level and the error-noise curve in order to obtain a more accurate stress level of the user. In particular embodiments, after adjusting the stress measurement, health monitoring system 200 may send the adjusted stress measurement to the electronic device of the user (e.g., mobile electronic device 230).

The method of FIG. 11 was described in the context of adjusting the stress computation directly to compensate for noise. However, the HRV value can instead be adjusted before computing the stress level in alternative example embodiments so that the stress computation is indirectly adjusted to compensate for noise.

Particular embodiments may repeat one or more steps of the method of FIG. 11, where appropriate. Although this disclosure describes and illustrates particular steps of the method of FIG. 11 as occurring in a particular order, this disclosure contemplates any suitable steps of the method of FIG. 11 occurring in any suitable order. Moreover, although this disclosure describes and illustrates an example method for determining a health-variability measurement of a user including the particular steps of the method of FIG. 11, this disclosure contemplates any suitable method for determining a health-variability measurement of a user including any suitable steps, which may include all, some, or none of the steps of the method of FIG. 11, where appropriate. Furthermore, although this disclosure describes and illustrates particular components, devices, or systems carrying out particular steps of the method of FIG. 11, this disclosure contemplates any suitable combination of any suitable components, devices, or systems carrying out any suitable steps of the method of FIG. 11.

Post-Hoc Data Processing

In particular embodiments, post-hoc data process may entail using sensors to get a bird's eye view of a user's health. In a sensor-based health care monitoring system, one usage may be to provide daily summary and analysis of recorded data to educate and motivate the user about his health status. However, deeper insights may require clean data, especially to analyze subtler nuances. Since motion artifacts and noisy signal are difficult to resolve, most summaries provided to users include a number of errors (e.g., especially in the case of artifact-sensitive measurements such as HR and HRV). In areas of stress and ANS monitoring, such noise may mask critical moments, and the loss in accuracy may be enough to result in many types of 24×7 monitoring systems being impractical. As such, methods described below are for identifying and removing noisy signals (e.g., noisy HRV or RR-Delta data) from sensor data using dimension analysis.

As discussed above with regard to FIG. 10, post-hoc noise analysis model 1012 may receive a history of past health values and various baseline values (e.g., corresponding to PPG data, PPG derivatives such as RR and RR-Delta, and the like) as inputs and provides post-hoc noise analysis as an output. For example, during operation, post-hoc noise analysis model 1012 may store the computed health measurements from real-time health monitor module 1006 in health database 1014. Accordingly, over time post-hoc noise analysis model 1012 may generate a history of past health values and baseline values that can be used to perform post-hoc analysis.

Post-hoc analysis may correspond to, e.g., updating health measurements, updating noise models of real-time noise quantification module 1004 and health-error module 1008, other relevant post-hoc analyses, or any combination thereof. In particular embodiments, post-hoc noise analysis model 1012 may perform post-hoc analysis by parsing and saving real-time PPG data and PPG derivative data and then performing chaotic nonlinear analysis on the parsed and saved data, as described below.

The computed health measurements that post-hoc noise analysis model 1012 receives as input from real-time health monitor module 1006 may correspond to PPG data, PPG derivatives such as beat-to-beat heart rate (RR) and beat-to-beat heart-rate variability (RR-Delta), other relevant inputs, or any combination thereof. In particular embodiments, computed health measurements may correspond to any suitable sensor data representative of biomeasurements as well as computed values derived from such biomeasurements (e.g., a stress level). Post-hoc noise analysis model 1012 may parse and analyze a segment of the input (e.g., which may be stored in health database 1014) to determine a system dimension of the input. The system dimension may correspond to a value that is indicative of the level of noise in the parsed segments. Once the level of noise is quantified in a parsed segment, the confidence of computed real-time stress values can be reevaluated for correction or removal.

During post-hoc analysis processing, post-hoc noise analysis model 1012 may store the history of past health values and various baseline values as an embedding dimension when there is convergence and as a noise indicator when there is no convergence. More specifically, the parsed segments may each have a tag associated to them. The tag may be comprised of a beginning timestamp, an ending timestamp, an embedding dimension, and the results of a dimensional convergence test (e.g., indication of the fact that there was convergence). In particular embodiments, only higher-order physiological data is stored in the offline database, thereby facilitating efficient storage and data performance. The RR-Delta, timestamps, and embedding dimension values may be stored for offline processing. In particular embodiments, this database may be synced periodically (e.g., once a day), as this process may operate on a longer time scale than the normal stress processing.

As stated, post-hoc noise analysis model 1012 may process the history of past values offline in a post-hoc manner. As an example and not by way of limitation, post-hoc noise analysis model 1012 may be configured to process the history of data stored in the health database 1014 in response to a trigger condition. The trigger condition may be based on a number of conditions. As an example and not by way of limitation, the trigger condition may be time based, such as periodically trigger analysis every day, week, month, other suitable time frame, or any combination thereof. Additionally or alternatively, the trigger may be event based, such as a state of the device (e.g., a charging state, a transition to a charging state, a power-on state, etc.), a state of user activity (e.g., extreme noise beginning or end, for example, indicated by accelerometer integrated signal, a period of extreme stress, a sleep stage, a manual user request, etc.), a state of the history data (e.g., an amount of stored measurements for post-hoc processing, long-term stress measurement trends, frequency of stress processor use, frequency of previous noise detection, time since last update, etc.), other relevant state, or any combination thereof.

In particular embodiments, post-hoc noise analysis model 1012 may process the history of past health values and various baselines to separate noise out of the sensor data. Because of the post-hoc nature (e.g., no real-time constraints), the post-hoc noise analysis model 1012 may utilize a signal model having higher order dynamics and/or complex characteristics that may be too computationally expensive for real-time analysis. For instance, in an example embodiments, post-hoc noise analysis model 1012 may be configured to identify chaotic signal behaviors from noise, thereby increasing the accuracy of the noise model and the computed health measurements. A method for processsing the history data to generate the post-hoc analysis, in accordance with an example embodiment, is described in more detail below.

First, the health measurement data may be transformed from simple time-series representation to a phase space representation. That is, each point in a segment of the time series may be taken to be a particular element in a larger vector X(t) whose magnitude and direction represent a point in the collection of all possible states. By parsing the time-series history segments into unique vectors in phase space, the space itself may be constructed:

$$X(t)=[X(t),X(t+\tau),\ldots,X(t+(m-1)\tau]$$

The variable $\tau$ represents a system delay that is to be determined. For a given system delay $\tau$, the mutual information MI can be computed according to the following equation:

$$MI(\tau) = \sum_{x(i),x(i+\tau)} P(x(i), x(i+\tau))\log_2 \frac{P(x(i), x(i+\tau))}{P(x(i))P(x(i+\tau))}$$

The post-hoc noise analysis model 1012 may search for the system delay T that results in the first minimum value of mutual information. Details of how to evaluate the probability functions P are provided below in accordance with an example embodiment.

After determining the system delay $\tau$ from mutual information, post-hoc noise analysis model 1012 may separate and reconstruct the attractor governing the physiological signal. As an example and not by way of limitation, as the embedding dimension is increased, the computed correlation dimension levels off for low-dimensional chaotic time series data. For purely stochastic time series data, the correlation dimension should continue to increase. With these two cases, the stochastic and chaotic signals may be discriminated based on the trends of MI with respect to system delay $\tau$. This may be computed by calculating the entropies and joint entropies of the system.

Given this embedding dimension, post-hoc noise analysis model 1012 may compute a correlation dimension. As an example and not by way of limitation, post-hoc noise analysis model 1012 may compute a correlation dimension by assuming a power-law dimensional form, calculating the point-wise dimension, and extrapolating this to the correlation dimension. In particular embodiments, the power-law dimensionality function may take the following form $A(\varepsilon) \propto \varepsilon^d$, where $\varepsilon$ is the radius of the circle surrounding the vectorized points in the time-series. This $A(\varepsilon)$ calculation is now performed around the points in the time series and the results are averaged to transform point-wise dimension to correlation dimension, called $C_x$. At large values of $\varepsilon$ and small values of $\varepsilon$ there should be flat curves of $C_x$ because eventually circle leaves the attractor and there are no more points to be added, or shrink the sphere sufficiently to only have space for one point (e.g., the center of the circle in 2D). However, in-between these two limits there should exist a relatively constant line (e.g., plotted in log($\varepsilon$) v. log($C_x$) space).

Figure 13:
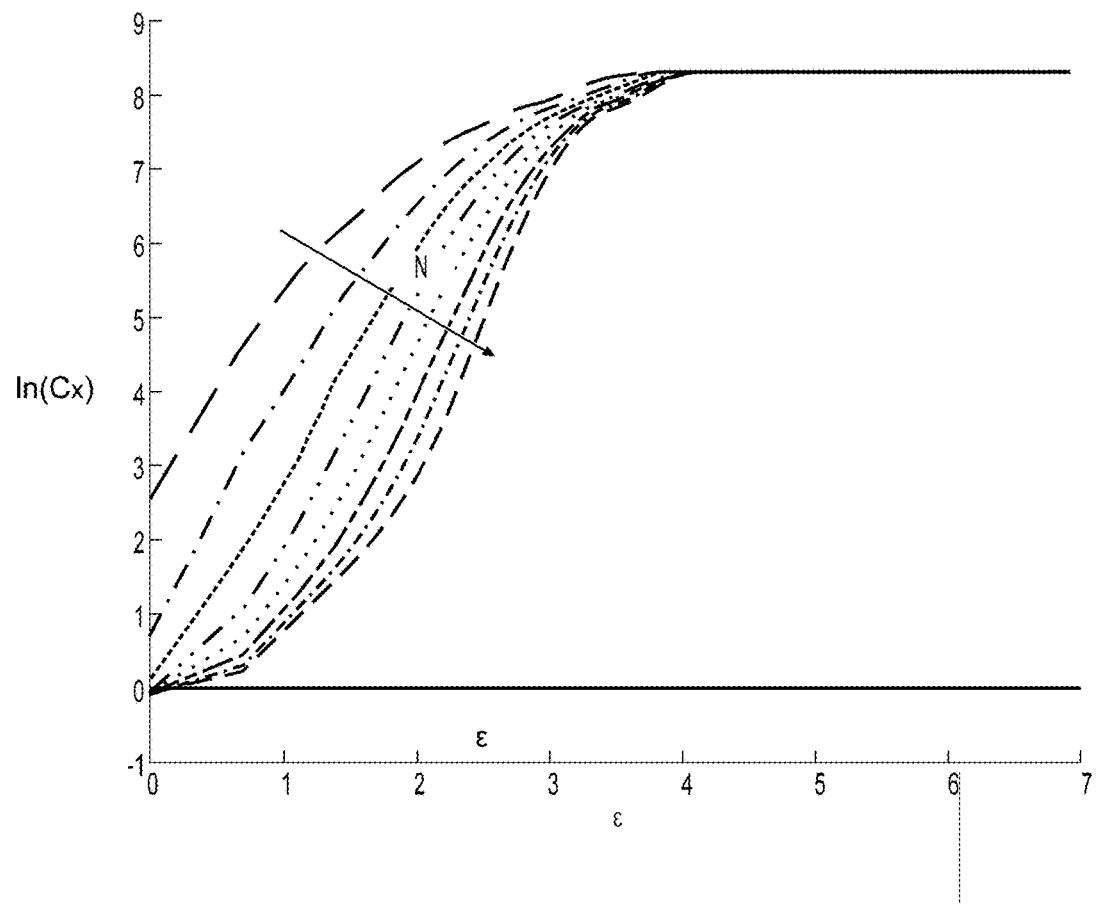
FIG. 13 illustrates an example use of an algorithm according to particular embodiments of this invention.

This processing may be done for a single system-embedding dimension. In alternative example embodiments, proper detection of the attractor may be performed by measuring a convergence of embedding dimension. This convergence may be visually seen from an example use of this algorithm in FIG. 13. In FIG. 13, the embedding dimension may be increased in the direction of the arrow. The convergence in embedding dimension may be seen as the slopes of these curves approaching the same value.

Highly stochastic signals may have infinite dimensionality since each dimension has noise distribution present; the stochasticity leads to infinite degrees of freedom. Chaotic signals reach a certain point where further increasing the system-embedding dimension has no effect on the correlation dimension. At this point, the attractor is said to be "disentangled." Distinguishing stochasticity from chaotic determinism, the correlation dimension stabilizes as the embedding dimension is sequentially increased. Otherwise, the signal is stochastic.

The discrete steps of the above-described method, in accordance with particular embodiments, are described in more detail below.

This method may include the use of mutual information (MI) and dimensional embedding for chaotic signals. MI is indicative of the average amount of bits of data a given measurement X(t) gives about another measurement X(t+$\tau$) at a later time. In other words, MI may correspond to the average amount of information (in bits) that one random variable (e.g., X(i)) gives about another (e.g., X(i+$\tau$)), which can be written into the following equation form:

$$MI(\tau) = \sum_{x(i),x(i+\tau)} P(x(i), x(i+\tau))\log_2 \frac{P(x(i), x(i+\tau))}{P(x(i))P(x(i+\tau))}$$

The above equation implies high MI for a delay corresponding a multiple of a period of a periodic signal. While increasing the delay τ, MI begins relatively high since the two data sets being compared are not delayed (e.g., different) by very much. More specifically, X(t) gives a lot of information about X(t+τ) when τ is small, and therefore means MI is high in this same area. As τ gets larger, there is less information the non-delayed measurement X(t) gives about a later one. This drop in MI continues until the delay corresponds to the periodicity of the signal (if periodicity is present). For PPG type-data, the signals may correspond to chaotic-based signals coupled to period signals, and post-hoc noise analysis model 1012 may separate the periodicity from the chaotic markers. To do this, post-hoc noise analysis model 1012 may evaluate MI as τ is increased and select the delay τ that produces the first minimum value of mutual information is chosen. This allows for data points X(t) and X(t+τ) to be somewhat decoupled, but not entirely independent. The process, in accordance with an example embodiment, is described below as Steps 1-9.

Step 1.

A window of data (RR-Delta samples) is saved for analysis. Post-hoc noise analysis model 1012 may store the data as an array in the database 1014. The size of the array should be sufficiently large since the finer points of the signal do not matter for long-term signals. The size of the array may be selected based on a number of considerations. In particular embodiments, the size of this array may be similar to the feature being detected. One example size for this array is 400 samples, which corresponds to approximately 8 minutes of stress monitoring. However, if the number of samples available is less than this, the algorithm can proceed with fewer numbers of samples. The delayed x(t+τ), . . . ,x(t+(m-1)τ points are generated from this array of data.

Step 2.

The data array x is delayed by τ (as τ changes from 1 to N) into N arrays. Each array point may be compared to the original array.

Step 3.

Once these arrays are generated, the MI is calculated between x and x(t+τ). This is then stored in an array for MI in order of increasing τ.

To calculate average mutual information, post-hoc noise analysis model (12 may perform the following operations:

(I). Normalize X and vertically shift the data to begin at zero by subtracting the minimum value and then dividing by the maximum value.

$$x_i^* = \sum x_i - x_{min}$$

$$\hat{x}_i = \frac{x_i^*}{x_{max}^*}$$

(II.) Delay the data in $\hat{X}$ by τ and call this $\hat{Y}$. $\hat{Y}$ is a delayed-image of $\hat{X}$ and then delayed-phase portrait is what the mutual information calculation is performed on.

(III.) Define how many bins to break the distribution functions into. Since this is a 2-dimensional portrait of $\hat{X}\hat{Y}$, the partitions are 2D box partitions. The size of the bins may be selected based on the application. Additionally, the size of the bins may be fixed or can vary adaptively. In particular embodiments, the bin size may selected based on the following equation:

$$n = \left\lfloor 1 + \log_2(N - \tau) + \frac{1}{2} \right\rfloor$$

The equation implies that there are $N^2$ boxes in this phase portrait. Here, N is the length of $\hat{X}$ and $\hat{Y}$.

(IV.) Check for variance. If the variance is approximately zero, then the MI would be approximately zero. In particular embodiments, this step may be omitted.

(V.) Define box-search variables $s_1$ and $s_2$. Here, a specific box corresponds to a point $(s_{1_i}, s_{2_j})$. These are now each traversed for every instance of τ. This may be performed using a nested for-loop in implementation. For example, $s_2$ can be a partition along the inner-horizontal axis of phase space and $s_1$ can be a partition along the inner-vertical axis.

Define probability distributions p, $p_x$ and $p_y$. These three values are the joint probability distribution, probability distribution of $\hat{X}$ and probability distribution of $\hat{Y}$ respectively. Find instances of $\hat{X}$ that satisfy the following conditions.

$$C_1: \frac{s_{1_i} - 1)}{n} < \hat{x}_k; \text{ with } \{k = 1, 2, \ldots n - \tau\}$$

$$C_2: \frac{s_{1_i}}{n} \geq \hat{x}_k; \text{ with } \{k = 1, 2, \ldots n - \tau\}$$

$$C_3: \frac{(s_{2_j} - 1)}{n} < \hat{x}_k; \text{ with } \{k = 1 + \tau, 2 + \tau, \ldots n\}$$

$$C_4: \frac{s_{2_j}}{n} \geq \hat{x}_k; \text{ with } \{k = 1 + \tau, 2 + \tau, \ldots n\}$$

And $C_{s_i s_j} = 1$ if all $C_p$ are true.

$G_{s_{1_i}, s_{2_j}} = 1$ if both $C_1$ and $C_2$ are true.

$F_{s_{1_i}, s_{2_j}} = 1$ if both $C_3$ and $C_4$ are true.

$$p = \frac{\sum_{s_{1_i}=1}^{n} \sum_{s_{2_j}=1}^{n} C_{s_{1_i}, s_{2_j}}}{N - \tau}$$

$$p_x = \frac{\sum_{s_{1_i}=1}^{n} \sum_{s_{2_j}=1}^{n} G_{s_{1_i}, s_{2_j}}}{N - \tau}$$

$$p_y = \frac{\sum_{s_{1_i}=1}^{n} \sum_{s_{2_j}=1}^{n} F_{s_{1_i}, s_{2_j}}}{N - \tau}$$

(VI.) Calculate the final MI given the probability probabilities calculated above. For instance, this calculation may be approximately equivalent to the equation:

$$MI(\tau) = p * \log_2 \frac{p}{p_x p_y}$$

(VII.) This calculation may repeated for a number of values of τ to obtain a distribution of MI over multiple delays.

Step 4.

Detect a peak in the array of MI for various delays. Specifically, the local peaks (corresponding to mutual information minimum) are being sought. These are the τ that correspond to Δt whose frequency transform gives the periodic-decoupled RR-Deltas.

Step 5.

Determine the point-wise dimension. This may be done for increasing values of m as defined in the following equation.

$$X(n)=[X(n),X(n+\tau),\ldots,X(n+(m-1)\tau]$$

That is, post-hoc noise analysis model 1012 may increment through values of m and perform point-wise dimension calculations on each. Here, X(n) is a vector in m-dimensional space that represent a single point in the phase space of the system. Increasing n is the direction of propagation along a phase-space trajectory. Post-hoc noise analysis model 1012 may select a value of n and parses the input function X(t) into vectors length m. Then post-hoc noise analysis model 112 may calculate the number of neighboring points at a given radius (ε) from each point (X(n)) in this phase-space. This value is then averaged over all points and then c is increased one step and the counting and averaging is performed once again. As stated above, post-hoc noise analysis model 1012 may use the model that the counted number of points is exponentially proportional with the following form.

$$A(\varepsilon) \propto \varepsilon^d$$

$$C_x(\varepsilon) = \frac{\Sigma_\varepsilon A}{N}$$

In this manner, C(ε) may be calculated as a discrete function of ε.

Step 6.

To obtain the embedding dimension d, post-hoc noise analysis model 1012 may apply an algorithm function on each side of this proportionality and then solve for d.

$$d = \frac{\ln C_x}{\ln \varepsilon}$$

Step 7.

Steps 5 and 6 may be repeated for increasing values of m.

Step 8.

The convergence is tested from m=2 to m=$m_{min}$. The value of $m_{min}$ can depend on the length of samples in the data storage buffer in example embodiments. If the slope continues to change more than a threshold value $\Delta d_{thresh}$, then the data is tagged as being noisy and these values of RR-Delta are removed from the stress calculation, which is then redone without these values.

Step 9.

The values of $d_{converge}$, which is the value of d after convergence has been verified will be saved for future analysis of physiological significance.

Noise Prediction and Signal Stitching/Replacement

In particular embodiments, a method to correct a noisy signal (e.g., a PPG signal) may be based on the observation that jitters or signal distortions can be local to peak or trough or zero-crossings. For signal distortions near signal maxima, minima, or zero-crossings, the noise may be estimated by first computing the expected signal profile, and then blending a constructed signal determined based on the expected signal profile with the raw signal. In the case of high signal distortions, the relevant portion of the signal may be completely thrown out and replaced by the constructed signal determined based on the expected signal profile. This way, the method results in providing a good PPG signal with low noise to the user for use and analysis. In addition, in comparison with the post-hoc analysis discussed above, the methods for stitching and/or replacing noisy signals discussed below may be done in real-time and very quickly in order to output a relatively noise-free signal to the user.

As discussed above, as shown in FIG. 9, at step 916, health monitoring system 200 may determine whether statistical prediction is possible. In particular embodiments, health monitoring system 200 may determine whether statistical prediction is possible by looking at the statistical properties of prior PPG signals, and then based on this information, determine whether it is possible to reconstruct one or more missing pieces of a signal with reasonable accuracy. However, if the prior PPG signals are determined to be pure noise, then health monitoring system 200 may determine that no information may be extracted to help build the missing signal, and thus the reconstruction or prediction of the signal is also not possible. In other words, if it is determined at step 916 that signal prediction is possible (e.g., a determination of "YES"), then health monitoring system 200 may move to step 918 to perform signal prediction and adjust the received signal based on the predicted signal, and then to step 920 to reduce the effect of the noise. On the other hand, if it is determined at step 916 that signal prediction is not possible (e.g., a determination of "NO"), then health monitoring system 200 may move to step 922 to perform noise compensation by using noise-error plots. In addition, as illustrated in FIG. 10, the sensor data may be inputted into real-time noise quantification module 1004, which may determine a noise level of the sensor data, and real-time health monitor module 1006, which may generate a health measurement after compensating for the noise in the sensor data.

Figure 14A:
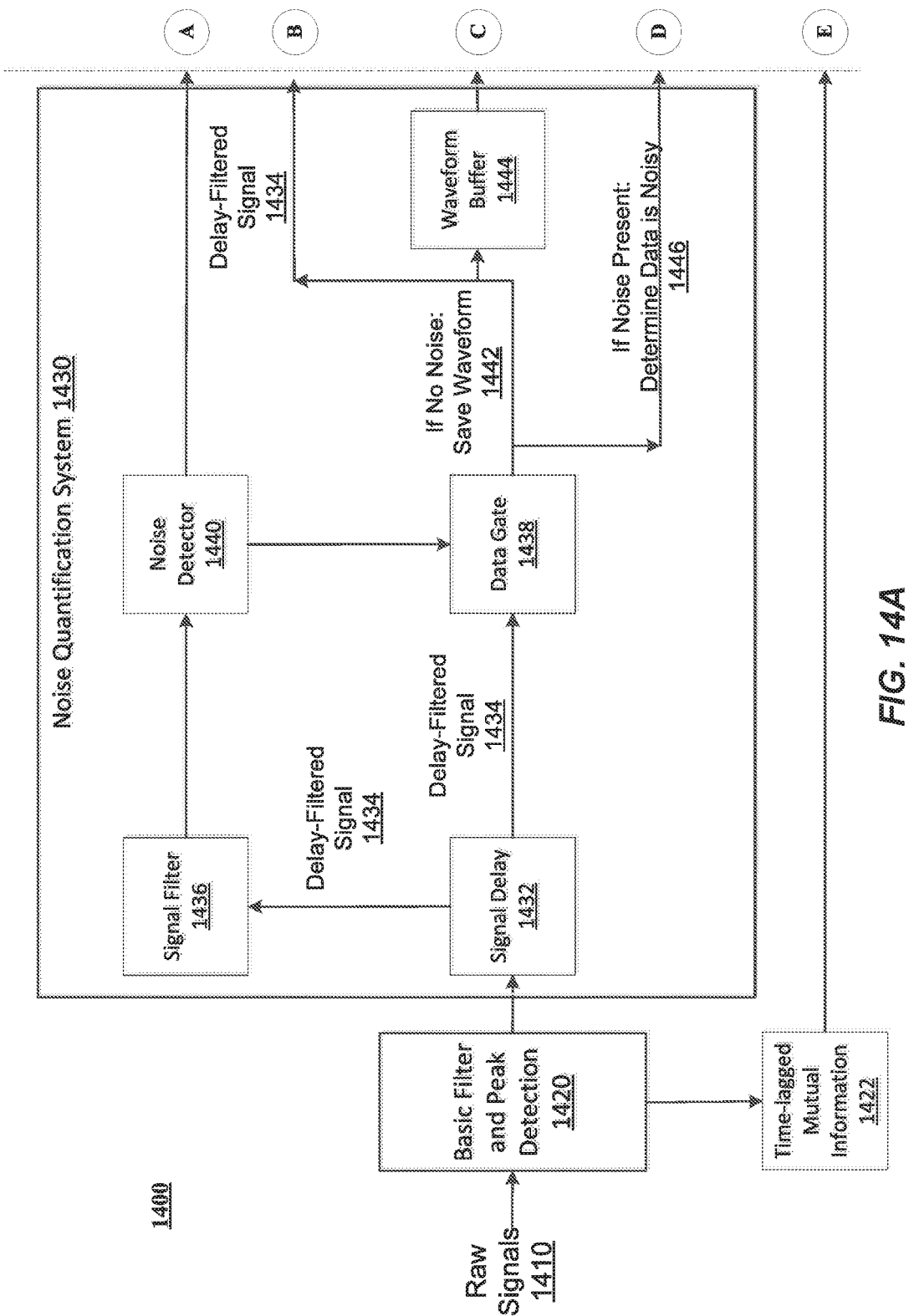
FIGS. 14A-C illustrate a noise correction system for noise prediction and signal stitching or replacement.
Figure 14B:
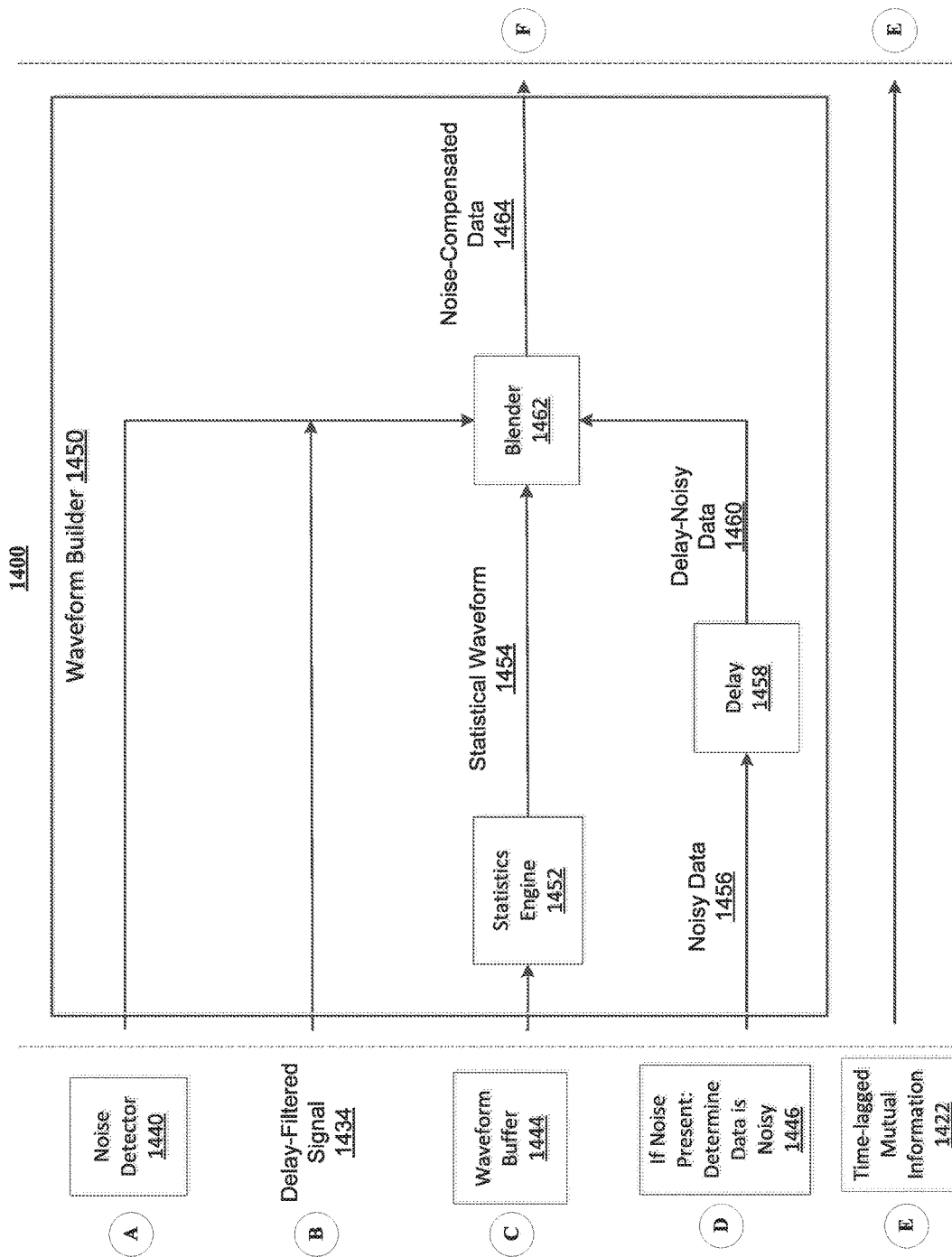
Figure 14C:
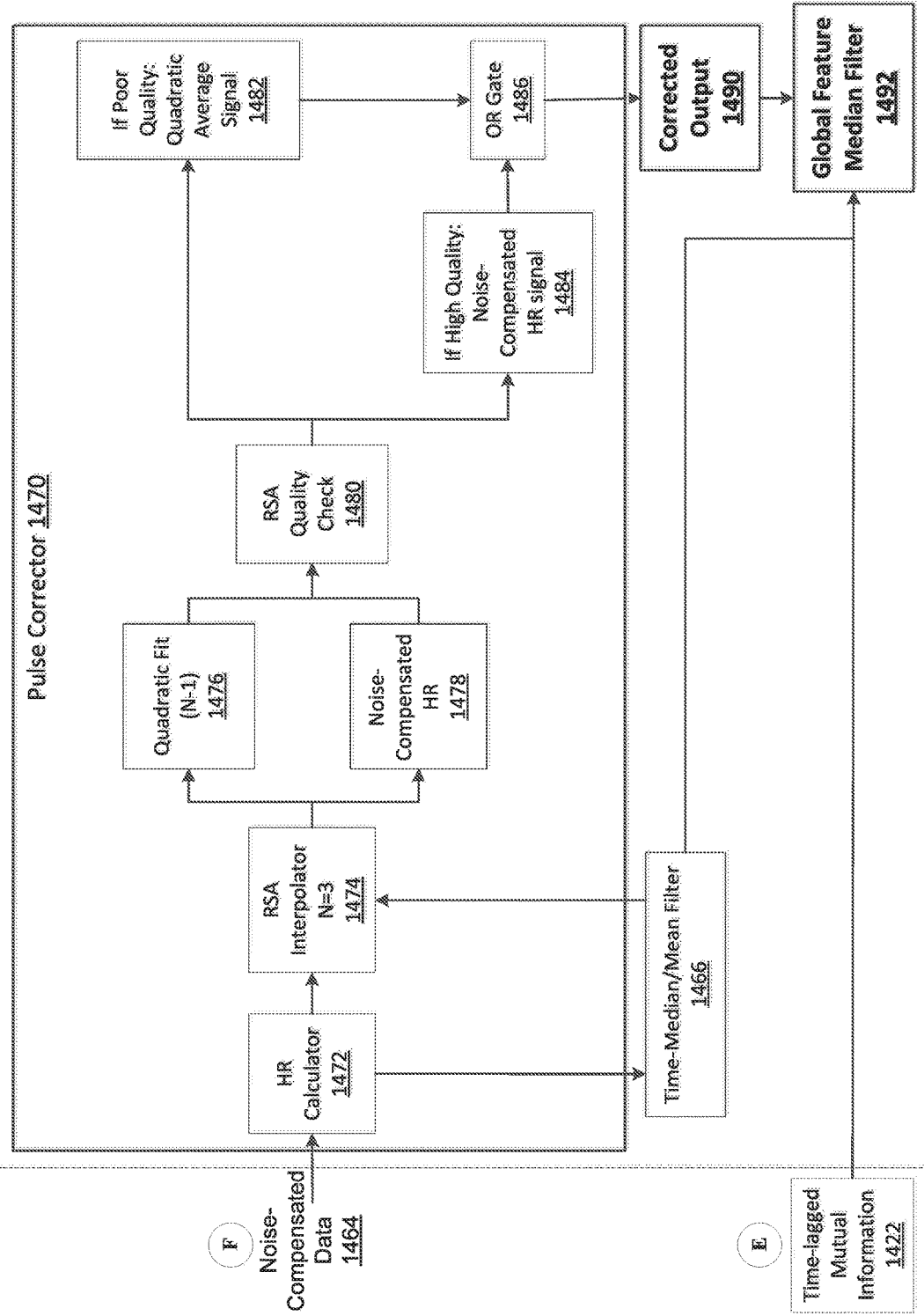

FIGS. 14A-C illustrate a noise correction system 1400 for noise prediction and signal stitching or replacement. Noise compensation system 1400 (e.g., of health monitoring system 200), which may be executed via real-time noise quantification module 1004 and/or real-time health monitor module 1006, may initially receive an input of raw signals 1410. As discussed above, raw signals 1410 may be received from the sensor (or sensor interface) 1002. Raw signals 1410 may be processed through basic filtering and feature extraction 1420. As an example and not by way of limitation, the raw signals 1410 may be processed through basic filtering to remove a portion of noise (e.g., any blocks of the raw signals with a frequency greater than 15 Hz) and to remove unwanted DC offsets and low-frequency oscillations. In addition, the raw signals 1410 may be processed with a multi-band filter bank such that peak, trough, and zero-crossing times may be extracted from the signal, and this information may be stored for later use (e.g., to determine whether a signal is noisy or not). During the signal processing of a PPG signal, some embodiments may look for signal peaks at expected locations. In the situation of high heart rate obtained due to sudden exertion such as exercise, the embodiments that look for signal peaks at expected locations may provide erroneous results since the expected signal behavior has changed dramatically, and often suddenly; for example, as the heart rate increases from 5 BPM to 100 BPM and then onwards to 200 BPM. Particular embodiments may adjust to the dramatic changes in PPG profile by carrying average signal profiles (for example, RR-intervals or first or second derivative of rate of change in the signal). This information is kept both in terms of a local signal (that is, signal around an expected heart beat) as well as a global signal (that is, signal around several heart beats) around the given locality. This allows particular embodiments to do local processing in cognizance of the global trend. For example, if the global features seem to be indicating that the heart rate seems to be generally speeding up, then the local signal processing parameters may be correspondingly adjusted accordingly (e.g., so that particular embodiments look for a possible signal feature (such as signal peak) at an earlier point in time).

The time-lagged mutual information block 1422 may compute a time-lagged mutual information output on an array of PPG samples from the filtered raw signal. For example, X(t) can represent an array of N>0 PPG samples outputted by the basic filter and peak detection 1420. The time-lagged mutual information block 1422, in accordance with example embodiments, computes a mutual information output MI(τ) for a delay r, e.g., as described above in connection with the post-hoc analysis model 1012, using the array of N PPG samples.

The peaks of this distribution MI(τ) may provide features present in the PPG signal. One of these features may be heart rate (which, e.g., is pseudo-periodic). For instance, a delay r that results in a peak of M can correspond to a HR estimate.

An example benefit, among others, of an example embodiment of using MI for HR calculation is that it can facilitate noise immunity since the self-similarity may not be dramatically reduced by noise at any remarkable point in the PPG morphology (such as zero crossing or peak). Additionally, it may provide a robust method to determine the range in which the HR lies so that the outliers can be more easily removed. Thus, confounders in HR due to noise but posing as RSA based variation can be more easily identified. As such, mutual information approach may be more noise-resilient to different types of noise than the other waveform features.

With further reference to FIGS. 14A-C, the filtered raw signal may be sent to noise quantification system 1430. Noise quantification system 1430 may include a signal delay 1432, a signal filter 1436, a data gate 1438, a noise detector 1440, and a waveform buffer 1446. In particular embodiments, the filtered raw signal may be sent to signal delay 1432, where the delay-filtered signal 1434 may be sent to both signal filter 1436 and data gate 1438. In particular embodiments, signal delay 1432 may store and maintain the filtered raw signal for a predetermined period of time before passing the delay-filtered signal 1434 to data gate 1438 so that the delay-filtered signal 1434 sent to signal filter 1436 may be analyzed by noise detector 1440 to determine whether noise is present (e.g., so that the noise may be detected and handled in approximately real-time). In determining whether noise is present, noise detector 1440 may compute relative pulse width and pulse amplitudes (e.g., between a first pulse and one or more second subsequent pulses) and compare with physiologically acceptable deviations, and metric changes greater than the physiologically acceptable deviations may be considered to be noise. As an example and not by way of limitation, for a PPG waveform signal, signal delay 1432 may maintain (e.g., "delay") the filtered raw signal for a period of about 100 samples, which corresponds to about a single pulse of a heartbeat. This way, if it is determined that the filtered raw signal contains noise, then noise correction system 1400 may go back to the beginning of the single pulse (e.g., located somewhere in the 100 samples) and correct the filtered raw signal before the noise occurs. In particular embodiments, for the PPG waveform signal, the beginning of the single waveform may be a peak (e.g., where the single pulse is determined based on a pulse-peak to the next pulse-peak), a trough (e.g., where the single pulse is determined based on a trough to the next trough), a zero-crossing (e.g., where the single pulse is determined based on a zero-crossing to the next zero-crossing), other relevant waveform feature, or any combination thereof. Particular waveform features and advantages of specific waveform features are discussed in more detail below.

Once noise detector 1440 determines whether or not noise is present in the delay-filtered signal 1434, this determination is sent to data gate 1438 in addition to being sent to a blender 1462. If it is determined that there is no noise (e.g., step 1442), then the delay-filtered signal 1434 is saved and inputted into a waveform buffer 1444, while also being sent to blender 1462 (discussed below). In particular embodiments, waveform buffer 1444 (e.g., a memory buffer) may store only a predetermined amount of data. As an example and not by way of limitation, for the PPG waveform signal, waveform buffer 1444 may store only data corresponding to three pulses of heartbeats (e.g., N=3). Waveform buffer 1444 may be configured to store a small number of pulses such that noisy signals (e.g., pulse signals with large deviations in one or more features as compared with one or more previous pulse signals) may be determined to noisy in comparison with previous signals but at the same time allowing for gradual changes in the signal. In addition, when waveform buffer 1444 starts with nothing in the buffer (e.g., no PPG waveforms stored), the initial determination will be that the delay-filtered signal does not contain noise such that at least three PPG pulses may be stored before analyzing the waveform of a present PPG pulse with the waveform of a previous PPG pulse. Then, after there are three non-noisy PPG waveforms stored in waveform buffer 1444, each additional PPG waveform that is determined to not be noisy is saved to waveform buffer 1444 while an old PPG waveform (e.g., the PPG waveform from four pulses ago) will be removed. This way, waveform buffer 1444 may always maintain the last three PPG waveforms corresponding to the last three pulses.

In particular embodiments, the number of pulses stored in waveform buffer 1444 may be small enough to allow for meaningful comparison and also may be large enough to average out inter-pulse deviations and noise. As an example and not by way of limitation, three pulses of heartbeats is stored in waveform buffer 1444 due to the phenomenon of respiratory sinus arrhythmia (RSA), which is heart-rate variability in synchrony with respiration, by which the R-R interval on an ECG is shortened during inspiration and prolonged during expiration. The effect of RSA on the PPG waveform is such that inhalation gradually increases the HR while decreasing the PPG waveform amplitude, whereas exhalation gradually decreases the HR while increasing the PPG waveform amplitude. In particular embodiments, the effect of RSA on the PPG waveform may be factored into and separate from the determination of noise in the PPG waveform (e.g., N=3 is chosen to fall within the known RSA cycle).

On the other hand, if it is determined that there is noise present in the delay-filtered signal 1434 (e.g., step 1446), then as shown in FIGS. 14A-C, then noisy data 1456 is sent to delay 1458 of a waveform builder 1450. In particular embodiments, waveform builder 1450 may include a statistics engine 1452, delay 1458, and blender 1462. In particular embodiments, the delay-filtered signal 1434 processed through waveform buffer 1444 is inputted into statistics engine 1452, which then generates a statistical waveform 1454 based on the data stored in waveform buffer 1444 (e.g., the last 3 pulses), and the data may also be adjusted to match the changing period of the signal to allow for better signal matching as the PPG waveform signal goes from noisy to clean and the statistical waveform 1454 is transitioning to real-time data. This statistical waveform 1454 is then sent to blender 1462. In addition, noisy data 1456 is inputted into delay 1458, where it is stored for a predetermined amount of time such that the statistical waveform 1454 may be generated by statistics engine 1452 (e.g., allowing for signal correction in approximately real-time). Then, delay-noisy data 1460 and the statistical waveform 1454, in addition to the determination from noise detector 1440 and the delay-filtered signal 1434 (e.g., output by data gate 1438), are inputted into blender 1462. Blender 1462 may then blend the statistical waveform 1454 (e.g., the constructed waveform) with the delay-filtered signal 1434 (e.g., the raw-signal waveform) when noise is detected in the delay-filtered signal 1434. As an example and not by way of limitation, the blending may include beginning with zero strength (e.g., 0%) given to the constructed waveform and 100% strength given to the raw-signal waveform at the point nearest to the a selected feature (e.g., the zero-crossing, the peak, or the trough), and then progressively weighing the constructed waveform more heavily until the signal is 100% constructed waveform and 0% raw-signal waveform. In addition, this process may be gradually done in reverse to merge two signals after noise is no longer detected in the signal. In particular embodiments, the resultant blended signal may then be sent through an additional filter to ensure points on the waveform are smoothly blended into this resultant, blended signal. Then, blender 1462 may output noise-compensated data 1464 (e.g., a noise-compensated signal), to a pulse corrector 1470.

As shown in FIGS. 14A-C, pulse corrector 1470 may include a heart rate (HR) calculator 1472, a RSA interpolator 1474, a RSA quality check 1480, and an OR gate 1486. The purpose of pulse corrector 1470 is to take into account the RSA cycle when suggesting the HR in the presence of the noisy signal, which may be done using quadratic interpolation of the HR signal. First, noise-compensated data 1464 is inputted into HR calculator 1472 to determine a heart-rate signal based on the noise-compensated data 1464. Then, the heart-rate signal determined via HR calculator 1472 is sent to RSA interpolator 1474. In particular, for each feature that heart rate is calculated on (trough, peaks, etc.), the heart rate (HR Calculator 1472) may be sent first into a time (sample) median filter and then to a moving average filter (collectively shown in FIGS. 14A-C as a time-median/mean filter 1466) to reduce outlier presence. The RSA interpolator 1474 may calculate a quadratic-fit signal 1476 (e.g., an interpolated RSA-estimate), and compare that with a noise-compensated HR signal 1478 via RSA quality check 1480. If it is determined that the quadratic-fit signal 1476 deviates from the noise-compensated HR signal beyond a predetermined amount (e.g., a threshold amount of acceptable deviation), that is, if it is determined that the noise-compensated HR signal 1478 is of poor quality, then a quadratic average signal 1482 is calculated based on both the quadratic-fit signal 1476 and the HR noise-compensated HR signal 1478, and this quadratic average signal 1482 is outputted via OR gate 1486 as the corrected output 1490 (e.g., an outputted signal that is corrected in approximately real-time). On the other hand, if it is determined that the quadratic-fit signal 1476 does not deviate from the noise-compensated HR signal beyond the predetermined amount, then the noise-compensated HR signal 1484 is outputted via OR gate 1486 as the corrected output 1490. In particular embodiments, the threshold amount of acceptable deviation may depend on the circumstances. As an example and not by way of limitation, when no noise is detected, the maximum allowable deviation between a first set of data and a second, subsequent set of data may be 15%. However, when noise is detected, the maximum allowable deviation between the first set of data and the second, subsequent set of data may be decreased to 5%. For each feature that heart rate is calculated on (trough, peaks, etc.), the heart rate (Corrected Output 1490) may sent first into a global feature-median filter and then to a moving average filter (collectively shown in FIGS. 14A-C as a global feature median filter 1492) to reduce outlier presence. The global feature-median filter 1492 may contain synchronized final corrected outputs from the processing blocks of heart rate from trough, peak, pulse-corrected locations and mutual information.

Particular embodiments may repeat one or more steps of the method of FIGS. 14A-C, where appropriate. Although this disclosure describes and illustrates particular steps of the method of FIGS. 14A-C as occurring in a particular order, this disclosure contemplates any suitable steps of the method of FIGS. 14A-C occurring in any suitable order. Moreover, although this disclosure describes and illustrates an example system and method for noise prediction and signal stitching or replacement including the particular systems and steps shown in FIGS. 14A-C, this disclosure contemplates any suitable systems and method for noise prediction and signal stitching or replacement including any suitable systems and steps, which may include all, some, or none of the systems and steps of the method of FIGS. 14A-C, where appropriate. Furthermore, although this disclosure describes and illustrates particular components, devices, or systems carrying out particular steps of the method of FIGS. 14A-C, this disclosure contemplates any suitable combination of any suitable components, devices, or systems carrying out any suitable steps of the method of FIGS. 14A-C.

Feature Detection and Analysis

As discussed above, as shown in FIG. 9, at step 910, health monitoring system 200 may determine whether peak detection of the received signal is possible. As an example and not by way of limitation, health monitoring system 200 may attempt to determine peaks of the sensor signal having certain properties such as a well-formed morphology that have repeated and detectable features in each cycle (e.g., a sinusoidal-type signal in the proximity of the peak in a PPG signal). If it is determined at step 910 that peak detection is possible (e.g., a determination of "YES"), health monitoring system 200 may proceed to step 912, where health monitoring system 200 may perform peak detection. Then, based on the detected peak information, at step 914, health monitoring system 200 may determine signal features for a health algorithm (e.g., a stress algorithm).

The method for accurate peak detection is based on the observation that even though a signal may be distorted, some aspects of it might still be amenable to analysis. These can be the peak, the trough, or the zero-crossing points (e.g., where the signal during its rising or falling edge cross the zero line), as discussed below with regard to FIG. 15, which illustrates an example signal according to particular embodiments of this invention. As an example and not by way of limitation, ambiguous peak positions may result in errors in the detection of these peaks and errors in calculations using these measurements (e.g., inaccurate determinations of heart rate and stress levels). As another example and not by way of limitation, the point of maximum slope (e.g., the zero-crossings of detrended PPG signals) may be more robust to errors. In particular embodiments, each of the peaks, troughs, or zero-crossings may be approximated by quadratic fitting (e.g., near peaks or troughs) or linear fitting (e.g., near zero-crossings). Once the approximation is done, the extent of noise may be calculated by calculating the deviation of the approximated graph (e.g., based on the approximated points) with the signals generated (e.g., the received raw signals).

Figure 16:
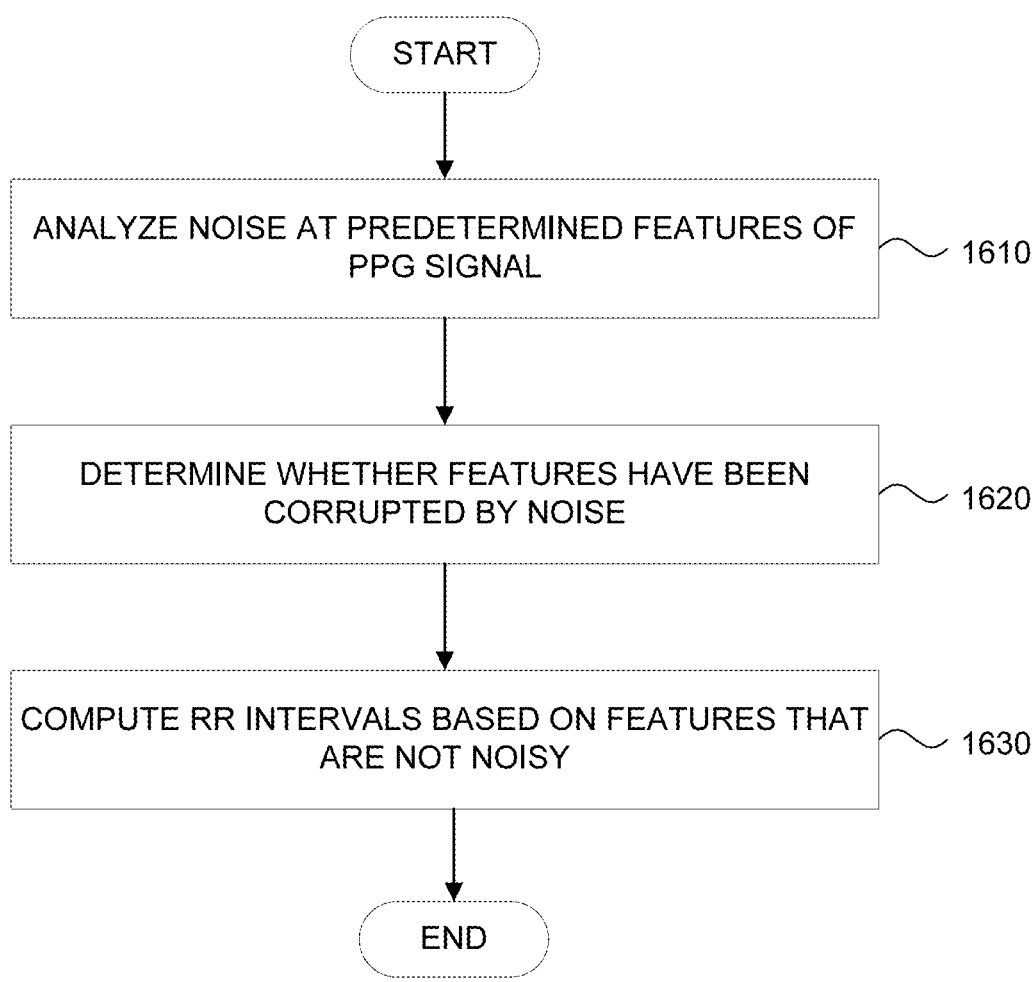
FIG. 16 illustrates an example method for detecting and analyzing signal features based on particular embodiments of this invention.

FIG. 16 illustrates an example method 1600 for detecting and analyzing signal features based on particular embodiments of this invention. The method may begin at step 1610, where health monitoring system 200 may analyze noise at predetermined features of a PPG signal. At step 1620, health monitoring system 200 may determine whether one or more of the features have been corrupted by noise. At step 1630, health monitoring system 200 may compute the RR intervals based on one or more of the features that are not noisy.

Figure 15:
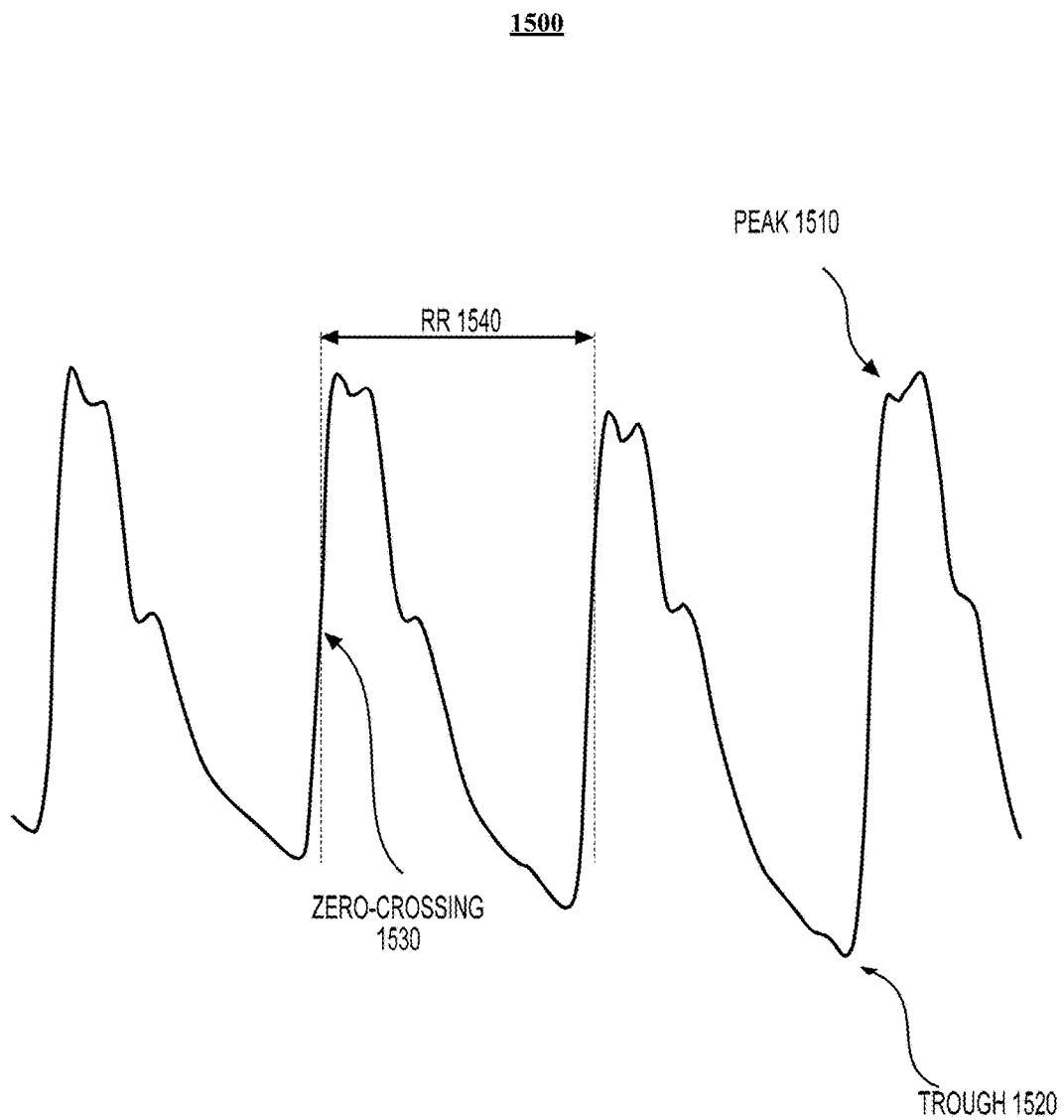
FIG. 15 illustrates an example signal according to particular embodiments of this invention.

An example of signal feature detection and analysis is explained using PPG signals and FIG. 15. In particular embodiments, quantifying an amount of noise of the PPG signal may include quantifying an amount of noise associated with each of a plurality of predetermined features of the PPG signal. As discussed below, the plurality of predetermined features of the PPG signal may include one or more peaks associated with the PPG signal, one or more troughs associated with the PPG signal, one or more zero-crossings associated with the PPG signal, or any combination thereof. In particular embodiments, PPG signals may be acquired from the user's wrist at different sampling rates using a sensor platform containing LEDs and photodetectors (e.g., as part of health monitoring system 200). Data received from health monitoring system 200 may be digitized at varying frequencies, for example, ranging from 25 Hz to 800 Hz. FIG. 15 illustrates an example signal according to particular embodiments of this invention. As shown in FIG. 15, an example PPG signal 1500 may include peaks 1510, troughs 1520, zero-crossings 1530, and RRs 1540 (heart beat-to-heart beat intervals). The plot may contain 4 seconds of PPG signals sampled by health monitoring system 200 via the user's wrist. As an example and not by way of limitation, as shown in FIG. 15, a time series of the PPG signals may contain a number of peaks (e.g., 4 peaks) and the PPG signal morphological features may change between each of the peaks.

In particular embodiments, health monitoring system 200 may selectively use features of the PPG signal based on the noise level determined for each feature. In addition, the signal in the vicinity of each feature may be analyzed to determine whether noise is present to determine whether the feature is a reliable feature. As an example and not by way of limitation, if health monitoring system 200 determines that a peak of the PPG signal is noisy, health monitoring system 200 may calculate the RR interval not from a first peak to a second, subsequent peak, but from a zero-crossing to a subsequent zero-crossing. In other words, health monitoring system 200 may analyze all features associated with a signal to select one or more features to use in signal analysis based on the noise in one or more of the features, and also discard any feature that are determined to be noisy.

Particular embodiments may repeat one or more steps of the method of FIG. 16, where appropriate. Although this disclosure describes and illustrates particular steps of the method of FIG. 16 as occurring in a particular order, this disclosure contemplates any suitable steps of the method of FIG. 16 occurring in any suitable order. Moreover, although this disclosure describes and illustrates an example method for detecting and analyzing signal features including the particular steps of the method of FIG. 16, this disclosure contemplates any suitable method for detecting and analyzing signal features including any suitable steps, which may include all, some, or none of the steps of the method of FIG. 16, where appropriate. Furthermore, although this disclosure describes and illustrates particular components, devices, or systems carrying out particular steps of the method of FIG. 16, this disclosure contemplates any suitable combination of any suitable components, devices, or systems carrying out any suitable steps of the method of FIG. 16.

Continuous Biological Measurements and Alarm Fatigue Proof Features

As discussed above, stress is considered to be one of the largest contributors to various health problems. Technology for stress monitoring may focus on providing real-time instantaneous measurements of stress. However, stress measurements may be meaningful only in the context of chronic and prolonged stress, as short term spikes in stress, unless extremely sharp and unusual, are not very significant to the user's health. In fact, frequent alerts of short term stress event may result in "alarm fatigue" in which the user becomes desensitized to the stress notifications and begins to ignore the alarms altogether. Moreover, continuous monitoring for chronic stress requires consuming a lot of power, and therefore is difficult to implement based on the power constraints of wearable electronic devices. Accordingly, particular embodiments discussed below address the issues described above to facilitate accurate, meaningful measurement of psychological stress that is also performed in a power efficient manner. As an example and not by way of limitation, particular embodiments detect signs of relatively longer term disturbances in stress homeostasis. In addition, particular embodiments focus on such measurements in the context of monitoring and management of health and/or wellness that are both well-suited for bio-sensing and power efficiency (e.g., by a factor of at least 4) while considering a user-specific context of the measurement and/or a user-specific baseline of the given user.

Figure 17:
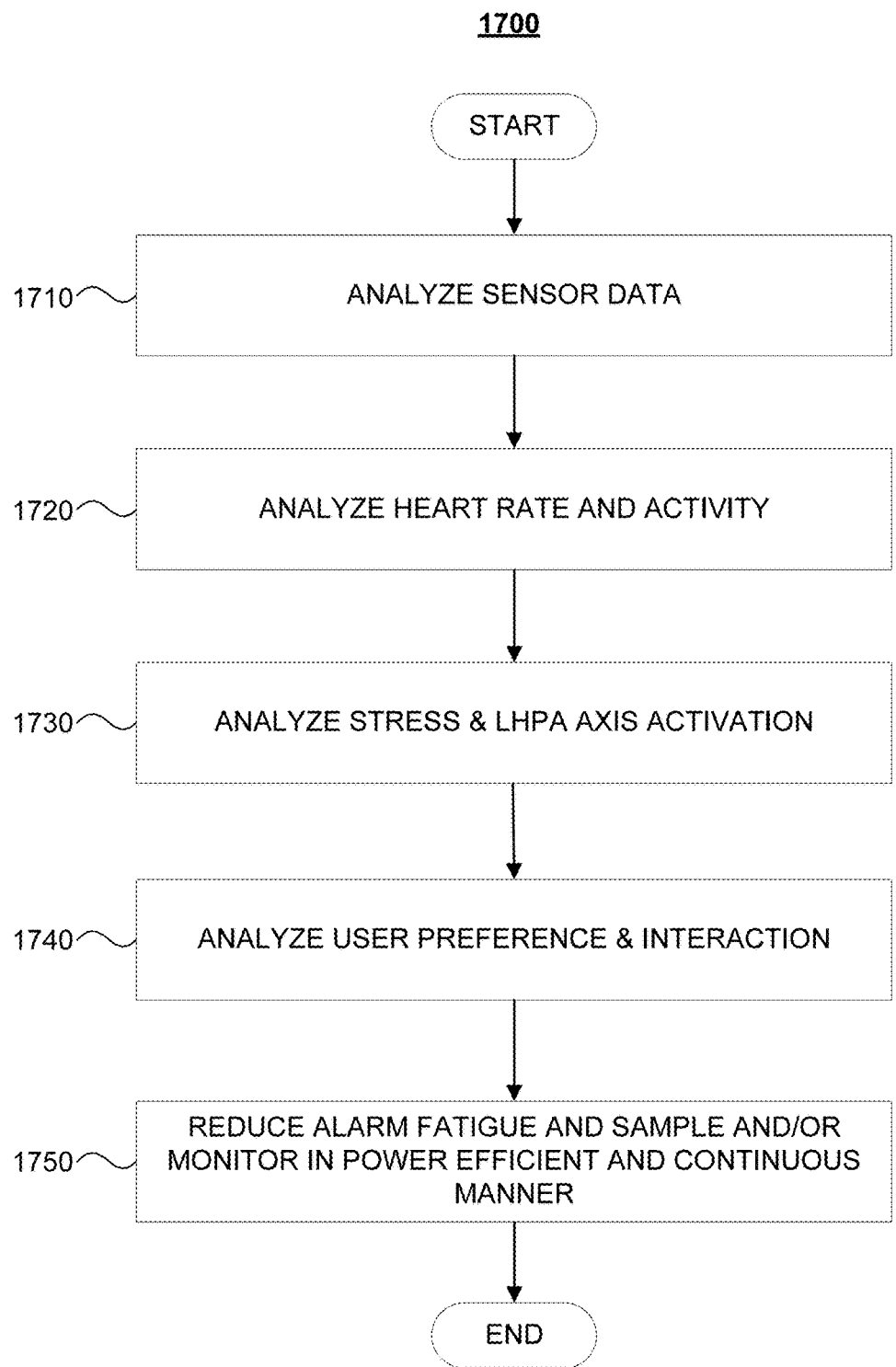
FIG. 17 illustrates an example general method for continuous and power-efficient monitoring of a user's stress level based on biological measurements of the user.

FIG. 17 illustrates an example general method 1700 for continuous and power-efficient monitoring of a user's stress level based on biological measurements of the user. The method begins at step 1710, where health monitoring system 200 may analyze sensor data, as described in more detail below with respect to particular embodiments. At step 1720, health monitoring system 200 may analyze heart rate and activity, as described in more detail below with respect to particular embodiments. At step 1730, health monitoring system 200 may analyze stress and LHPA axis activation, as described in more detail below with respect to particular embodiments. At step 1740, health monitoring system 200 may analyze user preference and interaction, as described in more detail below with respect to particular embodiments. Then, at step 1750, health monitoring system 200 may reduce alarm fatigue reduction and sample and/or monitor in a power efficient and continuous manner, as described in more detail below with respect to particular embodiments. Particular embodiments may repeat one or more steps of the method of FIG. 16, where appropriate. Although this disclosure describes and illustrates particular steps of the method of FIG. 16 as occurring in a particular order, this disclosure contemplates any suitable steps of the method of FIG. 16 occurring in any suitable order. Moreover, although this disclosure describes and illustrates an example method for monitoring the stress level of the user, including the particular steps of the method of FIG. 16, this disclosure contemplates any suitable method for monitoring any relevant physiological markers (e.g., PPG measurements, electrocardiography (EKG) measurements, blood pressure measurements, glucose readings, blood oxygen levels, temperature measurements, sleep duration measurement, sleep quality measurement, respiration parameter measurement (e.g., related to rate, rhythm or volume), cardiac output measurement, activity measurements, posture measurements, hydration measurements, blood hemoglobin level measurements, blood lipid level measurements, weight measurements, height measurement, fat measurement, gait measurement, posture measurement, skin conductance measurement, other suitable health/physiological measurements, or any combination thereof) including any suitable steps, which may include all, some, or none of the steps of the method of FIG. 16, where appropriate. Furthermore, although this disclosure describes and illustrates particular components, devices, or systems carrying out particular steps of the method of FIG. 16, this disclosure contemplates any suitable combination of any suitable components, devices, or systems carrying out any suitable steps of the method of FIG. 16.

As discussed above, the method 1700 for continuous and power-efficient monitoring of a user's stress level may be carried out via health monitoring system 200. The device may include a wearable electronic device (e.g., health monitoring device 210), a mobile device (e.g., client system 120), a dedicated health monitoring device, any other suitable monitoring device, or any combination thereof. As discussed in detail above, the device may include a processor, memory storing program instructions and data, one or more sensors, and a display, where the processor may be configured to take biological measurements of the user using the sensors, and the sensors may include PPG sensors, an accelerometer, other suitable sensor, or any combination (e.g., for determining a heart rate of the user, for determining an activity level of the user, etc.). In particular embodiments, the processor may process the biological measurements and determine a stress level of the user. As described below, based on the processing of the biological measurements, the processor may provide a notification to the user to alert the user of certain stress events.

Alarm Fatigue Reduction

As discussed above, alarm fatigue is a key impediment for users. For example, alarm fatigue may occur when the user is alerted to every stress event that occurs throughout the day because many stress episodes are not harmful (e.g., small duration stress episodes, stress episodes that are controlled by the person after a short homeostatic disturbance, etc.). Alarm fatigue may result in the situation where users are likely to turn off bio-sensing when the reporting of the health status occurs so frequently that the user starts to ignore any further warnings, which may be a serious issue with continuous bio-sensing and health monitoring. Particular embodiments described below are configured to reduce the number of events that trigger alerts to the user by focusing on physiological markers that are truly meaningful, as well as likely actionable (e.g., the user may perform a stress-relieving activity to reduce or mitigate the level of stress). These physiological markers may be used to determine the occurrence of debilitating, physiologically harmful levels of stress, such as chronic or prolonged stress.

By way of background, the limbic-hypothalamic-pituitary-adrenal (LHPA) axis is the central stress response system. When a stress event occurs, the LHPA axis is responsible for the stress response, and this response is characterized by hypothalamic release of corticotropin-releasing hormone (CRF) such that when CRF binds to CRF receptors in the anterior pituitary gland, adrenocorticotropic hormone (ACTH) is released. ACTH then binds to receptors on the adrenal cortex and stimulates adrenal release of cortisol. Cortisol may be released in most people after 25 to 30 minutes after the onset of the stress event. Cortisol then exerts negative feedback to the hypothalamic release of CRF and the pituitary release of ACTH, helping return the system back to stress homeostasis. However, prolonged and repeated release of cortisol may cause or exacerbate numerous health problems, such as heart disease, digestive problems, sleep problems, weight problems, autoimmune diseases, and psychological problems (e.g., depression). Thus, particular embodiments are directed to alerting the user of the occurrence of a stress event and providing recommendations for how to reduce stress and return to homeostasis. In addition, particular embodiments are further directed to providing a stress alert after the onset of the stress event but prior to the release of cortisol such that the user may be able to engage in stress-reducing activities that may mitigate and/or avoid the release of cortisol.

Figure 18:
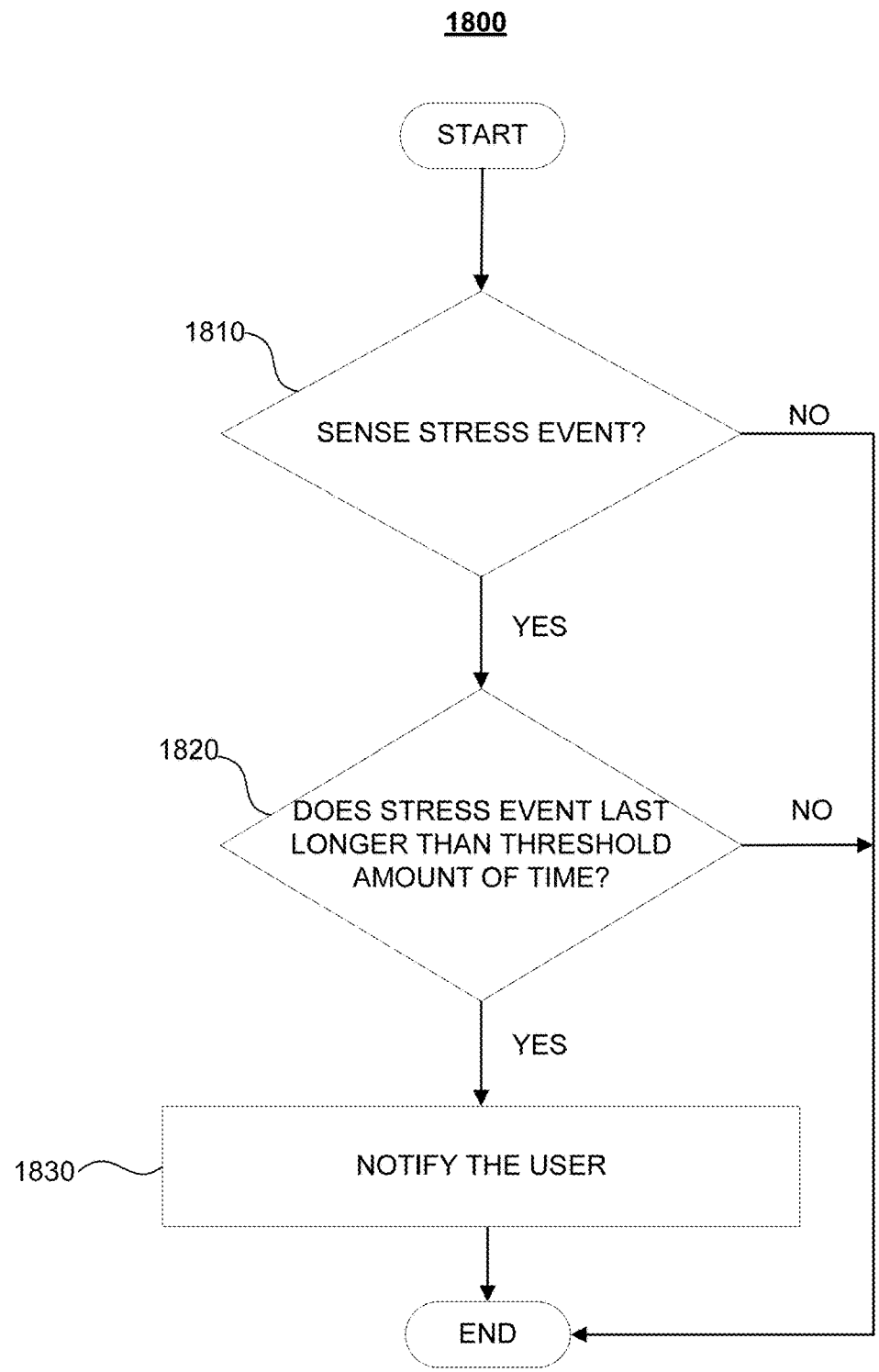
FIG. 18 illustrates an example method for reducing alarm fatigue using health monitoring system.

FIG. 18 illustrates an example method 1800 for reducing alarm fatigue using health monitoring system 200. The method begins at step 1810, where health monitoring system 200 may determine whether there is a stress event. As shown in FIG. 18, when health monitoring system 200 determines that there is no occurrence of a stress event (e.g., "NO" at step 1810), then no notification is sent to the user and the method terminates. On the other hand, when health monitoring system 200 determines that there is an occurrence of a stress event (e.g., "YES" at step 1810), then at step 1820, health monitoring system 200 may then determine whether the stress event lasts longer than a threshold amount of time. As shown in FIG. 18, when health monitoring system determines that the stress event does not last longer than the threshold amount of time (e.g., "NO" at step 1820), then no notification is sent to the user and the method terminates. On the other hand, when health monitoring system 200 determines that the stress event does last longer than the threshold amount of time (e.g., "YES" at step 1820), health monitoring system 200 then proceeds to step 1830. At step 1830, health monitoring system 200 may notify the user of the stress event. Then, the method may terminate.

In particular embodiments, a stress event (e.g., severe stress) may be defined as an event where a stress homeostasis level remains significantly disturbed (e.g., elevated from a baseline stress level for a particular context) for longer than a threshold period of time. As an example and not by way of limitation, the threshold period of time may correspond to a time before a human body may release cortisol in response to the LHPA axis activation (e.g., longer than 15 to 20 minutes, but less than 25-30 minutes). As discussed above, since cortisol may be released in most people after 25 to 30 minutes, this threshold time period may reduce activation of LHPA axis by alerting the user of a stress event that may cause the release of cortisol and/or allow the user to have an opportunity to reduce the stress level prior to, and in avoidance of, the release of cortisol. As another example and not by way of limitation, significant homeostatic disturbance may correspond to a threshold variation in the stress level for a predetermined measurement period (e.g., more than 30% variation in the stress level maintained almost throughout the measurement period, such as 95% of the measurement period).

In particular embodiments, health monitoring system 200 may determine a nature, a level, or an intensity of physical activity of the user (e.g., a context of an activity level) during the time period that the stress level is being measured. As an example and not by way of limitation, the sensors associated with health monitoring system 200, health monitoring device 210, client device 120, or any combination thereof (e.g., an accelerometer, gyroscope, etc.) may be used to sense the nature, level or intensity of the physical activity. This may be used to distinguish an increased heart rate (or other physiological marker) due to emotional state from an increased heart rate due to physical activity.

In particular embodiments, the notification to the user may comprise one or more of user-interface notifications (e.g., message notifications, graphical notifications, etc.), haptic responses (e.g., vibrations, etc.), or audible signals (e.g., any type of noisy signal) by health monitoring system 200, health monitoring device 210, client device 120, another device paired to the health monitoring system 200, or any combination thereof. In addition, based on user preference, the notification may also be communicated to any number of third parties, including family members, friends, close contacts, care providers, other suitable party, or any combination thereof.

Moreover, in particular embodiments, along with the notification, health monitoring system 200 may provide the user with a suggestion/recommendation for an approach to reducing the stress level, which may include activities that are a logical consequence that arises from the stored sensor data detailing the context of an activity level associated with the user. As an example and not by way of limitation, this may include certain physical activities such as getting up and stretching, changing the posture, taking a small walk, hydrating oneself, a short acupressure-like massage, etc. As another example and not by way of limitation, if the sensors detect that the user has been sedentary for a long time, then health monitoring system 200 may recommend to the user to get up and stretch or take a small walk to alleviate stress. As another example and not by way of limitation, if the sensors detect that the user is mobile but under high stress, then health monitoring system 200 may recommend to the user to hydrate himself. As another example and not by way of limitation, if the sensors detect that the user is in certain meeting venues (e.g., a board room), or is unusually still while seated or standing, or when health monitoring system 200 detects that the stress level has spiked up very high in a very short period of time, health monitoring system 200 may recommend a discrete acupressure stimulation of various stress points in the body.

Although this disclosure describes and illustrates particular steps of the method of FIG. 18 as occurring in a particular order, this disclosure contemplates any suitable steps of the method of FIG. 18 occurring in any suitable order. Moreover, although this disclosure describes and illustrates an example method for reducing alarm fatigue using health monitoring system 200, including the particular steps of the method of FIG. 18, this disclosure contemplates any suitable method and any relevant physiological markers (e.g., PPG measurements, EKG measurements, blood pressure measurements, glucose readings, blood oxygen levels, temperature measurements, sleep duration measurement, sleep quality measurement, respiration parameter measurement (e.g., related to rate, rhythm or volume), cardiac output measurement, activity measurements, posture measurements, hydration measurements, blood hemoglobin level measurements, blood lipid level measurements, weight measurements, height measurement, fat measurement, gait measurement, posture measurement, skin conductance measurement, other suitable health/physiological measurements, or any combination thereof) for reducing alarm fatigue including any suitable steps, which may include all, some, or none of the steps of the method of FIG. 18, where appropriate. Furthermore, although this disclosure describes and illustrates particular components, devices, or systems carrying out particular steps of the method of FIG. 18, this disclosure contemplates any suitable combination of any suitable components, devices, or systems carrying out any suitable steps of the method of FIG. 18.

Power Efficient Sampling

As discussed above, power efficient sampling and/or monitoring of the stress level is useful for both monitoring chronic and acute stress. In particular embodiments, for power-efficiency, health monitoring system 200 may monitor chronic by detecting short term prolonged stress longer than 15 minutes based on the notion that the release of cortisol (e.g., LHPA axis activation, as discussed above) is the true short term sign of harmful stress. As an example and not by way of limitation, the method may include an 8 second heart-rate sampling per minute, to compute the heart rate. This heart rate window may be used only when the user is sedentary or engaging in light activity (e.g., so as to not confuse the detection of stress with a high-activity level). When there is a determination of heart rate elevation, then health monitoring system 200 may sample alternate windows to detect the stress level. Based on experimental results, this method my result in power consumption by the sensor to be about 8 to 10 time lower than continuous monitoring. In addition, for power efficiency, health monitoring system 200 may monitor acute stress by detecting acute episodes of stress that last for just a few minutes (e.g., without focusing on LHPA axis activation). As an example and not by way of limitation, the method may include a 20 second heart-rate sampling per minute, only when the user is sedentary or engaging in light activity. When there is a determination of heart rate elevation, then health monitoring system 200 may conduct 40-60 seconds of stress sampling every 60 sec seconds.

Figure 19:
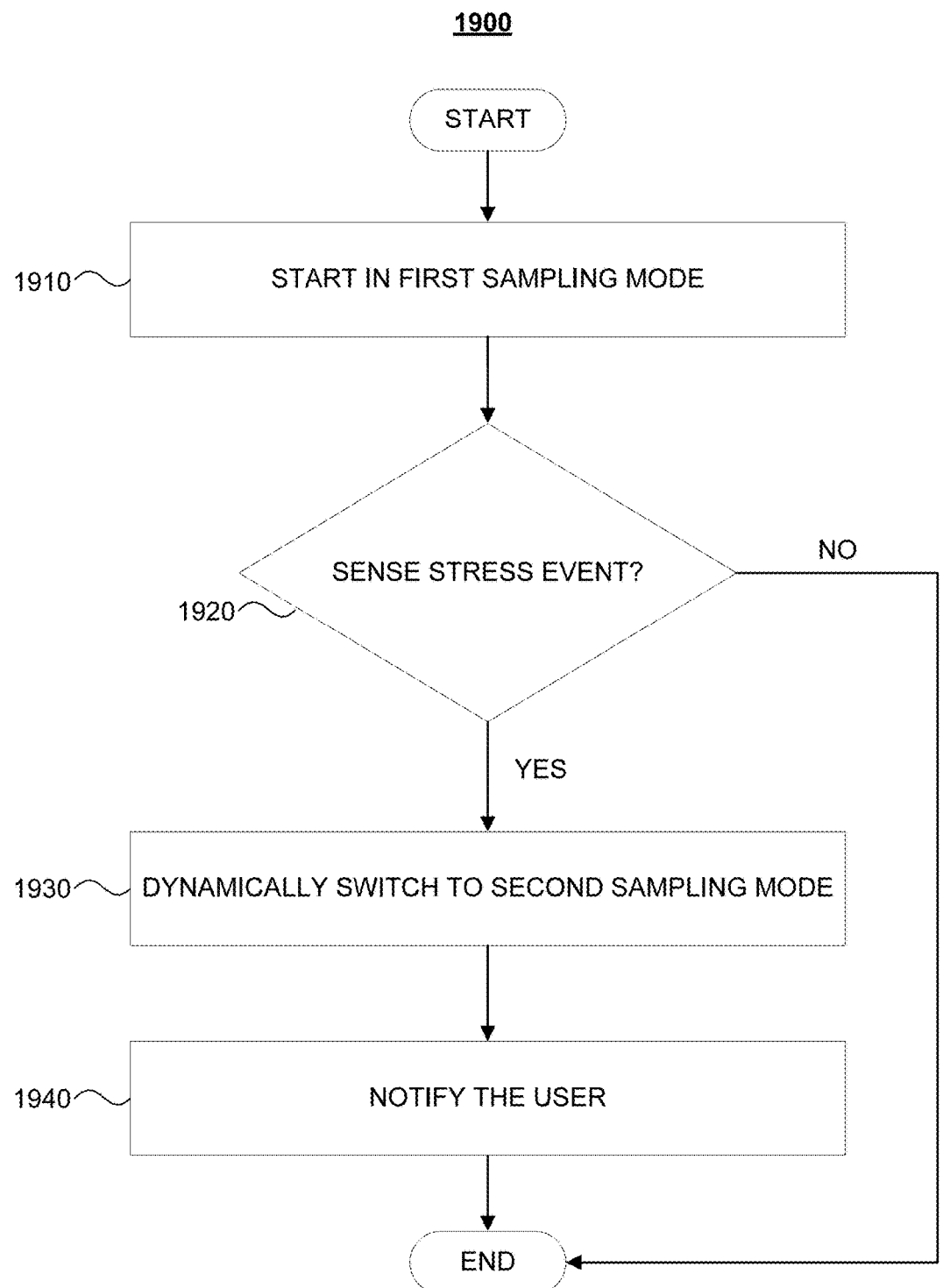
FIG. 19 illustrates an example method for power-efficient monitoring using health monitoring system.

FIG. 19 illustrates an example method 1900 for power-efficient monitoring using health monitoring system 200. The method may begin at step 1910, where health monitoring system 200 starts in a first sampling mode. In particular embodiments, this step may include determining, based on biological measurements on one or more physiological markers receiving in the first sampling mode, the stress level of the user. At step 1920, health monitoring system 200 may determine whether there is a stress event. As shown in FIG. 19, when health monitoring system 200 determines that there is no occurrence of a stress event (e.g., "NO" at step 1920), then no notification is sent to the user and the method terminates. On the other hand, when health monitoring system 200 determines that there is an occurrence of a stress event (e.g., "YES" at step 1920), then at step 1930, health monitoring system 200 may then dynamically switch to a second sampling mode. In particular embodiments, this step may include dynamically switching to the second sampling mode when it is determined that one or more of the physiological markers are above a threshold level, the second sampling mode being different from the first sampling mode. Then, at step 1940, health monitoring system 200 may notify the user. After notifying the user, the method may terminate.

In particular embodiment, health monitoring system 200 may receive, from a sensor of health monitoring system 200, the biological measurements on the physiological markers. As an example and not by way of limitation, the sensors may be associated with health monitoring system 200, health monitoring device 210, client device 120, or any combination thereof, and may include sensors such as an accelerometer, gyroscope, activity-recognition sensors, UV sensors, humidity sensors, sleep sensors, hydration sensors, and bio-sensors such as ECG, PPG, EEG, electromyography (EMG), electrooculograpy (EOG), respiration sensors, other suitable sensors, or any combination thereof. The measurements captured by the sensor may include a nature, level, or intensity of physical activity. In addition, the physiological makers captured by the sensors may include PPG measurements, EKG measurements, blood pressure measurements, glucose readings, blood oxygen levels, temperature measurements, sleep duration measurement, sleep quality measurement, respiration parameter measurement (e.g., related to rate, rhythm or volume), cardiac output measurement, activity measurements, posture measurements, hydration measurements, blood hemoglobin level measurements, blood lipid level measurements, weight measurements, height measurement, fat measurement, gait measurement, posture measurement, skin conductance measurement, other suitable health/physiological measurements, or any combination thereof.

In particular embodiments, the notification may be associated as discussed above, health monitoring system 200 may send the notification to the user via health monitoring device 210, client device 120, other suitable device, or any combination thereof. As discussed above, the notification may comprise one or more of user-interface notifications (e.g., message notifications, graphical notifications, etc.), haptic responses (e.g., vibrations, etc.), or audible signals (e.g., any type of noisy signal) by health monitoring system 200, health monitoring device 210, client device 120, another device paired to the health monitoring system 200, or any combination thereof. In addition, based on user preference, the notification may also be communicated to any number of third parties, including family members, friends, close contacts, care providers, other suitable party, or any combination thereof.

In particular embodiments, the first sampling mode is a low-power mode and the second sampling mode is a high-power mode, and the low-power mode is associated with a first detection time period and the high-power mode is associated with a second detection time period. The second detection time period may correspond to a longer detection time period for a predetermined time period than the first detection time period (e.g., the first detection time period may correspond to a 20 second heart rate sampling window every minute, while the second detection time period may correspond to a 40 second heart rate sampling window every minute). In addition, the second detection time period may correspond to a higher frequency of detection time periods with a predetermined time period than the first detection time period (e.g., the first detection time period may correspond to a detection window of 5 seconds per 10 seconds of every minute, while the second detection period may correspond to a detection window of 8 seconds per 10 seconds of every minute).

In particular embodiments, health monitoring system 200 may determine a context associated with user during the first sampling mode based on the biological measurements, the context being defined by one or more of a nature, a level, or an intensity of physical activity during the first sampling mode. As an example and not by way of limitation, as discussed above, the sensors associated with health monitoring system 200, health monitoring device 210, client device 120, or any combination thereof (e.g., an accelerometer, gyroscope, etc.) may be used to sense the nature, level or intensity of the physical activity. This may be used to distinguish an increased heart rate (or other physiological marker) due to emotional state from an increased heart rate due to physical activity. In particular embodiments, as discussed in more detail below, health monitoring system 200 may dynamically switch back to the first sampling mode when it is determined that the one or more physiological markers are not above the threshold level.

In particular embodiments, an episodic-sampling method may include receiving the heartbeat, physical activity, and other physiological information from the sensors associated with health monitoring system 200. As an example and not by way of limitation, heart rate information is generated from the sensor for a single and continuous series of approximately 8 seconds every minute, and the physical activity information is received continuously. Then, health monitoring system 200 may compute the average heart rate and the nature, level, and intensity of the activity of the user (e.g., using the accelerometer). If the heart rate is above a baseline heart rate (e.g., a user-specific baseline heart rate) by a certain threshold (e.g., such as 10%), and is not due to a physical activity that can describe such a hear rate elevation, then health monitoring system 200 may adjust the sampling window a single and continuous time series of 30 seconds every minute.

Then, health monitoring system 200 may initiate future sampling of alternate 30-second time windows as long as the stress computed in the previously-sampled window is high (e.g., above a user-defined threshold). If, on the other hand, health monitoring system 200 determines that the previously-sampled window is no longer high (e.g., above the user-defined threshold), health monitoring system 200 may revert back to computing heart rate for 8 seconds per every minute. In addition, as an alternative, instead of computing the stress level for only every alternate window, health monitoring system 200 may compute an average stress value over a given period of time (e.g., an hour, an entire day, etc.) by adding the alternate windows.

In particular embodiments, the low-power mode may correspond to a measurement of a first physiological marker, and the high-power mode may correspond to a measurement of a second physiological marker different from the first physiological marker. As an example and no by way of limitation, as discussed in more detail below, the low-power mode may correspond to a measurement of an average heart rate of the user (e.g., which involves less intensive algorithms and is less computationally expensive), and the high-power mode may correspond to a measurement of a HRV of the user (e.g., which involves more intensive algorithms and is more computationally expensive).

In particular embodiments, health monitoring system 200 may, prior to determining the stress level of the user, receive a selection of one or more stress-monitoring modes from the user, wherein the stress-monitoring modes comprises a chronic-stress-monitoring mode and an acute-stress-monitoring mode. In other words, the user may choose whether health monitoring system 200 is to be operated in the chronic-stress-monitoring mode or the acute-stress-monitoring mode, or both. As an example and not by way of limitation, when a user selects both the modes, this can be accomplished by setting a high threshold for acute stress monitoring mode to be triggered because an acute stress event that requires immediate attention will be one where the stress level of the user is severely high (e.g., a stress level that approaches an extremely low HRV, such as to a value that is less than 10% of the estimated range in which the quantified stress values may change).

On the other hand, a chronic stress episode is defined as a stress episode that lasts for a long period of time, and to capture such an episode, health monitoring system 200 may continually sense the stress of the user so that a long period of high-level stress is determined. However, continuously sensing the user's stress level may be very energy consuming with respect to the power consumed by the sensors being deployed for the stress monitoring. In particular embodiments, for better power efficiency, health monitoring system 200 may not keep the sensors ON for the full period of time during which health monitoring system 200 is engaged in monitoring the user's stress. Instead, in particular embodiments, a method for determining chronic/prolonged or acute stress may include health monitoring system 200 first receiving a user preference for being monitored for chronic stress, or acute stress, or both. Health monitoring system 200 may then detect the physiological markers (e.g., the user's heart rate) based on the above-described episodic-sampling method.

In particular embodiments, health monitoring system 200 may determine that the detected stress level is acutely high if the computed stress level is above a threshold (e.g., 40% or more sustained elevation of the computed stress level) and meets other criterion (e.g., total stress level elevation time of 5 minutes or more) that are associated with identifying an acute stress level. Then, health monitoring system 200 may provide a notification and feedback/recommendations to the user based on the acute stress level (e.g., if such a preference was selected by the user).

On the other hand, in particular embodiments, health monitoring system 200 may determine that the detected stress level is chronically high/prolonged if the computed stress is above a threshold (e.g., 40% or more sustained elevation of the computed stress) and meets other criterion (e.g., total stress elevation time of 25 minutes or more) that are associated with identifying a chronic stress level. Then, health monitoring system 200 may provide a notification and feedback/recommendations to the user based on the chronic stress level (e.g., if such a preference was selected by the user).

In addition, if health monitoring system 200 is set to provide a warning for impending LHPA axis activation that may overwhelm the stress homeostasis, then health monitoring system 200 may provide such a notification after that period (e.g., around 15 minutes after the initial high stress and/or stress event was detected).

In particular embodiments, in the presence of sustained accelerometer activity, the health monitoring system 200 may provide a (e.g., default) option to turn off the concurrent heart rate sensing. This may provide additional gains in power efficiency.

In particular embodiments, the method may include hierarchical decision-making capabilities. As an example and not by way of limitation, health monitoring system 200 may use a low energy sensor to test the elevation in stress level (e.g., by using a galvanic skin response (GSR)-like sensor) before beginning the more expensive monitoring based on PPG signals. Similarly, health monitoring system 200 may use one or more sophisticated filers before invoking a more expensive sensing modality. As an example and not by way of limitation, health monitoring system 200 that may sense for the user's stress level every alternate period of 30 seconds may be replaced by one that senses periods of 45 seconds with an interim gap that is smaller in length (e.g., 15 seconds), or an interim gap that is longer in length (e.g., 45 seconds). In general, sampling decisions may be determined based on the sensed stress level and the user preference where health monitoring system 200 may optimize energy consumed as well as meeting the monitoring requirements of the user.

Although this disclosure describes and illustrates particular steps of the method of FIG. 19 as occurring in a particular order, this disclosure contemplates any suitable steps of the method of FIG. 19 occurring in any suitable order. Moreover, although this disclosure describes and illustrates an example method for power-efficient monitoring using health monitoring system 200, including the particular steps of the method of FIG. 19, this disclosure contemplates any suitable method and any relevant physiological markers (e.g., PPG measurements, EKG measurements, blood pressure measurements, glucose readings, blood oxygen levels, temperature measurements, sleep duration measurement, sleep quality measurement, respiration parameter measurement (e.g., related to rate, rhythm or volume), cardiac output measurement, activity measurements, posture measurements, hydration measurements, blood hemoglobin level measurements, blood lipid level measurements, weight measurements, height measurement, fat measurement, gait measurement, posture measurement, skin conductance measurement, other suitable health/physiological measurements, or any combination thereof) for power-efficient monitoring including any suitable steps, which may include all, some, or none of the steps of the method of FIG. 19, where appropriate. Furthermore, although this disclosure describes and illustrates particular components, devices, or systems carrying out particular steps of the method of FIG. 19, this disclosure contemplates any suitable combination of any suitable components, devices, or systems carrying out any suitable steps of the method of FIG. 19.

User Baseline Contexts and Stress Coping Capacity

As discussed above, in mobile health monitoring and management, use of wearable devices is considered to be key for creating novel methods and systems in health management. Health measurements may be a bridge to management of a wide variety of health problems, such as diabetes, stress, hypertension, cardiovascular diseases, pulmonary diseases, mood disorder, substance-abuse, general quality of life, etc. A contextual baselining approach may be applied to a set of user-specific physiological measurements to make those measurements sensible, thereby providing real feedback about what the user is doing to improve or hurt the user's health, and how the user's body is reacting to different situations. Similarly, stress monitoring and management should also be context aware (e.g., analyzing stress measurements relative to the context of the stress measurement). Accordingly, non-invasive stress measurements combined with contextual awareness may provide a powerful tool for dealing with stress and/or other physiological measurements, recognizing harmful stress levels, diagnosing stress as a cause for a symptom, etc.

Example Embodiments of Context Engine Associated with Health Monitoring Engine

Figure 20:
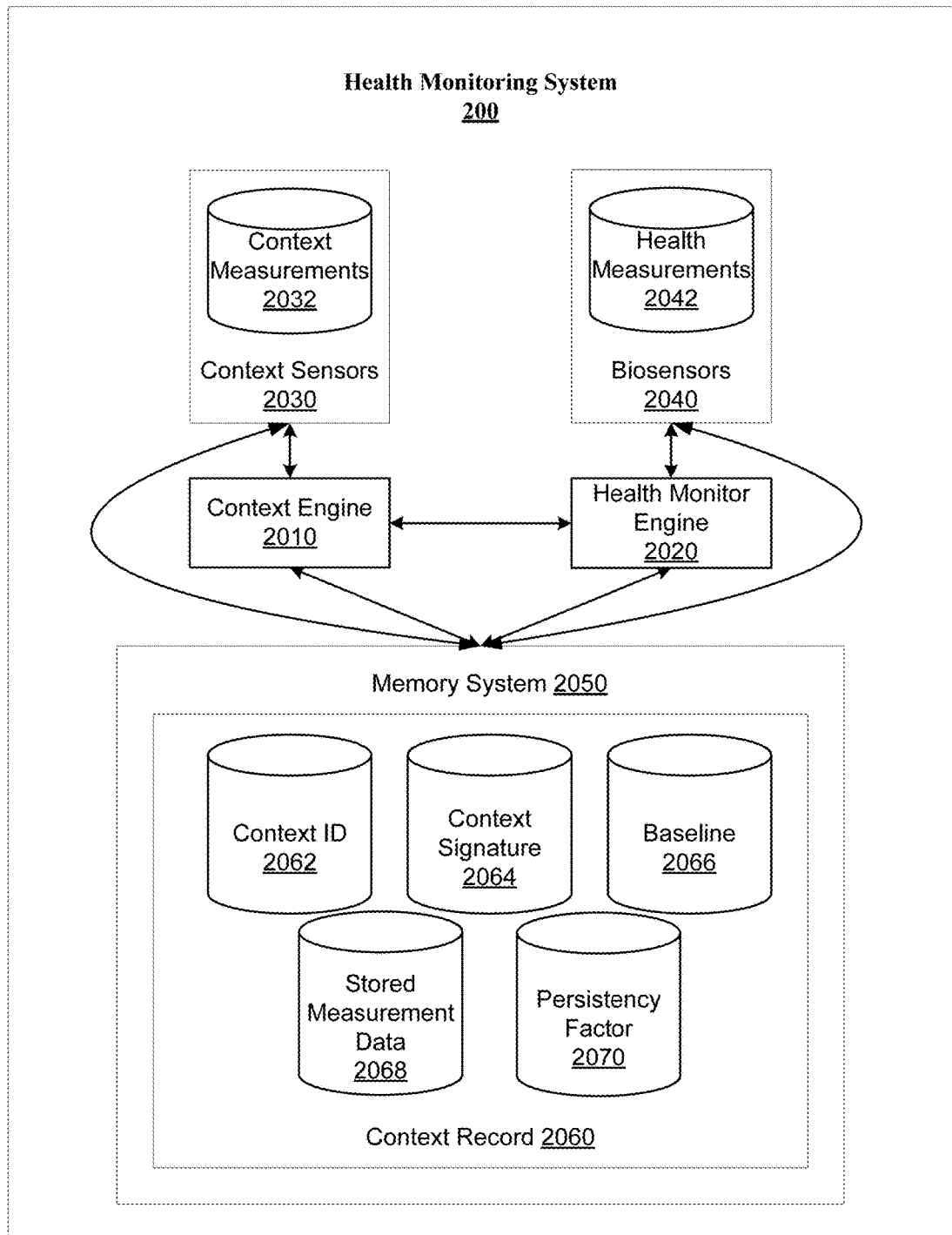
FIG. 20 illustrates example software and hardware components of health monitoring system.

FIG. 20 illustrates example software and hardware components of health monitoring system 200. In particular embodiments, health monitoring system 200 may include a context engine 2010, a health monitor engine 2020, one or more context sensors 2030, one or more biosensors 2040, and a memory system 2050. Health monitoring system 200 may be deployed on a number of types of devices, such as a wearable device (e.g., health monitoring device 210), a mobile device (e.g., client system 120), a personal computer (e.g., client system 120), a dedicated medical monitoring device, a smart TV, other suitable device, and any combination thereof. As discussed in more detail below, health monitoring system 200 may be configured to detect, monitor, and analyze a number of health measurements 2042 (e.g., physiological measurements) of a user and determine a health characteristic of the user as an output. As an example and not by way of limitation, health measurements 2042 may include PPG measurements, EKG measurements, blood pressure measurements, glucose readings, blood oxygen levels, temperature measurements, sleep duration measurement, sleep quality measurement, respiration parameter measurement (e.g., related to rate, rhythm or volume), cardiac output measurement, activity measurements, posture measurements, hydration measurements, blood hemoglobin level measurements, blood lipid level measurements, weight measurements, height measurement, fat measurement, gait measurement, posture measurement, skin conductance measurement, other suitable health/physiological measurements, or any combination thereof.

In addition, as an example and not by way of limitation, a health characteristic may include stress, heart rate, blood pressure, glucose level, arrhythmia, respiratory parameters such as rate, rhythm and volume, peripheral and/or core temperature, hydration level, galvanic skin response, EEG characteristics, EMG characteristics, gait, posture, activity, sleep, cardiac output, weight, body mass index (BMI), bone mineral density (BMD), other relevant health characteristic, or any combination thereof. In particular embodiments, the health characteristic may be determined relative to one or more contexts. As an example and not by way of limitation, the contexts may include at the office vs. at home, awake vs. asleep, weekdays vs. weekends, day vs. night, morning vs. evening, before sleep vs. after sleep, indoor vs. outdoors, leisure activity vs. predetermined daily chores, before exercise vs. after exercise, alone vs. with company, healthy vs. sick, poor posture vs. correct posture, calm vs. fidgety, quiet vs. vocal, hydrated vs. dehydrated, hypertensive vs. normotensive, hungry vs. well-fed, low oxygen saturation vs. normal oxygen saturation, other relevant contexts, or any combination thereof. In particular embodiments, the context may be associated with a baseline (e.g., a user-specific baseline) of the health characteristic, which a current health characteristic may be measured against. In particular embodiments, health monitoring system 200 may determine the context in an automatic, semi-automatic, or manual method. Moreover, health monitoring system 200 may update the baseline of each context in an automatic, semi-automatic, or manual manner.

In particular embodiments, context engine 2010 may be configured to receive one or more context measurements 2032 and determine a context. As an example and not by way of limitation, contexts may be defined by space-time coordinates and may be determined or selected based by using a calendar, a time-clock, GPS, in-plane switching (IPS), ultraviolet (UV) sensors, humidity sensors, barometer, other suitable context definitions/selections, or any combination thereof. Context measurements 2032 may be provided by context sensors 2030. As an example and not by way of limitation, context measurements 2032 may include GPS measurements, accelerometer measurements, calendar measurements, time measurements, in-IPS measurements, temperature measurements, sound measurements, posture measurements, activity measurements, UV light measurements, sound measurements, barometer measurements, other suitable measurements, or any combination thereof. In addition, context sensors 2030 may include UV sensors, humidity sensors, a barometer, GPS, IPS, the calendar, other suitable sensors, or any combination thereof. The context may be selected from a database of context records stored by memory system 2050. In addition, health monitor engine 2020 may be configured to receive the context output from the context engine and also receive health measurements 2042 from biosensors 2040.

In particular embodiments, memory system 2050 stores a plurality of context records 2060, which is available via context engine 2010. Each of context records 2060 may be representative of a context of the user such that the collection of contexts represents each possible context (e.g., user-specific context) that health monitoring system 200 may distinguish. As shown in FIG. 20, context records 2060 include a number of data entries (e.g., data fields) that are representative of a context ID 2062, a context signature 2064, a baseline value 2066, stored measurement data 2068, and a persistency factor 2070. Context ID 2062 may be a unique identifier and/or name for a context record of context records 2060. As an example and not by way of limitation, context ID 2062 may correspond to "work week," "weekend," "commute," "exercise," "playing a video game," other suitable context identifiers, or any combination thereof. Context signature 2064 may be a set of values that context measurement 2032 are compared to. As an example and not by way of limitation, context engine 2010 may select a particular context record of the plurality of context records 2060 in response to determining that context measurements 2062 match context signature 2064 of the particular context record.

Baseline 2066 may represent the baseline values of the health characteristics of the user for the corresponding context. Stored measurement data 2068 may include stored context measurements (e.g., previously collected by context sensors 2030) and/or health measurements (e.g., previously collected by biosensors 2040). Stored measurement data 2068 may be used to update context signature 2064 and/or to identify new contexts based on patterns of user behavior or activities. As an example and not by way of limitation, health monitoring system 200 may track context measurements 2032 of the user and analyze them for patterns. In response to matching a pattern, health monitoring system 200 may prompt the user to confirm that a corresponding new context has occurred and/or whether the user would like to "activate" the new context for future monitoring. Persistency factor 2070 may be data that represents how long the effects of a particular context may be taken into account. As an example and not by way of limitation, a stressful commute may affect the context of the user for up to 4 hours after the commute has finished.

Figure 21:
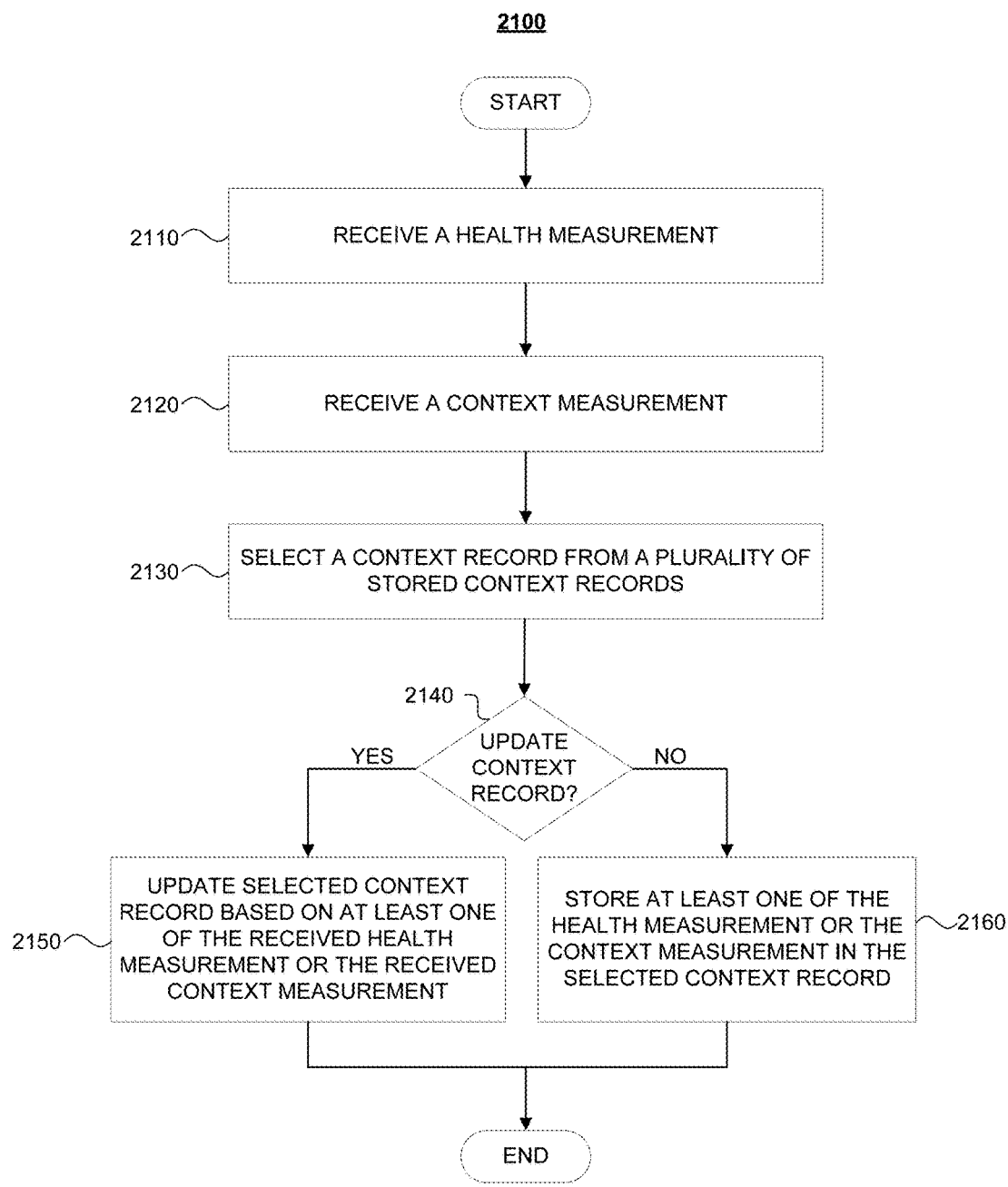
FIG. 21 illustrates an example method for generating and/or updating context records of a user.

FIG. 21 illustrates an example method 2100 for generating and/or updating context records of a user. The method may begin at step 2110, where health monitoring system 200 may receive a health measurement (e.g., health measurements 2042 via biosensors 2040). In particular embodiments, in response to receiving the health measurement, health monitoring system 200 may request context engine 2010 to determine the current context. As such, at step 2120, health monitoring system 200 may receive a context measurement (e.g., context measurements 2032 via context sensor 2030). In particular embodiments, health monitoring system 200, via context engine 2010, may compare the received context measurements to the context signature data fields (e.g., context signature 2064) of context records 2060 stored for the user by memory system 2050. Then, at step 2130, health monitoring system 200 may select a context record from a plurality of stored context records (e.g., from context record 2060 stored in memory system 2050) having a context signature matching the context measurements.

In particular embodiments, the context may include information on a given location, activity, weather, and other relevant space-time information. As an example and not by way of limitation, with respect to the activity information, using just accelerometers and gyroscopes, health monitoring system 200 may identify certain activities, such as walking, running, biking, exercising, other similar activities, and any applicable combination thereof. As another example and not by way of limitation, using additional sensors such as UV sensors, humidity sensors, sleep sensors, hydration sensors, and bio-sensors such as ECG, PPG, EEG, EMG, EOG, respiration sensors, etc., an activity may be defined by a method which first attempts to define an event with respect to any label that one of the sensors can impose upon the user's activity (e.g., Context A), which may be either provided to the system by the user or determined by the value of the sensors (e.g., Content S). As an example and not by way of limitation, Context A may include contexts such as the user being in a boardroom, after a particular time on a weekday morning, when the user is at a hospital or at an old age nursing home, after doing some chores at home (e.g., which can be detected by an activity-recognition sensor), the user being sedentary at his desk with poor posture for more than 1 hour, the user sleeping later than a certain time, the user getting after a certain time, other suitable contexts, or any combination thereof. These contexts may have a specific connotation or meaning for the user and hence he cares about monitoring his stress in such contexts.

In particular embodiments, the context may be automatically detected by health monitoring system 200. Automatically-detected contexts may be pre-populated into memory system 2050 of health monitoring system 200 or dynamically determined after learning the user's characteristic health/stress profile. As an example and not by way of limitation, Context S may include a user's weekend or weekday (regular) commute, the user being at work, the user being at a park during a weekend, the user being in a noisy environment, the user being at a high elevation, low oxygen saturation, the user being outside a high ultraviolet light index, the user waking up with a restless or short sleep, the user being dehydrated, the user being sedentary at work for a very long time, the user just completing intense physical exertion or sitting front of his television in his living room for a long period of time, the user having a very angry outburst (e.g., as detected by voice analysis from the mobile device sensors), other automatically detectable contexts, and any applicable combination thereof. In particular embodiments, contexts may be generated by concurrent analysis of multiple sensors at the same time.

At step 2140, health monitoring system 200 may determine whether to update the selected context record. If the determination at step 2140 is YES, then the method moves on to step 2150, where health monitoring system 200 may update the selected context record based on at least one of the received health measurement or the received context measurement. In particular embodiments, the determination of whether the context record is to be updated may be based on a number of factors (e.g., the number of unprocessed stored health measurements of the context record, an amount of time since the last update to the context record, etc.). As an example and not by way of limitation, each context may be associated with what are the normal values for other contexts, and the baseline data for the given context may only be updated if these other context values remain within a normal/predetermined range. In particular embodiments, in response to a determination that the context record is to be updated, context engine 2010 of health monitoring system 200 may update the baseline value of the selected context record. As an example and not by way of limitation, the baseline value for a context may be generated by taking an average of a set of readings on that context (e.g., where the set may be either defined by the user or be the set of all readings for that given context). As another example and not by way of limitation, the baseline may be generated based on a weighted average with a decaying window or moving window so that old measurements are discarded over time. In particular embodiments, context engine 2010 of health monitoring system 200 may automatically update the baseline value of the selected context record. After the selected context record is updated, the method may terminate.

On the other hand, if the determination at step 2140 is NO, then the method moves on to step 2160, where health monitoring system 200 may store at least one of the health measurement or the context measurement in the selected context record. In particular embodiments, in response to a determination that the context record is not to be updated, context engine 2010 of health monitoring system 200 may store the received health measurements in the stored measurement data field (e.g., via stored measurement data 2068) of the selected context record. The stored health measurements may then be accessed and/or processed at a later time. Then, the method may terminate.

In particular embodiments, for stress monitoring, users may each have a different baseline stress level (e.g., based on HRV), and thus the stress-level determination must consider the baseline of each individual user. However, the baseline stress level itself is different based on the context (e.g., at the office vs. at home, awake vs. asleep, weekdays vs. weekends, etc.) and/or activity (e.g., before, during or after sleep, meals, exercise, consuming media content, doing household chores, etc.). The methods described above may be configured to automatically create correct baselines for different contexts based on collected context measurements 2032 and health measurements 2042. As such, the context may be defined not just using space-time co-ordinates but also in terms of the context (e.g., repeated biological states) and/or activity performed (e.g., repeated user activity).

Particular embodiments may repeat one or more steps of the method of FIG. 21, where appropriate. Although this disclosure describes and illustrates particular steps of the method of FIG. 21 as occurring in a particular order, this disclosure contemplates any suitable steps of the method of FIG. 21 occurring in any suitable order. Moreover, although this disclosure describes and illustrates an example method for generating and/or updating context records of a user including the particular steps of the method of FIG. 21, this disclosure contemplates any suitable method for generating and/or updating context records of a user including any suitable steps, which may include all, some, or none of the steps of the method of FIG. 21, where appropriate. Furthermore, although this disclosure describes and illustrates particular components, devices, or systems carrying out particular steps of the method of FIG. 21, this disclosure contemplates any suitable combination of any suitable components, devices, or systems carrying out any suitable steps of the method of FIG. 21.

Performing Health Monitoring Based on Contexts

Figure 22:
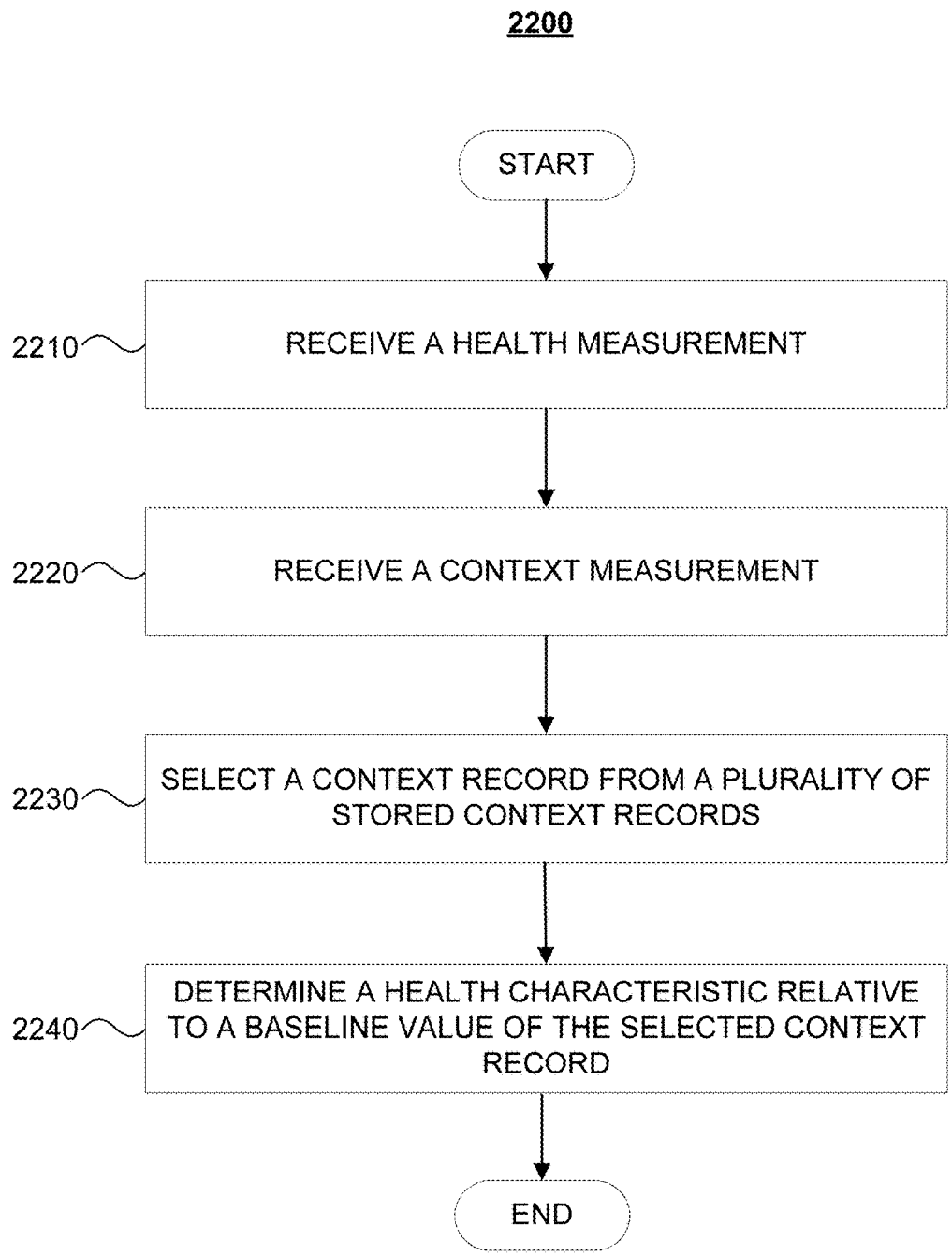
FIG. 22 illustrates an example method for generating a health characteristic output for the user.

FIG. 22 illustrates an example method 2200 for generating a health characteristic output for the user. The method may begin at step 2210, where health monitoring system 200 may receive a health measurement (e.g., health measurements 2042 via biosensors 2040). In response, health monitoring system 200 may request context engine 2010 to determine the current context in order to evaluate the health measurement. At step 2220, health monitoring system 200 may receive a context measurement (e.g., context measurements 2032 via context sensor 2030). At step 2230, health monitoring system 200 may select a context record from a plurality of stored context records (e.g., from context record 2060 stored in memory system 2050). In particular embodiments, context engine 2010 may then select a context record of the plurality of context records 2060 stored by memory system 2050 by comparing the received context measurements to the context signature data fields of the context records (e.g., via context signature 2064) stored by memory system 2050. Context engine 2010 selects the context record of the record having a context signature matching or substantially similar to the received context measurements. The selected context record includes the baseline value (e.g., via baseline 2066) of the determined context. As an example and not by way of limitation, the baseline value may be a user-specific baseline value for a particular context. Then, at step 2240, health monitoring system 200 may determine a health characteristic relative to a baseline value of the selected context record. As such, health monitoring system 200 may compute the health characteristic based on the received health measurement and in comparison with the baseline value of the selected context.

In particular embodiments, health monitoring system 200 may monitor one or more health characteristics of the user (e.g., stress level, heart rate, HRV, etc.) and provide the user an output that is representative of the health characteristic. Additionally or alternatively, the health characteristic can be stored for later retrieval, such as by a doctor for diagnostic purposes.

In particular embodiments, health monitoring system 200 may facilitate user-in-the-loop operation to select the context. As an example and not by way of limitation, health monitoring system 200 may operate in a fully manual way so that the user may supply user input to define a number of contexts and/or indicate the current context. Additionally or alternatively, health monitoring system 200 may provide the user with a list of prepopulated contexts to choose from. Over time, health monitoring system 200 may update the baseline values when the user selects the context. Alternatively, in particular embodiments, health monitoring system 200 may operate in a semi-automatic way, wherein health monitoring system 200 may provide the user with prompts to confirm automatic detection of context or to request that the user select the context in the event that the system cannot determine the context. In addition, in particular embodiments, health monitoring system 200 may automatically select the context based on the received context measurements.

Particular embodiments may repeat one or more steps of the method of FIG. 22, where appropriate. Although this disclosure describes and illustrates particular steps of the method of FIG. 22 as occurring in a particular order, this disclosure contemplates any suitable steps of the method of FIG. 22 occurring in any suitable order. Moreover, although this disclosure describes and illustrates an example method for generating a health characteristic output for the user including the particular steps of the method of FIG. 22, this disclosure contemplates any suitable method for generating a health characteristic output for the user including any suitable steps, which may include all, some, or none of the steps of the method of FIG. 22, where appropriate. Furthermore, although this disclosure describes and illustrates particular components, devices, or systems carrying out particular steps of the method of FIG. 22, this disclosure contemplates any suitable combination of any suitable components, devices, or systems carrying out any suitable steps of the method of FIG. 22.

Determining Emotional Health and Resiliency

A number of existing stress monitoring tools only provide various forms of raw stress values, which does not provide a useful measure for health maintenance, that is, the resiliency of the user. As an example, health monitoring system 200 may compute the time a user spends in a given HRV zone (e.g., showing high stress or high relaxation). As this time increases or decreases, the user gets a resiliency factor on whether his stress coping skills or relaxation maintenance capacity has shown any improvements. Health monitoring system 200 may compute various such measurements as a useful measure of the user's stress coping skills, or benefit from any wellness program he may be undertaking in overcoming stress or maintaining a state of relaxation.

In particular embodiments, health monitoring system 200 may utilize the resiliency factor (e.g., a health resiliency measurement) of the context record to determine the lasting effects of events. As an example and not by way of limitation, the effects of a stressful drive or the effects of a stressful workday, or the calm provided by reading a book may be taken into account. In particular embodiments, the resiliency factor can correspond to a period of time for analyzing the baseline value of the context after the context is over based on a determination that over time, the effect of a previous context may decrease abruptly or gradually. In particular embodiments, the baseline value may be a combination of the baselines of the active contexts (e.g., including the previous context within the resiliency period and the current context). As an example and not by way of limitation, the combination of the baselines may be determined based on the maximum, the minimum, the average, or a convex combination of the baselines.

Figure 23:
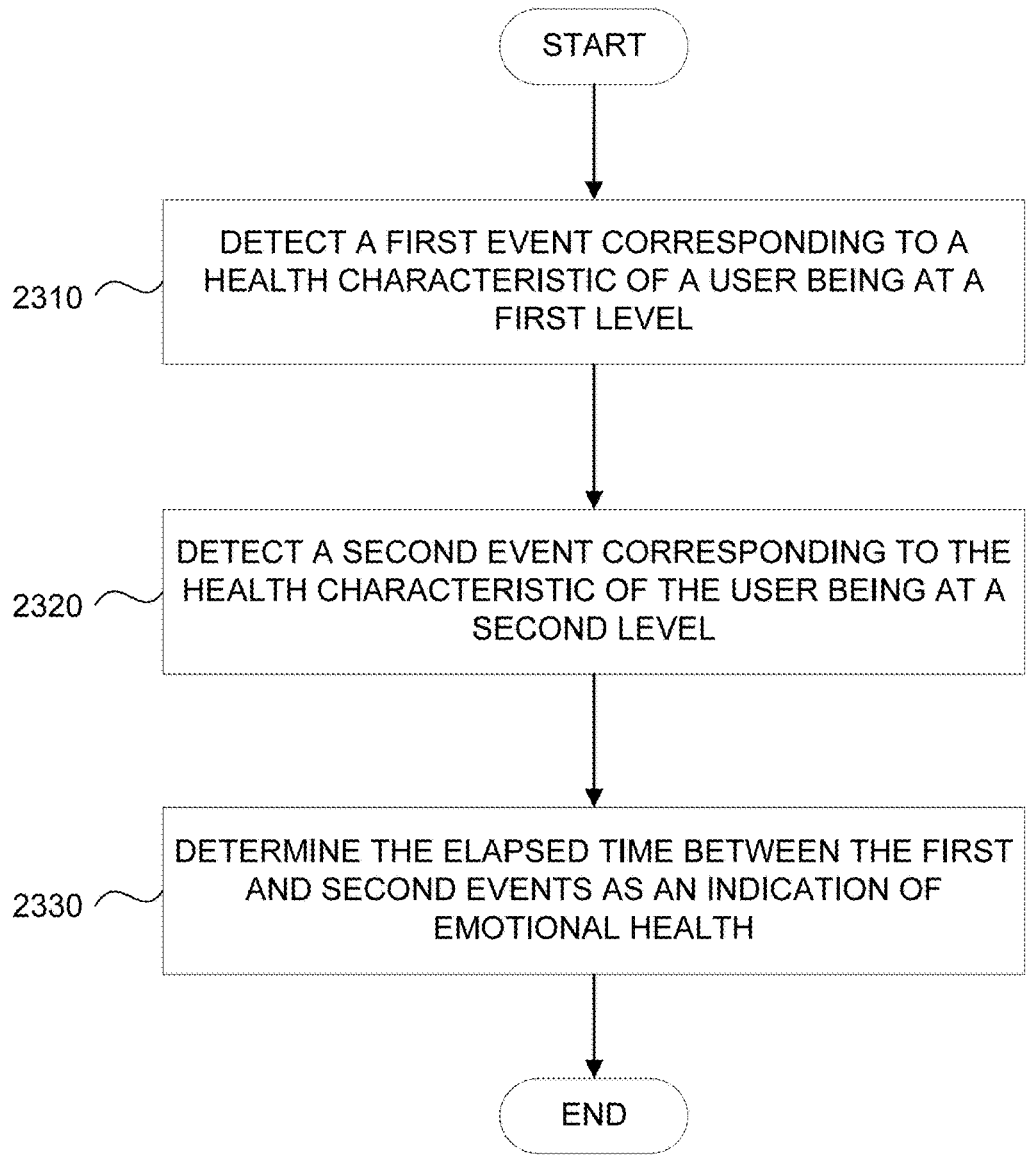
FIG. 23 illustrates an example method for determining a user's emotional health based on a health-resiliency measurement.

FIG. 23 illustrates an example method 2300 for determining a user's emotional health based on a health-resiliency measurement. The method may begin at step 2310, where health monitoring system 200 may detect a first event corresponding to a health characteristic of a user being a first level. At step 2320, health monitoring system 200 may detect a second event corresponding to the health characteristic of the user being at a second level. At step 2330, health monitoring system 200 may determine the elapsed time between the first and second events as an indication of emotional health, wherein the elapsed time between the first and second events may correspond to a health-resiliency measurement associated with the user.

In particular embodiments, stress resilience for any user for a given context may be measured by determining a time T taken by the user to make a transition from a first range of stress values (e.g., defined as one of a set of labels of possible stress values or as a numeric value) to a second range of stress values, within the later range may be defined as a baseline state for the particular context. Alternatively, in particular embodiments, stress resilience may be defined as D/T, where D is the difference between the original stress value and the final stress value, and T is the time taken to make this transition. Moreover, a "relaxation" resilience may be defined using a similar approach. As an example and not by way of limitation, when multiple instances of a health-resiliency measurement corresponding to stress has already been computed in which the health resilience corresponds to an average time to recover back to a pre-defined stress zone (e.g., an HRV zone between 40-60), the stress resilience for a context C may be determined based on $$SR = \frac{1}{n}\Sigma_{k=0}^{n} t_i,$$

where context C includes n events (e.g., $\{e_1, \ldots, e_n\}$), and the recovery time is $\{t_1, \ldots, t_n\}$. In particular embodiments, such information may be provided to the user using charts that show the HRV recovery time along with the context & actual value of HRV.

In particular embodiments, as discussed above, the health-resiliency measurement may be improved by including types of events/contexts to help interpret the health-resiliency measurement. As such, an extension of the previously-described resilience computations may include a functionality of "contextual resilience." In particular embodiments, contextual resilience may be a marker of allostatic load being imposed by events and contexts, and such information may be helpful to the user because it provides a functionality for determining which situations reduce emotional health, and what changes in the lifestyle may led to better resilience and better emotional coping capacity. As an example and not by way of definition, if during weekdays the user's stress resilience is very low, then health monitoring system 200 may give provide feedback to the user that he has a lower emotional health during this period. In contrast, if the user is in a post-exercise period, then health monitoring system 200 may give provide feedback to the user that he has high emotional health and high stress resilience during this period.

In particular embodiments, the quantification scale associated with resiliency allows for consistent stages of severe stress, high stress, moderate stress, etc. In a panic attack or severe stress episodes, the recovery time may be defined in stages and hence the resiliency measurement is more useful than a stress level at any particular state. As an example and not by way of limitation, in the instance of a panic attack or severe stress episode, a user's stress health may be provided by health monitoring system 200 as a tuple such as (resilience_escape, resilience_normal) where resilience-escape corresponds to a time required for the user to completely come out of a severe stress zone (hold time), and resilience_normal corresponds to a time required to completely come back to a normal zone (recovery time). The hold time may alternatively be defined as starting from any specific point in the stress zone. Thus, this quantification scale associated with resiliency may allow variety of stress scenarios to be accommodated. Moreover, these stress management functionalities, in addition to those described above, may be used to determine and quantify how well the stress reduction techniques are working for the user.

In particular embodiments, with regard to notifications to the user associated with resiliency, when health monitoring system 200 determines that the baseline of the user has shifted upwards after a period of use, or if his stress baseline is otherwise significantly affected, then he can be provided stress reduction options as consistent with this situations and his preferences. Similarly, when health monitoring system 200 determines that the user's stress resilience has worsened, health monitoring system 200 may provide the user with assistance and/or recommendations that are commensurate with this new health status. These suggestions may be provided to the user automatically or be chosen by the user from a menu of options that changes based on the health status of the user. In particular embodiments, the above-described resiliency not limited to stress, and may be used to quantify other measurements such as mental states, arousal (e.g., sadness, irritation, etc.), other suitable measurements, and any combination thereof.

As discussed above, the contexts can be computed based upon space and time coordinates as well as activities or the pattern of the activities. In particular embodiments, the notifications to the user may be tailored based on the type of measurements that are made about the context, the baseline value, and the corresponding resiliency measurement (e.g., providing recommendations that are based on an awareness of the need of the context as well as what has been known to be effective for the user). As an example and not by way of limitation, if the stress detected is high in the context of a boardroom meeting and the baseline value of such measurements has been continually increasing and/or the resilience continually worsening, then a notification of stress reduction may be sent to the user which is consistent with the constraints imposed by the user's setting.

In particular embodiments, improvements in resilience may be used to quantify or assess the benefits of a particular stress management service. As such, the contextual baseline values and resiliency-measurement determinations may provide a logical metric around which diagnosis and services can be built.

Particular embodiments may repeat one or more steps of the method of FIG. 23, where appropriate. Although this disclosure describes and illustrates particular steps of the method of FIG. 23 as occurring in a particular order, this disclosure contemplates any suitable steps of the method of FIG. 23 occurring in any suitable order. Moreover, although this disclosure describes and illustrates an example method for determining a user's emotional health based on a health-resiliency measurement including the particular steps of the method of FIG. 23, this disclosure contemplates any suitable method for determining a user's emotional health based on a health-resiliency measurement including any suitable steps, which may include all, some, or none of the steps of the method of FIG. 23, where appropriate. Furthermore, although this disclosure describes and illustrates particular components, devices, or systems carrying out particular steps of the method of FIG. 23, this disclosure contemplates any suitable combination of any suitable components, devices, or systems carrying out any suitable steps of the method of FIG. 23.

Systems and Methods

Figure 24:
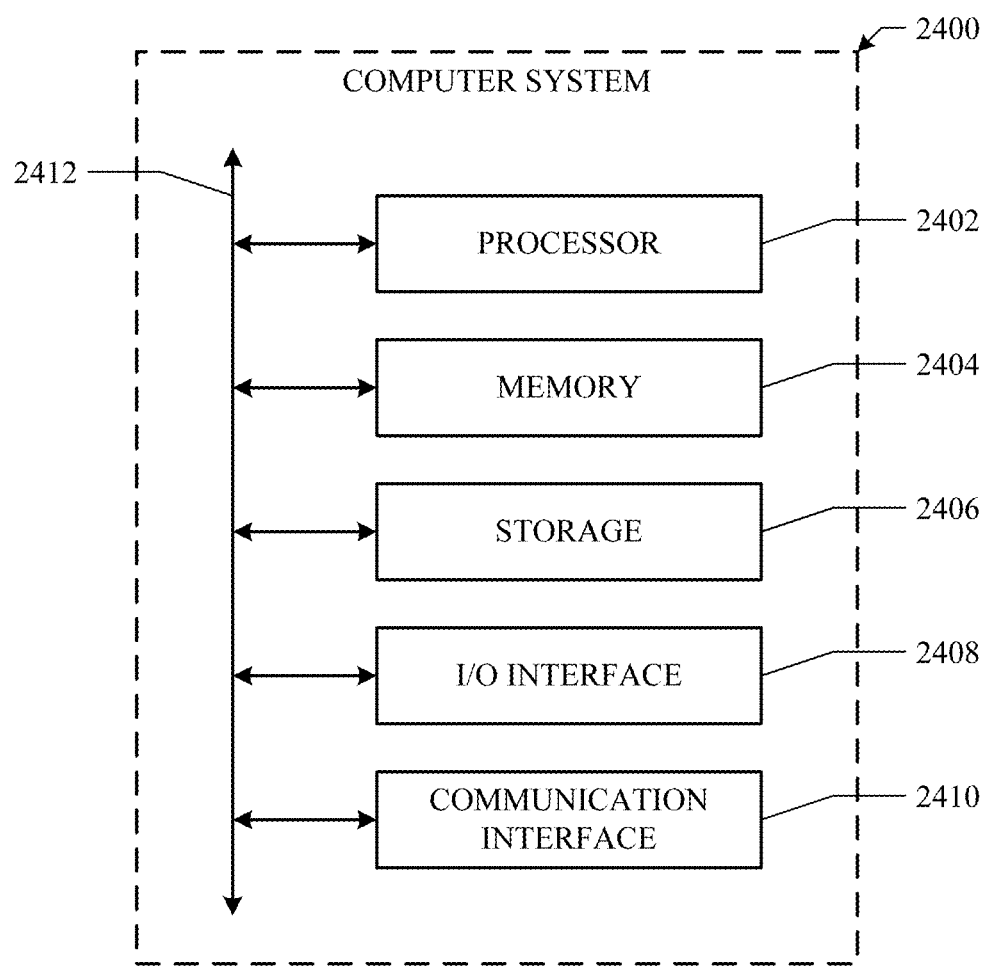
FIG. 24 illustrates an example computer system according to particular embodiments of the invention.

FIG. 24 illustrates an example computer system 2400 according to some embodiments of the invention. In particular embodiments, one or more computer systems 2400 perform one or more steps of one or more methods described or illustrated herein. In particular embodiments, one or more computer systems 2400 provide functionality described or illustrated herein. In particular embodiments, software running on one or more computer systems 2400 performs one or more steps of one or more methods described or illustrated herein or provides functionality described or illustrated herein. Particular embodiments include one or more portions of one or more computer systems 2400. Herein, reference to a computer system may encompass a computing device, and vice versa, where appropriate. Moreover, reference to a computer system may encompass one or more computer systems, where appropriate.

This disclosure contemplates any suitable number of computer systems 2400. This disclosure contemplates computer system 2400 taking any suitable physical form. As example and not by way of limitation, computer system 2400 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 2400 may include one or more computer systems 2400; be unitary or distributed; span multiple locations; span multiple machines; span multiple data centers; or reside in a cloud, which may include one or more cloud components in one or more networks. Where appropriate, one or more computer systems 2400 may perform without substantial spatial or temporal limitation one or more steps of one or more methods described or illustrated herein. As an example and not by way of limitation, one or more computer systems 2400 may perform in real time or in batch mode one or more steps of one or more methods described or illustrated herein. One or more computer systems 2400 may perform at different times or at different locations one or more steps of one or more methods described or illustrated herein, where appropriate.

In particular embodiments, computer system 2400 includes a processor 2402, memory 2404, storage 2406, an input/output (I/O) interface 2408, a communication interface 2410, and a bus 2412. Although this disclosure describes and illustrates a particular computer system having a particular number of particular components in a particular arrangement, this disclosure contemplates any suitable computer system having any suitable number of any suitable components in any suitable arrangement.

In particular embodiments, processor 2402 includes hardware for executing instructions, such as those making up a computer program. In particular embodiments, the computer program causes the processor 2402 to perform one or more steps of one or more methods described or illustrated herein or provides functionality described or illustrated herein. In this way, the processor 2402 coupled to the computer program is a special purpose processor for performing the functions defined by the computer program. As an example and not by way of limitation, to execute instructions, processor 2402 may retrieve (or fetch) the instructions from an internal register, an internal cache, memory 2404, or storage 2406; decode and execute them; and then write one or more results to an internal register, an internal cache, memory 2404, or storage 2406. In particular embodiments, processor 2402 may include one or more internal caches for data, instructions, or addresses. This disclosure contemplates processor 2402 including any suitable number of any suitable internal caches, where appropriate. As an example and not by way of limitation, processor 2402 may include one or more instruction caches, one or more data caches, and one or more translation lookaside buffers (TLBs). Instructions in the instruction caches may be copies of instructions in memory 2404 or storage 2406, and the instruction caches may speed up retrieval of those instructions by processor 2402. Data in the data caches may be copies of data in memory 2404 or storage 2406 for instructions executing at processor 2402 to operate on; the results of previous instructions executed at processor 2402 for access by subsequent instructions executing at processor 2402 or for writing to memory 2404 or storage 2406; or other suitable data. The data caches may speed up read or write operations by processor 2402. The TLBs may speed up virtual-address translation for processor 2402. In particular embodiments, processor 2402 may include one or more internal registers for data, instructions, or addresses. This disclosure contemplates processor 2402 including any suitable number of any suitable internal registers, where appropriate. Where appropriate, processor 2402 may include one or more arithmetic logic units (ALUs); be a multi-core processor; or include one or more processors 2402. Although this disclosure describes and illustrates a particular processor, this disclosure contemplates any suitable processor.

In particular embodiments, memory 2404 includes main memory for storing instructions for processor 2402 to execute or data for processor 2402 to operate on. As an example and not by way of limitation, computer system 2400 may load instructions from storage 2406 or another source (such as, for example, another computer system 2400) to memory 2404. Processor 2402 may then load the instructions from memory 2404 to an internal register or internal cache. To execute the instructions, processor 2402 may retrieve the instructions from the internal register or internal cache and decode them. During or after execution of the instructions, processor 2402 may write one or more results (which may be intermediate or final results) to the internal register or internal cache. Processor 2402 may then write one or more of those results to memory 2404. In particular embodiments, processor 2402 executes only instructions in one or more internal registers or internal caches or in memory 2404 (as opposed to storage 2406 or elsewhere) and operates only on data in one or more internal registers or internal caches or in memory 2404 (as opposed to storage 2406 or elsewhere). One or more memory buses (which may each include an address bus and a data bus) may couple processor 2402 to memory 2404. Bus 2412 may include one or more memory buses, as described below. In particular embodiments, one or more memory management units (MMUs) reside between processor 2402 and memory 2404 and facilitate accesses to memory 2404 requested by processor 2402. In particular embodiments, memory 2404 includes random access memory (RAM). This RAM may be volatile memory, or may be dynamic RAM (DRAM) or static RAM (SRAM). Moreover, where appropriate, this RAM may be single-ported or multi-ported RAM. This disclosure contemplates any suitable RAM. Memory 2404 may include one or more memories 2404, where appropriate. Although this disclosure describes and illustrates particular memory, this disclosure contemplates any suitable memory.

In particular embodiments, storage 2406 includes mass storage for data or instructions. As an example and not by way of limitation, storage 2406 may include a hard disk drive (HDD), a floppy disk drive, flash memory, an optical disc, a magneto-optical disc, magnetic tape, or a Universal Serial Bus (USB) drive or a combination of two or more of these. Storage 2406 may include removable or non-removable (or fixed) media, where appropriate. Storage 2406 may be internal or external to computer system 2400, where appropriate. In particular embodiments, storage 2406 is non-volatile, solid-state memory. In particular embodiments, storage 2406 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 2406 taking any suitable physical form. Storage 2406 may include one or more storage control units facilitating communication between processor 2402 and storage 2406, where appropriate. Where appropriate, storage 2406 may include one or more storages 2406. Although this disclosure describes and illustrates particular storage, this disclosure contemplates any suitable storage.

In particular embodiments, I/O interface 2408 includes hardware, software, or both, providing one or more interfaces for communication between computer system 2400 and one or more I/O devices. Computer system 2400 may include one or more of these I/O devices, where appropriate. One or more of these I/O devices may enable communication between a person and computer system 2400. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 2408 for them. Where appropriate, I/O interface 2408 may include one or more device or software drivers enabling processor 2402 to drive one or more of these I/O devices. I/O interface 2408 may include one or more I/O interfaces 2408, where appropriate. Although this disclosure describes and illustrates a particular I/O interface, this disclosure contemplates any suitable I/O interface.

In particular embodiments, communication interface 2410 includes hardware, software, or both providing one or more interfaces for communication (such as, for example, packet-based communication) between computer system 2400 and one or more other computer systems 2400 or one or more networks. As an example and not by way of limitation, communication interface 2410 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 2410 for it. As an example and not by way of limitation, computer system 2400 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 2400 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 2400 may include any suitable communication interface 2410 for any of these networks, where appropriate. Communication interface 2410 may include one or more communication interfaces 2410, where appropriate. Although this disclosure describes and illustrates a particular communication interface, this disclosure contemplates any suitable communication interface.

In particular embodiments, bus 2412 includes hardware, software, or both coupling components of computer system 2400 to each other. As an example and not by way of limitation, bus 2412 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 2412 may include one or more buses 2412, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Miscellaneous

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method for monitoring a health characteristic of a user based on one or more biological measurements, comprising:
   determining a current context of a user;
   accessing a plurality of contexts for the user, wherein:
   each of the plurality of contexts identifies a context-specific baseline health value; and
   each of the plurality of contexts is defined at least in part by a plurality of recorded events each comprising one or more of repeated biological states, repeated user activity, or space-time coordinates of the user;
   identifying from the plurality of contexts a predefined user context corresponding to the current context of the user;

monitoring the health characteristic of the user based on one or more bio-sensing measurements in comparison to the context-specific baseline health value corresponding to the identified predefined user context;

detecting, based on monitoring the health characteristic, a plurality of event pairs, each event pair comprising:
- a first event corresponding to the health characteristic of the user being within a first pre-defined variability zone; and
- a second event corresponding to the health characteristic of the user being within a second pre-defined variability zone;

determining, for each event pair, an amount of time between the first and second event; and determining a context-specific health-resiliency measurement specific to the user, the identified predefined user context, and the health characteristic by averaging over the plurality of event pairs the determined amount of time between the first and second events.

2. The method of claim 1, wherein the one or more bio-sensing measurements comprises one or more health measurements received from one or more sensors of an electronic device of the user.

3. The method of claim 1, wherein determining the current context of the user comprises:
receiving a plurality of current-context measurements from an electronic device of the user; and
determining the current context based on one or more of the received current-context measurements.

4. The method of claim 3, wherein the current context is automatically determined by the electronic device of the user.

5. The method of claim 1, wherein the context-specific baseline health value identified by each of the plurality of contexts is user-specific.

6. The method of claim 1, wherein the health characteristic corresponds to an estimated stress level of the user.

7. The method of claim 6, wherein the context-specific baseline health value corresponds to a baseline stress level of the user for that particular one of the plurality of contexts.

8. The method of claim 1, wherein the health characteristic corresponds to an estimated heart rate of the user.

9. The method of claim 1, wherein the health characteristic corresponds to an estimated heart-rate variability (HRV) of the user.

10. The method of claim 1, further comprising:
generating a first context by identifying a pattern of repeated biological states or repeated activity of the user based on the bio-sensing measurements; and
determining a baseline health value associated with the first context.

11. The method of claim 10, wherein an electronic device of the user automatically generates the first context based on the identified patterns.

12. The method of claim 10, wherein an electronic device of the user automatically detects one or more new contexts that are different than any of the plurality of contexts.

13. The method of claim 1, wherein the health characteristic is stored on an electronic device of the user or on another device associated with the electronic device.

14. The method of claim 1, wherein:
the health characteristic corresponds to an estimated stress level of the user;
the first event is associated with a stress event;
the second event is associated with a relaxation event; and
the health-resiliency measurement is a measurement of the amount of time it takes for the user to recover from the stress event to the relaxation event.

15. One or more computer-readable non-transitory storage media embodying software for monitoring a health characteristic of a user based on one or more biological measurements, that is operable when executed to:
determine a current context of a user;
access a plurality of contexts for the user, wherein:
 each of the plurality of contexts identifies a context-specific baseline health value; and
 each of the plurality of contexts is defined at least in part by a plurality of recorded events each comprising one or more of repeated biological states, repeated user activity, or space-time coordinates of the user;
identify from the plurality of contexts a predefined user context corresponding to the current context of the user;
monitor the health characteristic of the user based on one or more bio-sensing measurements in comparison to the context-specific baseline health value corresponding to the identified predefined user context;
detect, based on monitoring the health characteristic, a plurality of event pairs, each event pair comprising:
 a first event corresponding to the health characteristic of the user being within a first pre-defined variability zone; and
 a second event corresponding to the health characteristic of the user being within a second pre-defined variability zone;
determine, for each event pair, an amount of time between the first and second event; and
determine a context-specific health-resiliency measurement specific to the user, the identified predefined user context, and the health characteristic by averaging over the plurality of event pairs the determined amount of time between the first and second events.

16. The media of claim 15, wherein the health characteristic corresponds to an estimated stress level of the user.

17. The media of claim 16, wherein:
the first event is associated with a stress event;
the second event is associated with a relaxation event; and
the health-resiliency measurement is a measurement of the amount of time it takes for the user to recover from the stress event to the relaxation event.

18. A system comprising: one or more processors; and a non-transitory memory coupled to the processors comprising instructions executable by the processors for monitoring a health characteristic of a user based on one or more biological measurements, the processors operable when executing the instructions to:
determine a current context of a user;
access a plurality of contexts for the user, wherein:
 each of the plurality of contexts identifies a context-specific baseline health value; and
 each of the plurality of contexts is defined at least in part by a plurality of recorded events each comprising one or more of repeated biological states, repeated user activity, or space-time coordinates of the user;
identify from the plurality of contexts a predefined user context corresponding to the current context of the user;
monitor the health characteristic of the user based on one or more bio-sensing measurements in comparison to the context-specific baseline health value corresponding to the identified predefined user context;
detect, based on monitoring the health characteristic, a plurality of event pairs, each event pair comprising:
a first event corresponding to the health characteristic of the user being within a first pre-defined variability zone; and
a second event corresponding to the health characteristic of the user being within a second pre-defined variability zone;
determine, for each event pair, an amount of time between the first and second event; and
determine a context-specific health-resiliency measurement specific to the user, the identified predefined user context, and the health characteristic by averaging over the plurality of event pairs the determined amount of time between the first and second events.

19. The system of claim 18, wherein the health characteristic corresponds to an estimated stress level of the user.

20. The system of claim 19, wherein:
the first event is associated with a stress event;
the second event is associated with a relaxation event; and
the health-resiliency measurement is a measurement of the amount of time it takes for the user to recover from the stress event to the relaxation event.

* * * * *